US008466289B2

(12) United States Patent  
Bock et al.

(10) Patent No.: US 8,466,289 B2
(45) Date of Patent: Jun. 18, 2013

(54) HETEROCYCLIC SULFONAMIDE DERIVATIVES

(75) Inventors: Mark G. Bock, Boston, MA (US); Dinesh Chikkanna, Karnataka (IN); Clive McCarthy, Froidefontaine (FR); Henrik Moebitz, Freiburg (DE); Chetan Pandit, Karnataka (IN)

(73) Assignee: Novartis AG, Basel (CH)

(*) Notice: Subject to any disclaimer, the term of this patent is extended or adjusted under 35 U.S.C. 154(b) by 214 days.

(21) Appl. No.: 12/938,583

(22) Filed: Nov. 3, 2010

(65) Prior Publication Data

US 2011/0190334 A1 Aug. 4, 2011

(30) Foreign Application Priority Data

Nov. 4, 2009 (IN) .............................. 2678/CHE/09

(51) Int. Cl.
*C07D 513/04* (2006.01)
*C07D 471/04* (2006.01)
*C07D 498/04* (2006.01)
*A61K 31/437* (2006.01)
*A61K 31/4355* (2006.01)
*A61K 31/4365* (2006.01)

(52) U.S. Cl.
USPC ........... 546/114; 546/115; 546/121; 514/300; 514/301; 514/302

(58) Field of Classification Search
USPC ................. 546/114, 115, 121; 514/301, 302, 514/300
See application file for complete search history.

(56) References Cited

U.S. PATENT DOCUMENTS

| | | | |
|---|---|---|---|
| 6,977,266 B2 | 12/2005 | Tada et al. | |
| 7,652,141 B2 | 1/2010 | Tada et al. | |
| 7,803,839 B2 | 9/2010 | Aay et al. | |
| 7,820,664 B2 | 10/2010 | Vernier et al. | |
| 2005/0101590 A1 | 5/2005 | Yasui et al. | |
| 2007/0244164 A1 | 10/2007 | Yan et al. | |
| 2008/0312292 A1 | 12/2008 | Yasui et al. | |
| 2009/0082328 A1 | 3/2009 | Li et al. | |
| 2009/0124595 A1 | 5/2009 | Adams et al. | |
| 2009/0275606 A1 | 11/2009 | Chikkanna et al. | |
| 2010/0249096 A1 | 9/2010 | Aay et al. | |
| 2010/0331334 A1 | 12/2010 | Koh et al. | |

FOREIGN PATENT DOCUMENTS

| | | |
|---|---|---|
| EP | 1357111 A1 | 10/2003 |
| EP | 1477186 A1 | 11/2004 |
| EP | 2130820 A1 | 12/2009 |
| WO | WO03070277 A1 | 8/2003 |
| WO | WO2007014011 A2 | 2/2007 |
| WO | WO2007044515 A1 | 4/2007 |
| WO | WO2007121481 A2 | 10/2007 |
| WO | WO2008089459 A1 | 7/2008 |
| WO | WO2008138639 A1 | 11/2008 |
| WO | WO2009018238 A1 | 2/2009 |
| WO | WO2009064675 A1 | 5/2009 |
| WO | WO2009129938 A1 | 10/2009 |
| WO | WO2010003025 A1 | 1/2010 |
| WO | WO2010105082 A1 | 9/2010 |
| WO | WO2010121646 A1 | 10/2010 |

OTHER PUBLICATIONS

Roberts et. al. "Targeting the Raf-MEK-ERK mitogen-activated protein kinase cascade for the treatment of cancer." Oncogene (2007) 26, 3291-3310.*
Simone, Oncology: Introduction, Cecil Textbook of Medicine, 20th Edition, 1996 vol. 1, pp. 1004-1010.*
Trisha Gura "Cancer Models: Systems for Identifying New Drugs Are Often Faulty" Science Nov. 7, 1997: vol. 278. No. 5340, pp. 1041-1042.*

* cited by examiner

*Primary Examiner* — David K O Dell
(74) *Attorney, Agent, or Firm* — Scott W. Reid

(57) ABSTRACT

The present invention relates to compounds of Formula I

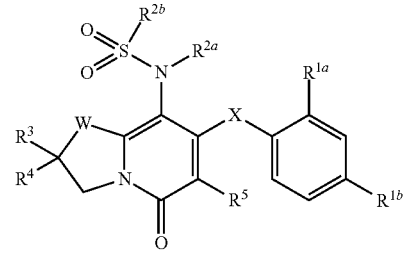

(IA)

where $R^{1a}$, $R^{1b}$, X, $R^{2a}$, $R^{2b}$, W, $R^3$, $R^4$, and $R^5$ are as defined herein as well as pharmaceutically acceptable salts thereof. The compounds have been shown to act as MEK inhibitors which may be useful in the treatment of hyperproliferative diseases, like cancer and inflammation.

11 Claims, No Drawings

HETEROCYCLIC SULFONAMIDE DERIVATIVES

This application claims benefit under 35 U.S.C. §119(b) of Indian Application No. 2678/CHE/09, filed Nov. 4, 2009, the contents of which are incorporated herein by reference in their entirety.

FIELD OF THE INVENTION

The invention relates to heterocyclic sulfonamide compounds and pharmaceutical compositions thereof, in particular heterocyclic sulfonamide compounds that are specific inhibitors of kinase activity of MEK. The invention also relates to the use of the compounds and compositions thereof in the management of hyperproliferative diseases like cancer and inflammation.

BACKGROUND

Hyperproliferative diseases like cancer and inflammation are receiving a lot of attention from the scientific community and there is a strong desire to discover compounds that provide therapeutic benefits with regard to treating hyperproliferative diseases. In this regard efforts have been made to identify and target specific mechanisms which play a role in proliferating the diseases.

One target of interest is the over-activation of mitogen-activated protein (MAP) kinase cascade which is known to play an important role in cell proliferation and differentiation. This pathway can be activated when a growth factor binds to its receptor tyrosine kinase. This interaction promotes RAS association with RAF and initiates a phosphorylation cascade through MEK (MAP kinase) to ERK. Inhibition of this pathway is known to be beneficial in treating hyperproliferative diseases. MEK is an attractive therapeutic target because the only known substrates for MEK phosphorylation are the MAP kinases, ERK1 and ERK2. Constitutive activation of MEK/ERK was been found in pancreatic, colon, lung, kidney and ovarian primary tumor samples.

Phosphorylation of MEK appears to increase its affinity and its catalytic activity toward ERK as well as is affinity for ATP. This invention describes compounds that inhibit MEK activity by modulation of ATP binding, association of MEK with ERK by mechanisms that are competitive, and/or allosteric and/or uncompetitive.

Activation of MEK has been demonstrated in many disease models thus suggesting that inhibition of MEK could have potential therapeutic benefit in various diseases such as Pain (see, e.g., Evidence of efficacy in pain models described in *J. Neurosci.* 22:478, 2002; *Acta Pharmacol Sin.* 26:789 2005; *Expert Opin Ther Targets.* 9:699, 2005; and *Mol. Pain.* 2:2, 2006): Stroke (see, e.g., Evidence of efficacy in stroke models significant neuroprotection against ischemic brain injury by inhibition of the MEK described in *J. Pharmacol. Exp. Ther.* 304:172, 2003; and Brain Res. 996:55, 2004); Diabetes (see, e.g., Evidence in diabetic complications described in Am. J. Physiol. Renal. 286, F120 2004); Inflammation (see e.g., Evidence of efficacy in inflammation models described in *Biochem Biophy. Res. Com.* 268:647, 2000); and Arthritis (see, e.g., Evidence of efficacy in experimental osteoarthritis and arthritis as described in *J. Clin. Invest.* 116:163. 2006).

Although inhibition of MEK has been shown to have potential therapeutic benefit in several studies, there still remains a need to find compounds having commercial application.

SUMMARY

The invention provides a sulfonamide compound of Formula (IA) is provided

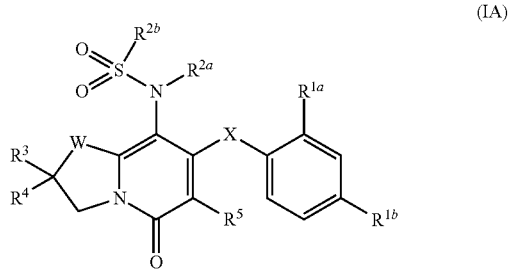

(IA)

wherein

X is —N(R$^6$)—, where R$^6$ is H or (C$_1$-C$_6$)alkyl;

R$^{1a}$ and R$^{1b}$ are each independently selected from hydroxyl, cyano, nitro, (C$_1$-C$_6$)alkyl, (C$_2$-C$_6$)alkenyl, (C$_2$-C$_6$)alkynyl, (C$_1$-C$_6$)alkoxy, (C$_2$-C$_6$)alkenyloxy, (C$_2$-C$_6$)alkynyloxy, halogen, (C$_1$-C$_6$)alkyl-C(O)—, —C(O)OH, —C(O)—O(C$_1$-C$_6$)alkyl, amino, (C$_1$-C$_6$)alkylNH—, di((C$_1$-C$_6$)-alkyl)N—, (C$_1$-C$_6$)alkylNH—C(O)—, di((C$_1$-C$_6$)alkyl)N—C(O)—, (C$_1$-C$_6$)alkyl-C(O)—NH—, (C$_1$-C$_6$)alkyl-C(O)—N((C$_1$-C$_6$)alkyl)-, (C$_1$-C$_6$)alkyl-SO$_2$—NH—, (C$_1$-C$_6$)alkyl-SO$_2$—N((C$_1$-C$_6$)alkyl)-, (C$_1$-C$_6$)alkyl-S—, (C$_1$-C$_6$)alkyl-S(O)—, (C$_1$-C$_6$)alkyl-SO$_2$—, NH$_2$—SO$_2$—, (C$_1$-C$_6$)alkylNH—SO$_2$— and di((C$_1$-C$_6$)alkyl)N—SO$_2$—, where each of said (C$_1$-C$_6$)alkyl, (C$_2$-C$_6$)alkenyl, and (C$_2$-C$_6$)alkynyl moieties are optionally substituted by one or more substituents each independently selected from halogen, hydroxyl, (C$_1$-C$_6$)alkoxy, amino, (C$_1$-C$_6$)alkyl-NH—, di((C$_1$-C$_6$)alkyl)N— or cyano;

R$^{2a}$ is H or C$_{1-6}$-alkyl;

R$^{2b}$ is a chemical moiety selected from (C$_1$-C$_6$)alkyl, (C$_2$-C$_6$)alkenyl, (C$_2$-C$_6$)alkynyl, NR$^{10}$R$^{12}$, cycloalkyl, aryl, heterocycloalkyl, or heteroaryl, wherein said chemical moiety is optionally substituted by one to three substituents each independently selected from halogen, cyano, hydroxyl, (C$_1$-C$_6$)alkoxy, (C$_2$-C$_6$)alkenyloxy, (C$_2$-C$_6$)alkynyloxy, (C$_1$-C$_6$)alkyl-S—, halo-substituted (C$_1$-C$_6$)alkyl, amino, (C$_1$-C$_6$)alkylNH—, di((C$_1$-C$_6$)alkyl)N—, HC(O)—NH—, (C$_1$-C$_6$)alkyl-C(O)—N—, HC(O)—N(C$_1$-C$_6$)alkyl)-, (C$_1$-C$_6$)alkyl-C(O)—N((C$_1$-C$_6$)alkyl)-, monocyclic cycloalkyl or monocyclic heterocycloalkyl, where said cycloalkyl and said heterocycloalkyl are optionally substituted by one or two substituents each independently selected from halogen, cyano, hydroxyl, (C$_1$-C$_6$)alkoxy, (C$_2$-C$_6$)alkenyloxy, (C$_2$-C$_6$)alkynyloxy, (C$_1$-C$_6$)alkyl-S—, C$_{1-6}$-haloalkyl, amino, (C$_1$-C$_6$)alkylNH—, di((C$_1$-C$_6$)alkyl)N—, HC(O)—NH—, (C$_1$-C$_6$)alkyl-C(O)—NH—, HC(O)—N(C$_1$-C$_6$)alkyl)-, or (C$_1$-C$_6$)alkyl-C(O)—N((C$_1$-C$_6$)alkyl)-;

W is NR$^{22}$, O, or S;

R$^3$ and R$^4$ are each independently H, (C$_1$-C$_6$)alkyl, halo-substituted (C$_1$-C$_6$)alkyl, hydroxy(C$_1$-C$_6$)alkyl, or (C$_1$-C$_6$)alkoxy;

R$^5$ is H, halogen, (C$_1$-C$_3$)alkyl, or halo-substituted (C$_1$-C$_3$)alkyl;

R$^{10}$ and R$^{12}$ are each independently H, or a chemical moiety selected from (C$_1$-C$_6$)alkyl, (C$_2$-C$_6$)alkenyl, (C$_2$-C$_6$)alkynyl, $(C_1-C_6)$alkylC(O)—, $(C_1-C_6)$alkoxy, $(C_3-C_{14})$cycloalkyl, $(C_6-C_{14})$aryl, 4- to 14-membered cycloheteroalkyl, or 5- to 14-membered heteroaryl, wherein each of said chemical moieties are optionally substituted by one or more substituents each independently selected from halogen, hydroxyl, $(C_1-C_6)$alkoxy, amino, $(C_1-C_6)$alkylamino, di-$((C_1-C_6)$alkyl)amino or cyano; and $R^{22}$ is H, or a chemical moiety selected from $(C_1-C_6)$alkyl, $(C_2-C_6)$alkenyl, $(C_2-C_6)$alkynyl, cycloalkyl, aryl, heterocycloalkyl, aryl-$(C_1-C_6)$alkyl-, $(C_1-C_6)$alkyl-aryl-, or diaryl-$(C_1-C_6)$alkyl-, where each of said chemical moieties is optionally substituted by one or more substituents each independently selected from hydroxyl, cyano, nitro, $(C_1-C_6)$alkyl, $(C_2-C_6)$alkenyl, $(C_2-C_6)$alkynyl, $(C_1-C_6)$alkoxy, $(C_2-C_6)$alkenyloxy, $(C_2-C_6)$alkynyloxy, halogen, $(C_1-C_6)$alkyl-C(O)—, —C(O)OH, —C(O)—O($C_1-C_6)$alkyl, amino, $(C_1-C_6)$alkylNH—, di($(C_1-C_6)$-alkyl)N—, $(C_1-C_6)$alkylNH—C(O)—, di($(C_1-C_6)$alkyl)N—C(O)—, $(C_1-C_6)$alkyl-C(O)—NH—, $(C_1-C_6)$alkyl-C(O)—N($(C_1-C_6)$alkyl)-, $(C_1-C_6)$alkyl-$SO_2$—NH—, $(C_1-C_6)$alkyl-$SO_2$—N($(C_1-C_6)$alkyl)-, $(C_1-C_6)$alkyl-S—, $(C_1-C_6)$alkyl-S(O)—, $(C_1-C_6)$alkyl-$SO_2$—, $NH_2$—$SO_2$—, $(C_1-C_6)$alkylNH—$SO_2$— and di($(C_1-C_6)$alkyl)N—$SO_2$—, where each of said $(C_1-C_6)$alkyl, $(C_2-C_6)$alkenyl, and $(C_2-C_6)$alkynyl moieties are optionally substituted by one or more substituents each independently selected from halogen, hydroxyl, $(C_1-C_6)$alkoxy, amino, $(C_1-C_6)$alkyl-NH—, di($(C_1-C_6)$alkyl)N—, or cyano; or a pharmaceutically acceptable salt thereof.

When W is $NR^{22}$, then $R^{22}$ is preferably H, $(C_1-C_6)$alkyl (e.g., methyl, ethyl, or propyl) $(C_2-C_6)$alkenyl (ethenyl), $(C_2-C_6)$alkynyl (e.g., ethynyl), cycloalkyl (e.g., cyclopropyl, cyclobutyl, cyclopentyl, or cyclohexyl) aryl (e.g., phenyl), heterocycloalkyl (e.g., piperazinyl, piperidinyl, tetrahydrofuranyl, or morpholinyl), aryl-$(C_1-C_6)$alkylene (e.g., phenyl-$CH_2$—, phenyl-$CH_2$—$CH_2$—, or phenyl-$CH_2$—$CH_2$—$CH_2$—), $(C_1-C_6)$alkyl-aryl-, (e.g. tolyl), diaryl-$(C_1-C_6)$alkylene (e.g., diphenyl-CH—); wherein said alkyl, alkenyl, alkynyl, cycloalkyl, aryl, heterocycloalkylene, or aryl is optionally substituted by one or more groups each independently selected from List 1. More preferably, $R^{22}$ is H, methyl, ethyl, propyl, cyclopropyl, cyclopentyl, phenyl, benzyl, or phenethyl, wherein said methyl, ethyl, propyl, cyclopropyl, cyclopentyl, phenyl, benzyl, or phenethyl is optionally substituted by one or more groups independently selected from List 1. Even more preferred, $R^{22}$ is H, methyl, ethyl, phenyl, benzyl, or phenethyl, wherein said methyl, ethyl, phenyl, benzyl, or phenethyl is optionally substituted by one or more groups independently selected from List 1. In one embodiment, $R^{22}$ is H or benzyl. Most preferably, $R^{22}$ is H.

Preferably, $R^3$ and $R^4$ are each independently H, methyl, or ethyl. More referably, one of $R^3$ and $R^4$ is H, and the other is methyl. Most preferably, both $R^3$ and $R^4$ are H.

Preferably, $R^5$ is H, halogen (preferably, fluoro or chloro), $(C_1-C_3)$alkyl (preferably, methyl), or halo-substituted $(C_1-C_3)$alkyl (preferably, trifluromethyl). More preferably, $R^5$ is fluoro, chloro, methyl, or trifluoromethyl. Most preferably, $R^5$ is methyl.

In another embodiment, a compound of Formula (IB) is provided

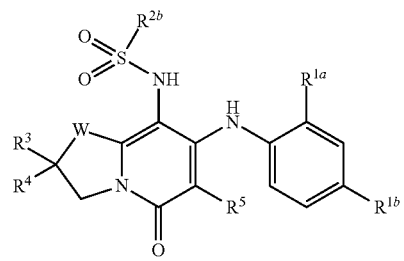

(IB)

wherein $R^{1a}$ and $R^{1b}$ are each independently hydroxyl, cyano, nitro, $(C_1-C_6)$alkyl, $(C_2-C_6)$alkenyl, $(C_2-C_6)$alkynyl, $(C_1-C_6)$alkoxy, halogen, amino, or $(C_1-C_6)$alkyl-NH—, $R^{2b}$ is
(i) 3- to 6-membered cycloalkyl, where said cycloalkyl is optionally substituted with hydroxyl, $(C_1-C_6)$alkyl, $(C_2-C_6)$alkenyl, or $(C_2-C_6)$alkynyl, wherein said $(C_1-C_6)$alkyl, said $(C_2-C_6)$alkenyl, and said $(C_2-C_6)$alkynyl are optionally substituted with 1 to 3 hydroxyl,
(ii) $(C_1-C_6)$alkyl substituted by a monocyclic 3- to 6-membered cycloalkyl or a monocyclic 3- to 6-membered heterocycloalkyl containing 1 to 3 heteroatoms selected from O, S or N, where said substituted alkyl is optionally substituted with one to three substituents each independently selected from the group consisting of halogen, cyano, hydroxyl, $(C_1-C_6)$alkoxy, $(C_1-C_6)$alkyl-S—, halo-substituted $(C_1-C_6)$alkyl, amino, $(C_1-C_6)$alkyl-NH—, di-$((C_1-C_6)$alkyl)-N—, and $(C_1-C_6)$alkylC(O)—NH—,
(iii) $(C_2-C_6)$alkenyl substituted by a monocyclic 3- to 6-membered cycloalkyl or a monocyclic 3- to 6-membered heterocycloalkyl containing 1 to 3 heteroatoms selected from O, S or N, where said substituted alkenyl is optionally substituted with one to three substituents each independently selected from the group consisting of halogen, cyano, hydroxyl, $(C_1-C_6)$alkoxy, $(C_1-C_6)$alkyl-S—, halo-substituted $(C_1-C_6)$alkyl, amino, $(C_1-C_6)$alkyl-NH—, di-$((C_1-C_6)$alkyl)-N—, and $(C_1-C_6)$alkylC(O)—NH—,
(iv) $(C_2-C_6)$alkynyl substituted by a monocyclic 3- to 6-membered cycloalkyl or a monocyclic 3- to 6-membered heterocycloalkyl containing 1 to 3 heteroatoms selected from O, S or N, where said substituted alkynyl is optionally substituted with one to three substituents each independently selected from the group consisting of halogen, cyano, hydroxyl, $(C_1-C_6)$alkoxy, $(C_1-C_6)$alkyl-S—, halo-substituted $(C_1-C_6)$alkyl, amino, $(C_1-C_6)$alkyl-NH—, di-$((C_1-C_6)$alkyl)-N—, and $(C_1-C_6)$alkylC(O)—NH—, or
(v) di($(C_1-C_6)$alkyl)amine;
$R^3$ is H;
$R^4$ is H or methyl;
W is $NR^{22}$, O, or S, where $R^{22}$ is H, methyl, ethyl, phenyl, benzyl, or phenethyl;
$R^5$ is H, halogen, $(C_1-C_3)$alkyl, or halo-substituted $(C_1-C_3)$alkyl;
or a pharmaceutically acceptable salt thereof.

Preferably, $R^{1a}$ and $R^{1b}$ are each independently halogen.

In yet another embodiment, a compound of Formula (IC) is provided

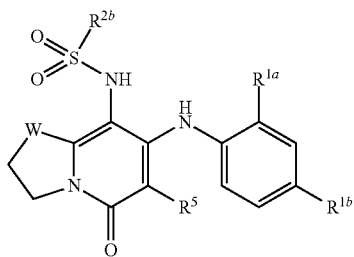

(IC)

wherein
$R^{1a}$ is F;
$R^{1b}$ is Br or I;
$R^{2b}$ is
(i) 3- to 6-membered cycloalkyl, where said cycloalkyl is optionally substituted with hydroxyl, or $(C_1-C_6)$alkyl, wherein said $(C_1-C_6)$alkyl is optionally substituted with 1 to 3 hydroxyl,
(ii) $(C_1-C_6)$alkyl, where said $(C_1-C_6)$alkyl is optionally substituted with oxetanyl or 1 to 3 hydroxyl, or
(iii) —N(CH$_3$)$_2$;
W is O, S or N($R^{22}$), where $R^{22}$ is H or benzyl; and
$R^5$ is H, F, Cl, CH$_3$ or CF$_3$;
or a pharmaceutically acceptable salt thereof.

In one aspect of this embodiment, W is O. In another aspect of this embodiment, W is S. In yet another aspect of this embodiment, W is N($R^{22}$), preferably $R^{22}$ is H.

Suitable representative compounds where W is O include:
Cyclopropanesulfonic acid [7-(2-fluoro-4-iodo-phenylamino)-6-methyl-5-oxo-2,3-dihydro-5H-oxazolo[3,2-a]pyridin-8-yl]-amide;
2-Hydroxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide;
1-(2-Hydroxy-ethyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide;
1-(2,3-Dihydroxy-propyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide;
1-Hydroxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide;
1-(3-Hydroxy-propyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide;
3-Hydroxy-cyclobutanesulfonic acid [7-(2-fluoro-4-iodo-phenylamino)-6-methyl-5-oxo-2,3-dihydro-5H-oxazolo[3,2-a]pyridin-8-yl]-amide;
Cyclobutanesulfonic acid [7-(2-fluoro-4-iodo-phenylamino)-6-methyl-5-oxo-2,3-dihydro-5H-oxazolo[3,2-a]pyridin-8-yl]-amide;
3-(1,3-dihydroxypropan-2-yl)-N-(7-(2-fluoro-4-iodophenylamino)-6-methyl-5-oxo-3,5-dihydro-2H-oxazolo[3,2-a]pyridin-8-yl)cyclobutane-1-sulfonamide;
N-(7-(2-fluoro-4-iodophenylamino)-6-methyl-5-oxo-3,5-dihydro-2H-oxazolo[3,2-a]pyridin-8-yl)-1-(3-methyloxetan-3-yl)methanesulfonamide;
N-(7-(2-fluoro-4-iodophenylamino)-6-methyl-5-oxo-3,5-dihydro-2H-oxazolo[3,2-a]pyridin-8-yl)-2-(oxetan-3-yl)ethanesulfonamide; and
N-(7-(2-fluoro-4-iodophenylamino)-6-methyl-5-oxo-3,5-dihydro-2H-oxazolo[3,2-a]pyridin-8-yl)-4-hydroxy-3-(hydroxymethyl)butane-1-sulfonamide;
or a pharmaceutically acceptable salt thereof.

Suitable representative compounds where W is S include:
Cyclopropanesulfonic acid [7-(2-fluoro-4-iodo-phenylamino)-6-methyl-5-oxo-2,3-dihydro-5H-thiazolo[3,2-a]pyridin-8-yl]-amide;
1-(2,3-Dihydroxy-propyl)-cyclopropanesulfonic acid [7-(2-fluoro-4-iodo-phenylamino)-6-methyl-5-oxo-2,3-dihydro-5H-thiazolo[3,2-a]pyridin-8-yl]-amide;
2-Hydroxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide;
1-Hydroxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide;
N-[7-(2-Fluoro-4-iodo-phenylamino)-6-methyl-5-oxo-2,3-dihydro-5H-thiazolo[3,2-a]pyridin-8-yl]-dimethylaminosulfonamide;
Cyclopentanesulfonic acid [7-(2-fluoro-4-iodo-phenylamino)-6-methyl-5-oxo-2,3-dihydro-5H-thiazolo[3,2-a]pyridin-8-yl]-amide;
3-Hydroxy-cyclobutanesulfonic acid [7-(2-fluoro-4-iodo-phenylamino)-6-methyl-5-oxo-2,3-dihydro-5H-thiazolo[3,2-a]pyridin-8-yl]-amide;
Cyclobutanesulfonic acid [7-(2-fluoro-4-iodo-phenylamino)-6-methyl-5-oxo-2,3-dihydro-5H-thiazolo[3,2-a]pyridin-8-yl]-amide; and
Cyclopropanesulfonic acid [7-(2-fluoro-4-iodo-phenylamino)-5-oxo-2,3-dihydro-5H-thiazolo[3,2-a]pyridin-8-yl]-amide;
or a pharmaceutically acceptable salt thereof.

Suitable representative compounds where W is NH include:
Cyclopropanesulfonic acid [7-(4-bromo-2-fluoro-phenylamino)-6-methyl-5-oxo-1,2,3,5-tetrahydro-imidazo[1,2-a]pyridin-8-yl]-amide;
Cyclopropanesulfonic acid [7-(2-fluoro-4-iodo-phenylamino)-6-methyl-5-oxo-1,2,3,5-tetrahydro-imidazo[1,2-a]pyridin-8-yl]-amide;
1-(2,3-Dihydroxy-propyl)-cyclopropanesulfonic acid [7-(4-bromo-2-fluoro-phenylamino)-6-methyl-5-oxo-1,2,3,5-tetrahydro-imidazo[1,2-a]pyridin-8-yl]-amide;
1-(2,3-Dihydroxy-propyl)-cyclopropanesulfonic acid [7-(2-fluoro-4-iodo-phenylamino)-6-methyl-5-oxo-1,2,3,5-tetrahydro-imidazo[1,2-a]pyridin-8-yl]-amide; and
3-Hydroxy-cyclobutanesulfonic acid [7-(2-fluoro-4-iodo-phenylamino)-6-methyl-5-oxo-1,2,3,5-tetrahydro-imidazo[1,2-a]pyridin-8-yl]-amide;
or a pharmaceutically acceptable salt thereof.

DEFINITIONS

As used herein, the term "alkyl" refers to a hydrocarbon moiety of the general formula $C_nH_{2n+1}$. The alkane group may be straight or branched. For example, the term "$(C_1-C_6)$ alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, alkylamino, dialkylamino, acyl (i.e., alkyl-C(O)—), alkylamido (i.e., alkyl-C(O)—NH—, alkyl-C(O)—N(alkyl)(H)—), alkylthio (i.e., allkyl-S—), alkylsulfinyl (i.e., alkyl-S(O)—), alkylsulfonyl (i.e., alkyl-S(O)$_2$—), alkylsulfamyl (alkyl-NH—SO$_2$—), alkylsulfonamido (alkyl-SO$_2$—NH—), etc. have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls). "Halo-substituted alkyl" refers to an alkyl group having at least one halogen substitution.

The term "alkenyl" refers to an alkyl moiety containing at least one unsaturation in the alkyl group. The alkenyl group may be straight or branched. For example, vinyl, prop-1-enyl, prop-2-enyl, 2-methylprop-2-enyl, 3-methylbut-2-enyl, and the like.

The term "alkylene" refers to an alkyl moiety where the moiety contains two binding sites. The alkylene group may be straight (e.g., —(CH$_2$)—, —(CH$_2$)$_2$—, —(CH$_2$)$_3$—, or branched (e.g., —CH(CH$_3$)—, —C(CH$_3$)$_2$—, —CH$_2$CH (CH$_3$)—, —CH(CH$_3$)—CH$_2$—, —C(CH$_3$)$_2$—CH$_2$—, etc.). Suitable alkylene moieties are the same as those described above for alkyl except with two binding sites instead of just one.

The term "alkenylene" refers to an alkenyl moiety containing two binding sites. For example, —CH$_2$—CH=CH—CH$_2$—. Suitable alkenylene moieties are the same as those described above for alkenyl except with two binding sites instead of just one.

The term "aryl" refers to aromatic moieties having a single (e.g., phenyl) or a fused ring system (e.g., naphthalene, anthracene, phenanthrene, etc.). A typical aryl group is a 6- to 14-membered aromatic carbocyclic ring(s). A fused aromatic ring system may also include a phenyl fused to a partially or fully saturated cycloalkyl. For example, 2,3-dihydroindenyl, 1,2,3,4-tetrahydronaphthalenyl, 1,2-dihydronaphthalenyl, 2,3-dihydronaphthalenyl, 9,10-dihydroanthracenyl, fluorenyl, and the like. A preferred aryl is phenyl.

The term "arylene" refers to a carbocyclic aromatic moiety having two binding sites. Suitable arylenes include those groups described above for an aryl moiety except with two binding sites rather than one. For example, 1,2-phenylene, 1,3-phenylene, 1,4-phenylene, 1,3-naphthylene, 1,4-naphthylene, 1,5-naphthylene, 1,6-naphthylene, 1,7-naphthylene, 2,3-naphthylene, 2,4-napthylene, 2,5-naphthylene, 2,6-naphthylene, 2,7-naphthylene, 3,4-naphthylene, 3,5-naphthylene, 3,6-naphthylene, 3,7-naphthylene, etc. The two binding sites on the fused arylene system may be on the same ring or different rings. A preferred arylene is phenylene.

The term "cycloalkyl" or "partially or fully saturated cycloalkyl" refers to a carbocyclic ring which is fully hydrogenated (e.g., cyclopropyl, cyclobutyl, cyclopentyl, cyclohexyl, cycloheptyl, cyclooctyl, etc.) or partially hydrogenated (e.g., cyclopropenyl, cyclobutenyl, cyclopentyl, cyclopenta-1,3-dienyl, cyclohexenyl, cyclohexa-1,3-dienyl, cyclohexa-1,4-dienyl, etc.). Unless specified otherwise, the carbocyclic ring may be a single ring (as described above), a bicyclic ring (e.g., octahydropentalenyl, bicyclo[1.1.1]pentanyl, bicyclo[2.1.1]hexanyl, bicyclo[2.1.1]hex-2-enyl, bicyclo[2.2.1]hept-2-enyl, bicyclo[2.2.1]heptanyl, bicyclo[2.2.2]octanyl, bicyclo[2.2.2]oct-2-enyl, bicyclo[2.2.2]octa-2,5-dienyl, etc.) or a spiral ring (e.g., spiro[2.2]pentanyl, etc.), and the like.

The term "cycloalkylene" or "partially or fully saturated cycloalkylene" refers to a carbocyclic ring having either no unsaturation in the ring (fully hydrogenated) or at least one unsaturation (partially hydrogenated) without being aromatic and contains two binding sites. Suitable ring systems include those described above for a partially or fully saturated cycloalkyl except having two bind sites instead of one. For example, 1,2-cyclopropyl, 1,2-cycloprop-1-enyl, 1,2-cyclobutyl, 1,3-cyclobutyl, 1,2-cyclobut-1-enyl, 3,4-cyclobut-1-enyl, 3,5-cyclopent-1-enyl, 1,4-cyclopenta-1,3-dienyl, 1,5-cyclopenta-1,3-dienyl, 1,2-cyclopenta-1,3-dienyl, 1,3-cyclopenta-1,3-dienyl, etc. Unless specified otherwise, the carbocyclic ring may be a single ring, a bicyclic ring, or a spiral ring where the two binding sites on the bicyclic ring and spiral ring may be on the same ring or different rings. See, e.g., the illustration below.

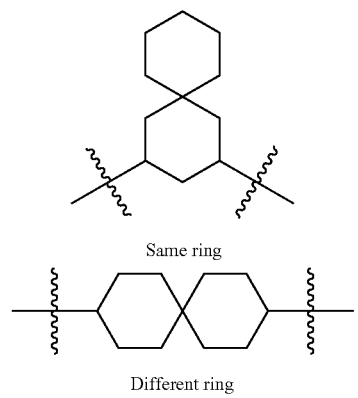

Same ring

Different ring

The term "heterocycle" or "partially or fully saturated heterocycle" refers to a nonaromatic ring that is either partially or fully hydrogenated and may exist as a single ring, bicyclic ring (including fused rings) or a spiral ring. Unless specified otherwise, the heterocyclic ring is generally a 3- to 12-membered ring containing 1 to 3 heteroatoms (preferably 1 or 2 heteroatoms) independently selected from sulfur, oxygen and/or nitrogen. Partially saturated or fully saturated heterocyclic rings include groups such as epoxy, aziridinyl, azetidinyl, tetrahydrofuranyl, dihydrofuranyl, dihydropyridinyl, pyrrolidinyl, imidazolidinyl, imidazolinyl, 1H-dihydroimidazolyl, hexahydropyrimidinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, oxazolidinyl, thiazolidinyl, octahydropyrrolo[3,2-b]pyrrolyl, and the like. A partially saturated heterocyclic ring also includes groups wherein the heterocyclic ring is fused to an aryl or heteroaryl ring (e.g., 2,3-dihydrobenzofuranyl, indolinyl (or 2,3-dihydroindolyl), 2,3-dihydrobenzothiophenyl, 2,3-dihydrobenzothiazolyl, 1,2,3,4-tetrahydroquinolinyl, 1,2,3,4-tetrahydroisoquinolinyl, 5,6,7,8-tetrahydropyrido[3,4-b]pyrazinyl, and the like). Examples of spiral rings include 2,6-diazaspiro[3.3]heptanyl, 3-azaspiro[5.5]undecanyl, 3,9-diazaspiro[5.5]undecanyl, and the like.

The term "heteroaryl" refers to aromatic moieties containing at least one heteroatom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, 1H-benzo[d][1,2,3]triazolyl, and the like.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. The fused heteroaryl ring system may consist of two heteroaryl rings fused together or a hetereoaryl fused to an aryl (generally, phenyl).

The term "heteroarylene" refers to a heteroaryl having two binding sites instead of one. Suitable heteroarylene groups include those described above for heteroaryl having two binding sites instead of one.

Unless specified otherwise, the term "compounds of the present invention" refers to compounds of Formula (IA), (IB) or (IC), and salts thereof, as well as all stereoisomers (including diastereoisomers and enantiomers), tautomers, and isotopically labeled compounds (including deuterium substitutions), as well as inherently formed moieties (e.g., polymorphs, solvates and/or hydrates).

DETAILED DESCRIPTION

The present invention provides compounds and pharmaceutical compositions thereof that are useful in the treatment of diseases, conditions and/or disorders modulated by the inhibition of kinase activity of MEK.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-19, Wiley, New York (1967-1999 ed.), or Beilsteins Handbuch der organischen Chemie, 4, Aufl. ed. Springer-Verlag, Berlin, including supplements (also available via the Beilstein online database)).

The invention provides, in another aspect, a process for preparing a compound of Formula (IA), (IB) and (IC). For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1 below illustrates how one could prepare compounds of the present invention ((1A), (1B), and (IC), where $R^1$ represents the disubstituted phenyl).

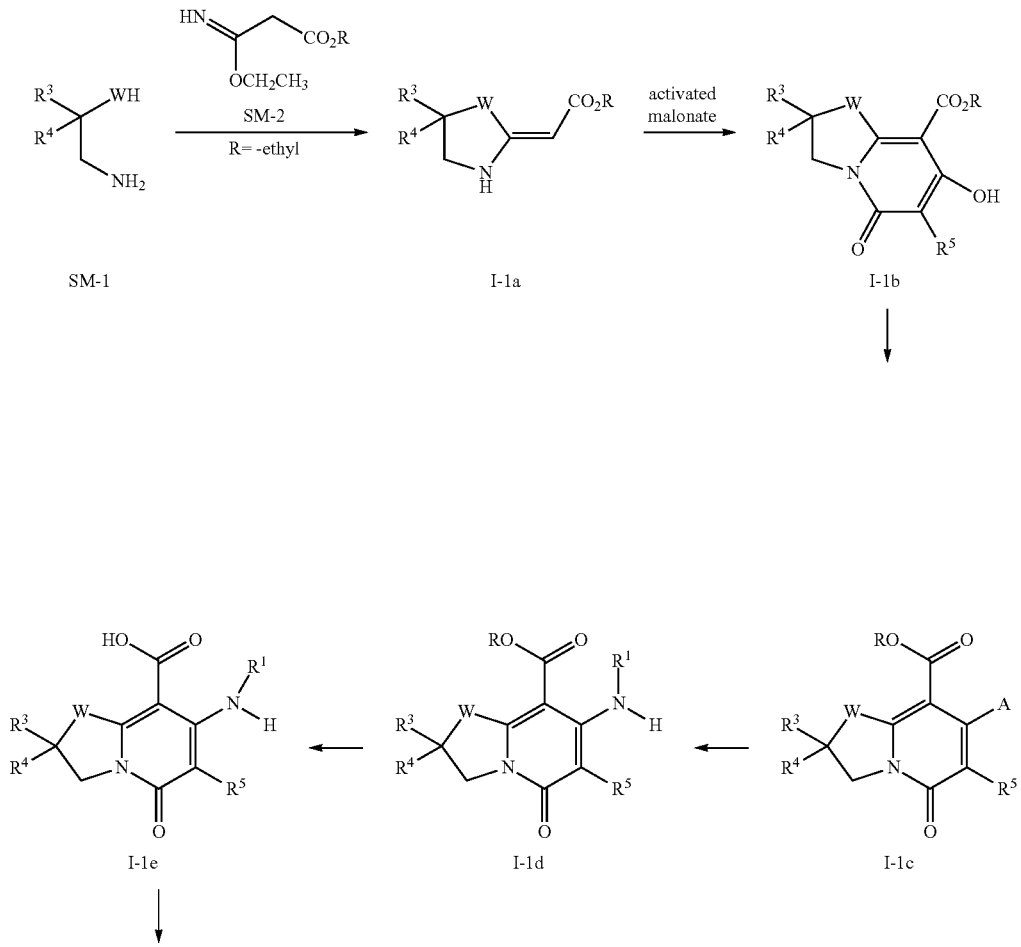

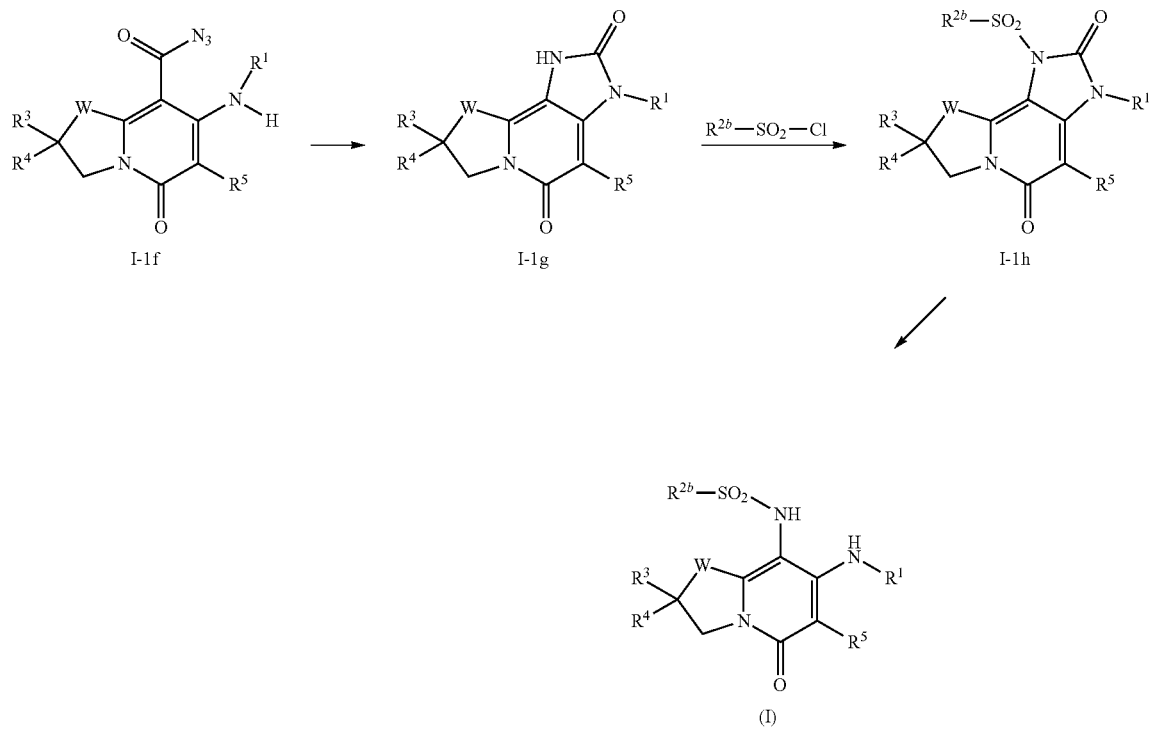

Intermediate (I-1a) can be prepared from the desired amine (SM-1) by refluxing with ethyl ethoxycarbonylethanimidate hydrochloride (SM-2, where R=ethyl) in a suitable protic solvent (e.g., ethanol). The resultant intermediate (I-1a) can then be converted to intermediate (I-1b) by refluxing with an activated malonate (e.g., malonic acid bis-(2,4,6-trichlorophenyl)ester) in a non-protic solvent (e.g., xylene). The leaving group A is then introduced into intermediate (I-1b) to form intermediate (I-1c) by treating intermediate (I-1b) with a halogenating agent (e.g., phosphorus oxybromide) either neat or in a suitable non-protic solvent (e.g., toluene) at temperatures ranging from about room temperature to about 140° C. Alternatively, intermediate (I-1b) may be reacted with nonafluorobutane sulphonyl fluoride in the presence of a suitable base (e.g., diisopropyl ethylamine) and a catalyst (e.g., N,N-dimethyl-4-aminopyridine) in a non-protic solvent (e.g., dichloromethane) at about room temperature, or with N-phenyltrifluoromethanesulfonimide in the presence of a suitable base (e.g., diisopropylethyl amine) in a suitable solvent (e.g., 1,2-dimethoxyethane) at temperatures ranging from about room temperature to the refluxing temperature of the solvent. Alternatively, intermediate (I-1b) may be treated with trifluromethanesulphonic acid anhydride in the presence of base (e.g., pyridine) in a non-protic solvent (dichloromethane) at temperatures ranging from about −20° C. to ambient temperature.

Intermediate (I-1d) may be prepared from intermediate (I-1c) by reacting with an appropriate aniline (R$^{2b}$—NH) using Buchwald-Hartwig C—N coupling conditions. The Buchwald-Hartwig reactions may be performed in presence of a catalyst (e.g., tris(dibenzylidineacetone)dipalladium (0) or palladium acetate), a base (e.g., potassium phosphate, sodium tert-butoxide, 1,8-diazobicyclo-[5.4.1]undec-7-ene or cesium carbonate), and a ligand (e.g., 9,9'-dimethyl-4,5-bis(diphenylphosphino)-xanthene, 2,2'-bis(diphenylphosphino)-1-1'-binaphthyl, 2-dicyclohexylphosphino-2'-(N,N-dimethylamino)biphenyl, 2-dicyclohexylphosphino-2',6'-(dimethoxy)biphenyl or tributylphosphine) in a suitable solvent (e.g., toluene, 1,2-dimethoxyethane, tetrahydrofuran or dioxane) at a temperature ranging from about room temperature to the refluxing temperature of the solvent, or under microwave irradiation at a temperature ranging from about 70° C. to about 150° C. Intermediate (I-1e) can then be prepared from intermediate (I-1d) by reacting with a strong base (e.g., sodium hydroxide) in a protic solvent (e.g., ethanol or methanol) at a temperature ranging from about room temperature to the refluxing temperature of the solvent. Intermediate acyl azide (I-1f) can be prepared from Intermediate (I-1e) via the acid halide (e.g., treatment with an acid chloride using standard conditions) followed by treatment with sodium azide or diphenylphosphoryl azide (DPPA) in the presence of an amine (e.g., triethylamine) in a non-protic solvent (e.g., DMF). Intermediate (I-1f) can then be transformed via the Curtius rearrangement to give intermediate (I-1g).

The R$^{2b}$-sulfonyl group can be introduced into intermediate (I-1g) to form intermediate (I-1h) by treating with the desired sulfonyl chloride (R$^{2b}$—SO$_2$—Cl) in suitable solvent (e.g., dichloromethane) in presence base (e.g., triethyl amine, diisopropyl ethylamine or pyridine). The final compound (I) is then prepared by hydrolyzing intermediate (I-1h). For example, intermediate (I-1h) is heated in the presence of a strong base (e.g., sodium hydroxide) in an aqueous protic solvent (e.g., ethanol/water).

Scheme 2 below provides an alternative procedure for preparing compounds of the present invention ((1A), (1B), and (IC), where R$^1$ represents the disubstituted phenyl).

Scheme 2

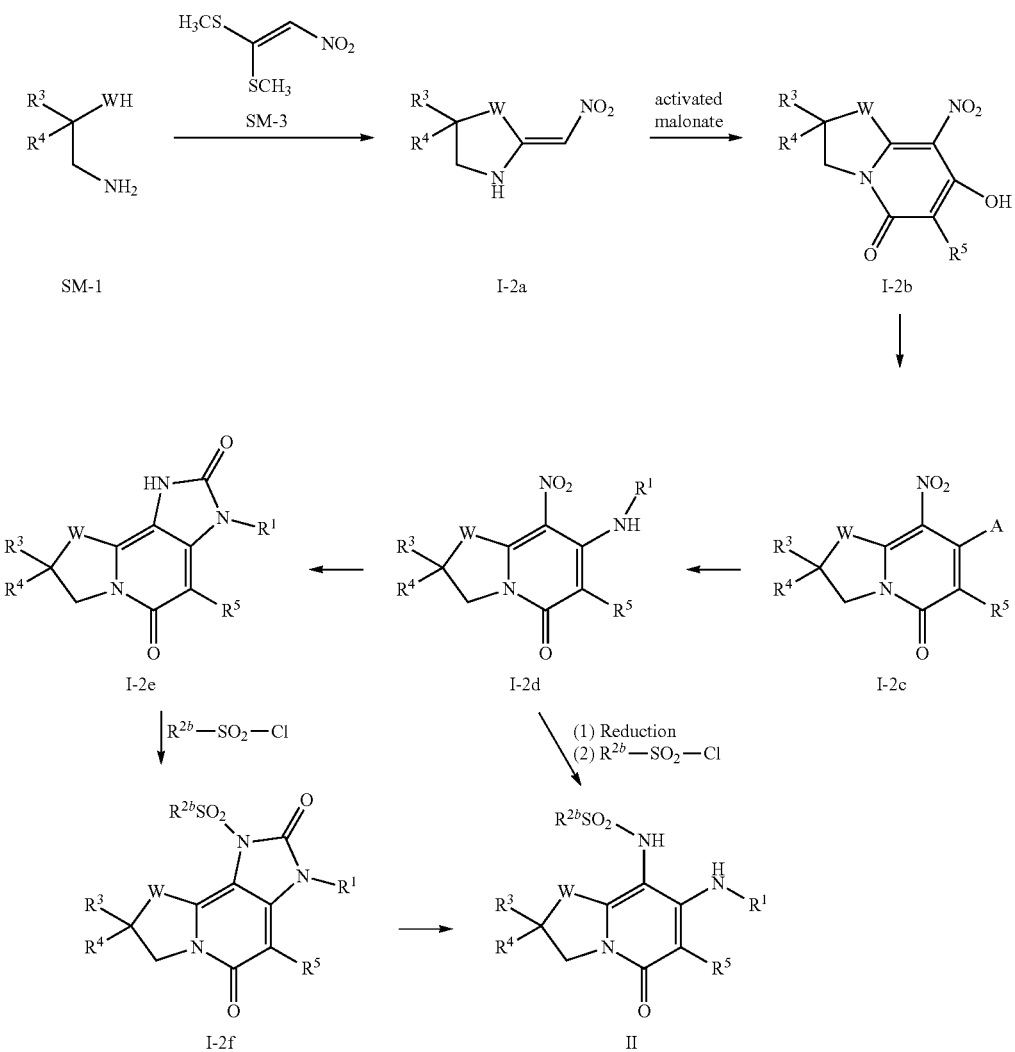

Intermediate (I-2a) can be prepared from the desired amine (SM-1) by treating with equimolar amounts of 1,1-bis(alkylthio)-2-nitroethylene in a polar solvent (e.g., methanol, ethanol, acetonitrile, tetrahydrofuran, water or mixtures thereof) at temperatures up to the reflux temperature of the solvent. A proton acceptor (e.g., NaOH, sodium carbonate or triethylamine) can be used in the reaction. Intermediate (I-2b) can then be prepared using conditions analogous to those described in Scheme I above for the preparation of intermediate (I-1b). Similarly, intermediates (I-2c) and (I-2d) can be prepared using the conditions described above in Scheme I for the preparation of intermediates (I-1c) and (I-1d), respectively. Alternative, intermediate (I-2d) can also be prepared from intermediate (I-2c) using the standard reduction conditions. For example, treatment with Fe/NH$_4$Cl in a solvent (e.g., THF) followed by reaction with triphosgene in non-protic solvent (e.g., DMF).

Intermediate (I-2d) can be converted directly into a compound of the present invention (II) by using standard reduction conditions, well known to those of skill in the art, followed by treating with the desired sulfonyl chloride (R$^{2b}$—SO$_2$—Cl) in a suitable solvent (e.g., dichloromethane) in the presence of a base (e.g., triethyl amine, diisopropyl ethylamine or pyridine).

Alternatively, the nitro group of intermediate (I-2d) can first be reduced to an amino group followed by treatment with N,N'-carbonyldiimidazole (CDI) or triphosgene in the presence of triethylamine (TEA) to produce the imidazolone intermediate (I-2e). Intermediate (I-2e) can then be reacted with the desired sulfonyl chloride (R$^{2b}$—SO$_2$—Cl) in a suitable solvent (e.g., pyridine or DMF) in the presence of a base (e.g., triethyl amine, diisopropyl ethylamine or pyridine) to produce sulfonamide intermediate (I-2f). The final product (II) can then be produced using procedures analogous to those described above in Scheme I. For example, intermediate (I-2f) is heated in the presence of a strong base (e.g., sodium hydroxide) in an aqueous protic solvent (e.g., ethanol/water).

Scheme 3 below illustrates the preparation of compounds of Formula (IA), where X is —N(R$^6$)—, wherein R$^6$ is H (referred to in Scheme 3 as (III)). When R$^3$ and R$^4$ are both H, then Scheme 3 also illustrates how one could prepare compounds of Formula (IB) and (IC).

Scheme 3

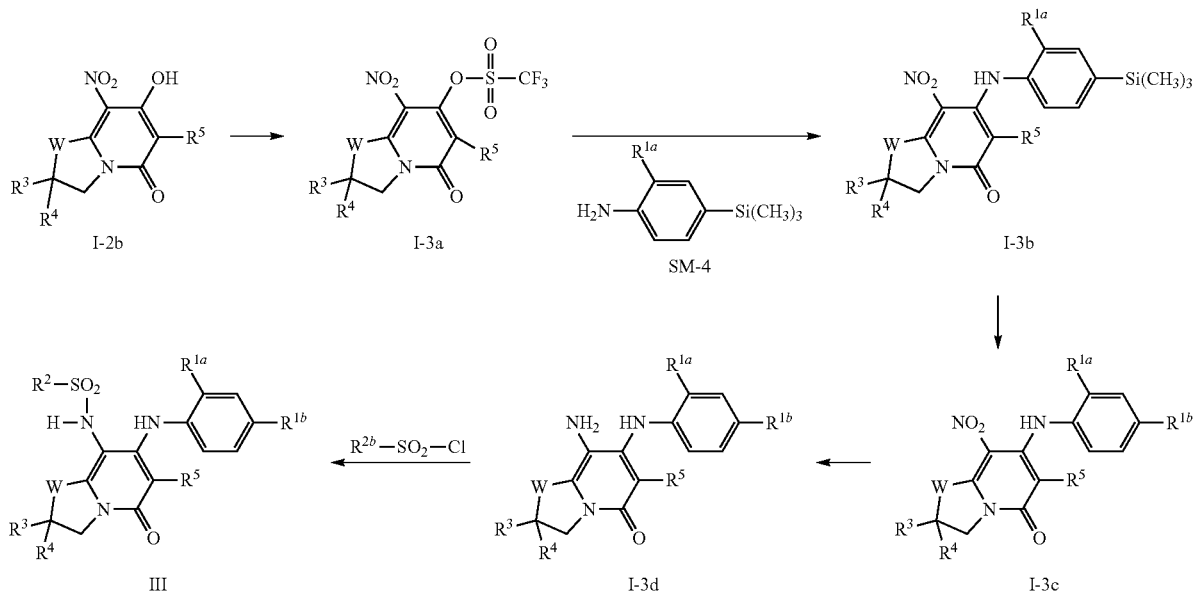

The OH group of intermediate (I-2b) can be converted to a triflic ester by reacting with triflic anhydride in the presence of a base (e.g., triethyl amine). The resultant intermediate (I-3a) can then be reacted with a desired aryl amine (SM-4) using conditions well known to those of skill in the art (e.g., Buchwald-Hartwig conditions) to form intermediate (I-3b). Preferred conditions of the Buchwald-Hartwig reactions include reacting intermediate (I-3a) and the desired amine (SM-4) in the presence of a catalyst (e.g., $Pd(OAc)_2$), a base (e.g., cesium carbonate), and a ligand (e.g., 2,2'-bis(diphenylphosphino)-1,1'-binaphthyl (BINAP)), in the presence of a suitable solvent (e.g., dioxane).

The trimethylsilyl group of Intermediate (I-3b) is then replaced with the desired substituent using procedures well-known to those of skill in the art. For example, the trimethylsilyl group may be substituted by iodide by reacting intermediate (I-3b) with iodine monochloride and silver tetrafluoroborate in dry DCM under an inert atmosphere at reduced temperatures (e.g., about −50° C.) Intermediate (I-3d) can then be prepared from intermediate (I-3c) reducing the nitro group using procedures well-known to those of skill in the art. For example, intermediate (I-3c) can be treated with a reducing agent (e.g., sodium dithionite or stannous chloride) in the presence of an acid (e.g., hydrochloic acid). The final compound (III) can then be prepared using procedures analogous to those described in Schemes 1 and 2. For example, intermediate (I-3d) is reacted with the desired sulfonyl chloride ($R^2$—$SO_2$—Cl) in a suitable solvent (e.g., pyridine or DMF) in the presence of a base (e.g., triethyl amine, diisopropyl ethylamine or pyridine).

The compounds and intermediates described in the schemes above can be isolated per se or as their corresponding salts. For example, many of the compounds represented by Formula (IA), (IB) and (IC) are capable of forming acid addition salts, particularly pharmaceutically acceptable acid addition salts. Pharmaceutically acceptable acid addition salts of the compound of Formula (IA), (IB), or (IC) include those of inorganic acids, for example, hydrohalic acids such as hydrochloric acid, hydrobromic acid or hydroiodic acid, nitric acid, sulfuric acid, phosphoric acid; and organic acids, for example aliphatic monocarboxylic acids such as formic acid, acetic acid, propionic acid and butyric acid, aliphatic hydroxy acids such as lactic acid, citric acid, tartaric acid or malic acid, dicarboxylic acids such as maleic acid or succinic acid, aromatic carboxylic acids such as benzoic acid, p-chlorobenzoic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid. These salts may be prepared from compounds of Formula (IA), (IB), or (IC) by known salt-forming procedures.

Compounds of Formula (IA), (IB), or (IC) which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine. These salts may be prepared from compounds of Formula (IA), (IB), or (IC) by known salt-forming procedures.

It will be recognized by those skilled in the art that the compounds of the present invention may contain chiral centers and as such may exist in different isomeric forms. As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound.

"Enantiomers" are a pair of stereoisomers that are non-superimposable mirror images of each other. A 1:1 mixture of a pair of enantiomers is a "racemic" mixture. The term is used to designate a racemic mixture where appropriate.

"Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-.

Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Compounds of the invention that contain groups capable of acting as donors and/or acceptors for hydrogen bonds may be capable of forming co-crystals with suitable co-crystal formers. These co-crystals may be prepared from compounds of the present invention by known co-crystal forming procedures. Such procedures include grinding, heating, co-subliming, co-melting, or contacting in solution compounds of the present invention with the co-crystal former under crystallization conditions and isolating co-crystals thereby formed. Suitable co-crystal formers include those described in WO 2004/078163. Hence the invention further provides co-crystals comprising a compound of the present invention.

The compounds of the present invention include isotopically-labeled compounds wherein one or more atoms are replaced by atoms having the same atomic number, but an atomic mass or mass number different from the atomic mass or mass number usually found in nature.

Examples of isotopes suitable for inclusion in the compounds of the invention comprises isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Isotopically-labeled compounds of the present invention can generally be prepared by conventional techniques known to those skilled in the art or by processes analogous to those described in the accompanying Examples and Preparations Sections using an appropriate isotopically-labeled reagent in place of the non-labeled reagent previously employed.

The compounds of the present invention may exist in unsolvated as well as solvated forms with pharmaceutically acceptable solvents such as water, ethanol, and the like, and it is intended that the invention embrace both solvated and unsolvated forms. For purposes of the present invention, solvates (including hydrates) are considered pharmaceutical compositions, e.g., a compound of Formula (IA), (IB), or (IC) (or a pharmaceutically acceptable salt thereof) in combination with an excipient, wherein the excipient is a solvent.

The present invention is also in relation to a pharmaceutical composition comprising a compound of the present invention and pharmaceutically acceptable excipients.

Suitable excipients generally include binders, anti-adherents, disintegrants, fillers, diluents, flavors, colorants, glidants, lubricants, preservatives, sorbents and sweeteners or combination(s) thereof.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients. The compound of the present invention is typically formulated into pharmaceutical dosage forms to provide an easily controllable dosage of the drug and to give the patient an elegant and easily handleable product.

The composition is generally formulated into various dosage forms selected from a group comprising tablet, troches, lozenges, aqueous or oily suspensions, ointment, patch, gel, lotion, dentifrice, capsule, emulsion, creams, spray, drops, dispersible powders or granules, emulsion in hard or soft gel capsules, syrups and elixirs.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds of the present invention are useful as both prophylactic and therapeutic treatments for diseases or conditions related to the hyperactivity of MEK, as well as diseases or conditions modulated by the Raf/Ras/Mek pathway.

Thus, as a further aspect, the invention relates to a method for treating a disease or condition related to the hyperactivity of MEK, or a disease or condition modulated by the MEK cascade, comprising administration of an effective therapeutic amount of a compound of Formula (IA), (IB) or (IC), or a pharmaceutically acceptable salt thereof.

As a further aspect, the invention relates to a method for treating proliferative diseases, such as cancer, comprising administration of an effective amount of a compound of the present invention.

Examples of cancers include but are not limited to: angiosarcoma, fibrosarcoma, rhabdomyosarcoma, liposarcoma, myxoma, rhabdomyoma, fibroma, lipoma, teratoma; bronchogenic carcinoma, squamous cell carcinoma, undifferentiated small cell carcinoma, undifferentiated large cell carcinoma, alveolar (bronchiolar) carcinoma, bronchial adenoma, lymphoma, chondromatous hanlartoma, inesothelioma, esophageal squamous cell carcinoma, leiomyosarcoma, leiomyosarcoma, ductal adenocarcinoma, insulinorna, glucagonoma, gastrinoma, vipoma, stomach and small bowel carcinoid tumors, adenocarcinoma, Karposi's sarcoma, leiomyoma, hemangioma, lipoma, neurofibroma, fibroma, tubular adenoma, villous adenoma, hamartoma, Wilm's tumor [nephroblastoma, leukemia, bladder and urethra squamous cell carcinoma, transitional cell carcinoma, adenocarcinoma, seminoma, teratoma, embryonal carcinoma, teratocareinoma, choriocarcinoma, interstitial cell carcinoma, fibroadenoma, adenomatoid tumors, hepatoma (hepatocellular carcinoma), cholangiocarcinoma, hepatoblastoma, hepatocellular adenoma, hemangioma, osteogenic sarcoma (osteosarcoma), malignant fibrous histiocytoma, chondrosarcoma, Ewing's sarcoma, malignant lyinphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors, osteoma, granuloma, xanthoma, osteitis defornians, meningioma, meningiosarcoma, gliomatosis, astrocytoma, medulloblastoma, glioma, ependymoma, germinoma [pinealoma], glioblastoma multiform, oligodendroglioma, schwannoma, retinoblastoma, congenital tumors, spinal cord neurofibroma, meningioma, glioma, endometrial carcinoma, cervical carcinoma, pre-tumor cervical dysplasia, ovarian carcinoma, serous cystadenocarcinoma, mucinous cystadenocarcinoma, granulosa-thecal cell tumors, Sertoli-Leydig cell tumors, dysgerminoma, malignant teratoma, intraepithelial carcinoma, adenocarcinoma, melanoma), vaginal clear cell carcinoma, botryoid sarcoma (embryonal rhabdomyosarcoma), fallopian tube carcinoma, acute and chronic myeloid leukemia, acute lymphoblastic leukemia, chronic lymphocytic leukemia, myeloproliferative diseases, multiple myeloma, myelodysplastic syndrome, Hodgkin's disease, non-Hodgkin's lymphoma, malignant lymphoma, malignant melanoma, basal cell carcinoma, moles, dysplastic nevi, angioma, dermatofibroma, keloids, psoriasis, and neuroblastoma.

The compounds of the present invention may also be useful in the treatment of other diseases or conditions related to the hyperactivity of MEK. Thus, as a further aspect, the invention relates to a method of treatment of a disorder selected from: xenograft (cellos), skin, limb, organ or bone marrow transplant) rejection; osteoarthritis; rheumatoid arthritis; cystic fibrosis; complications of diabetes (including diabetic retinopathy and diabetic nephropathy); hepatomegaly; cardiomegaly; stroke (such as acute focal ischemic stroke and global cerebral ischemia); heart failure; septic shock; asthma; chronic obstructive pulmonary disorder; Alzheimer's disease; and chronic or neuropathic pain.

The term "chronic pain" for purposes of the present invention includes, but is not limited to, idiopathic pain, and pain associated with chronic alcoholism, vitamin deficiency, uremia, or hypothyroidism. Chronic pain is associated with numerous conditions including, but not limited to, inflammation, and post-operative pain.

As used herein, the term "neuropathic pain" is associated with numerous conditions which include, but are not limited to, inflammation, postoperative pain, phantom limb pain, burn pain, gout, trigeminal neuralgia, acute herpetic and postherpetic pain, causalgia, diabetic neuropathy, plexus avulsion, neuroma, vasculitis, viral infection, crush injury, constriction injury, tissue injury, limb amputation, and nerve injury between the peripheral nervous system and the central nervous system.

Compounds of the invention may also be useful as antiviral agents for treating viral infections such as HIV, hepatitis (B) virus (HBV) human papilloma virus (HPV), cytomegalovirus (CMV], and Epstein-Barr virus (EBV).

Compounds of the invention may also be useful in the treatment of restenosis, psoriasis, allergic contact dermatitis, autoimmune disease, atherosclerosis and inflammatory bowel diseases, e.g. Crohn's disease and ulcerative colitis.

In certain instances, it may be advantageous to administer the compound of the present invention in combination with at least one additional pharmaceutical (or therapeutic) agent (e.g., an anti-cancer agent or adjunct therapy typically used in chemotherapy). The compound of the present invention may be administered either simultaneously with, or before or after, one or more other therapeutic agent(s). Alternatively, the compound of the present invention may be administered separately, by the same or different route of administration, or together in the same pharmaceutical composition as the other agent(s).

For example, a compound of the present invention may be administered simultaneously, sequentially or separately in combination with one or more agents selected from chemotherapy agents, e.g. mitotic inhibitors such as a Docetaxel (sold under the tradename Taxotere® by Sanofi-Aventis), taxane, a vinca alkaloid, paclitaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy.

A compound of the present invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors, such as LBH589; compounds which induce cell differentiation processes; cyclooxygenase inhibitors; MMP inhibitors; mTOR inhibitors, such as RAD001; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3, such as PKC412; Hsp90 inhibitors such as 17-AAG (17-allylamino-gelda-namycin, NSC330507), 17-DMAG (17-dimethylami-noethylamino-17-demethoxy-geldana-mycin, NSC707545), IPI-504, CNF1010, CNF2024, CNF1010 from Conforma Therapeutics and AUY922; temozolomide (TEMODAL); kinesin spindle protein inhibitors, such as SB715992 or SB743921 from GlaxoSmithKline, or pentamidine/chlorpromazine from CombinatoRx; PI3K inhibitors, such as BEZ235; RAF inhibitors, such as RAF265; EDG binders, antileukemia compounds, ribonucleotide reductase inhibitors, S-adenosylmethionine decarboxylase inhibitors, antiproliferative anti-bodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atame-stane, exemestane and formestane and, in part-icular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. un-der the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Amino glutethimide can be administered, e.g., in the form as it is marketed, e.g. under the trademark, ORIMETEN. A combination of the invention comprising a chemo-therapeutic agent which is an aromatase inhibitor is particularly useful for the treatment of hormone receptor positive tumors, e.g., breast tumors.

The term "anti-estrogen" as used herein relates to a compound which antagonizes the ef-fect of estrogens at the estrogen receptor level. The term includes, but is not limited to tamoxifen, fulvestrant, raloxifene and raloxifene hydrochloride. Tamoxifen can be administered, e.g., in the form as it is marketed, e.g. under the trademark NOLVADEX. Raloxifene hydrochloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an anti-estrogen is particularly useful for the treatment of estrogen receptor positive tumors, e.g. breast tumors.

The term "anti-androgen" as used herein relates to any substance which is capable of in-hibiting the biological effects of androgenic hormones and includes, but is not limited to, Nilutamide (sold under the tradenames Nilandron® and Anandron®), flutamide (sold under the tradename Fulexin™), bicalutamide (CASODEX), which can be formulated, e.g. as disclosed in U.S. Pat. No. 4,636,505.

The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecin and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the an-thracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL. Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g., in the form as it is marketed, e.g. under the trademark CYCLOSTIN. Ifosfamide can be administered, e.g., in the form as it is marketed, e.g., under the trademark HOLOXAN. The term "histone deacetylase inhibitors" or "HDAC inhibitors" relates to compounds which inhibit the histone deacetylase and which possess antiproliferative activity. This includes compounds such as sodium butyrate, LDH589 disclosed in WO 02/22577, especially N-hydroxy-3-[4-[[(2-hydroxyethyl)[2-(1H-indol-3-yl)ethyl]-amino]methyl]phenyl]-2E-2-propenamide, N-hydroxy-3-[4-[[[2-(2-methyl-1H-indol-3-yl)-ethyl]-amino]methyl]phenyl]-2E-2-propenamide and pharmaceutically acceptable salts thereof, especially the lactate salt. It further especially includes suberoylanilide hydroxamic acid (SAHA), MS275, FK228 (formerly FR901228), trichostatin A and compounds disclosed in U.S. Pat. No. 6,552,065, in particular, N-hydroxy-3-[4-[[[2-(2-methyl-1H-indol-3-yl)-ethyl]-amino]-methyl]phenyl]-2E-2-propenamide, or a pharmaceutically acceptable salt thereof.

The term "antineoplastic antimetabolite" includes, but is not limited to, 5-Fluorouracil or 5-FU, capecitabine, gemcitabine, DNA demethylating compounds, such as 5-azacy-tidine and decitabine, methotrexate and edatrexate, and folic acid antagonists such as pemetrexed. Capecitabine can be administe-red, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cis-platin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;

b) compounds targeting, decreasing or inhibiting the activity of the fibroblast growth factor-receptors (FGFR);

c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;

d) compounds targeting, decreasing or inhibiting the activity of the Trk receptor tyrosine kinase family, or ephrin B4 inhibitors;

e) compounds targeting, decreasing or inhibiting the activity of the Axl receptor tyrosine kinase family;

f) compounds targeting, decreasing or inhibiting the activity of the Ret receptor tyrosine kinase;

g) compounds targeting, decreasing or inhibiting the activity of the Kit/SCFR receptor tyrosine kinase, i.e C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;

h) compounds targeting, decreasing or inhibiting the activity of members of the c-Abl family, their gene-fusion products (e.g. BCR-Abl kinase) and mutants, such as com-pounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)

i) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; BEZ235 (a P13K inhibitor) or AT7519 (CDK inhibitor);

j) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (mw<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);

k) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin), cetuximab (Erbitux), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d]pyrimidine derivatives which are disclosed in WO 03/013541; and l) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

Compounds which target, decrease or inhibit the activity of a protein or lipid phosphatase are e.g., inhibitors of phosphatase 1, phosphatase 2A, or CDC25, e.g. okadaic acid or a derivative thereof.

Compounds which induce cell differentiation processes are e.g. retinoic acid, or tocopherol or tocotrienol.

The term cyclooxygenase inhibitor as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune), everolimus (CerticanO), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons, e.g. interferon.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra).

The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, TKI258, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds, and radicicol.

The term "antiproliferative antibodies" as used herein includes, but is not limited to, trastuzumab (Herceptin), Trastuzumab-DM1, erbitux, bevacizumab (Avastin), rituximab (Rituxan), PRO64553 (anti-CD40) and 2C4 Antibody. By antibodies is meant e.g. intact monoclonal antibodies, polyclonal antibodies, multispe-cific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2-alpha-hydroxy ribose (arabinoside) derivative of deoxycytidine. Also included is the purine analog of hypoxanthine, 6-mercaptopurine (6-MP) and fludarabine phosphate.

Somatostatin receptor antagonists as used herein refers to compounds which target, treat or inhibit the somatostatin receptor such as octreotide, and SOM230 (pasireotide).

Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4th Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., Acta Oncologica, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, Cancer Res, Vol. 59, pp. 5209-5218 (1999); Yuan et al., Proc Natl Acad Sci USA, Vol. 93, pp. 14765-14770 (1996); Zhu et al., Cancer Res, Vol. 58, pp. 3209-3214 (1998); and Mordenti et al., Toxicol Pathol, Vol. 27, No. 1, pp. 14-21 (1999); in WO 00/37502 and WO 94/10202; ANGIOSTATIN, described by O'Reilly et al., Cell, Vol. 79, pp. 315-328 (1994); ENDOSTATIN, described by O'Reilly et al., Cell, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin).

Photodynamic therapy as used herein refers to therapy which uses certain chemicals known as photosensitizing compounds to treat or prevent cancers. Examples of photodynamic therapy includes treatment with compounds, such as e.g. VISUDYNE and porfimer sodium.

Angiostatic steroids as used herein refers to compounds which block or inhibit angiogenesis, such as, e.g., anecortave, triamcinolone, hydrocortisone, 11-epihydrocotisol, cortexolone, 17-hydroxyprogesterone, corticosterone, desoxycorticosterone, testosterone, estrone and dexamethasone.

Implants containing corticosteroids refers to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code nos., generic or trade names may be taken from the actual edition of the standard compendium "The Merck Index" or from databases, e.g. Patents International (e.g. IMS World Publications).

None of the quotations of references made within the present disclosure is to be understood as an admission that the references cited are prior art that would negatively affect the patentability of the present invention.

The compounds of the invention may also be administered simultaneously, separately or sequentially in combination with one or more other suitable active agents selected from the following classes of agents: Anti IL-1 agents, e.g: Anakinra; anti cytokine and anti-cytokine receptor agents, e.g. anti IL-6 R Ab, anti IL-15 Ab, anti IL-17 Ab, anti IL-12 Ab; B-cell and T-cell modulating drugs, e.g. anti CD20 Ab; CTL4-Ig, disease-modifying anti-rheumatic agents (DMARDs), e.g. methotrexate, leflunamide, sulfasalazine; gold salts, penicillamine, hydroxychloroquine and chloroquine, azathioprine, glucocorticoids and non-steroidal anti-inflammatories (NSAIDs), e.g. cyclooxygenase inhibitors, selective COX-2 inhibitors, agents which modulate migration of immune cells, e.g. chemokine receptor antagonists, modulators of adhesion molecules, e.g. inhibitors of LFA-1, VLA-4.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. In general, suitable daily dosages for oral administration are from about 0.1 to about 10 mg/kg. However, it will be understood by those of skill in the art that the therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

In general, a therapeutically effective amount of a compound of the present invention is administered to a patient in need of treatment. The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc.

In yet another embodiment, a method for treating cancer in a mammal is provided which comprises administering to a mammal in need of such treatment an effective amount of a compound of the present invention.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. Preferably, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder, refers (i) to ameliorating the disease or disorder (i.e., slowing or arresting or reducing the development of the disease or at least one of the clinical symptoms thereof); (ii) to alleviating or ameliorating at least one physical parameter including those which may not be discernible by the patient; or (iii) to preventing or delaying the onset or development or progression of the disease or disorder. In general, the term "treating" or "treatment" describes the management and care of a patient for the purpose of combating the disease, condition, or disorder and includes the administration of a compound of the present invention to prevent the onset of the symptoms or complications, alleviating the symptoms or complications, or eliminating the disease, condition or disorder.

As used herein, a subject is "in need of" a treatment if such subject would benefit biologically, medically or in quality of life from such treatment (preferably, a human).

Another aspect of the invention is a product comprising a compound of the present invention and at least one other therapeutic agent (or pharmaceutical agent) as a combined preparation for simultaneous, separate or sequential use in therapy to enhance apoptosis.

In the combination therapies of the invention, the compound of the present invention and the other therapeutic agent may be manufactured and/or formulated by the same or different manufacturers. Moreover, the compound of the present invention and the other therapeutic (or pharmaceutical agent) may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of the present invention for treating a disease or condition by inhibiting the MAP kinase pathway, wherein the medicament is prepared for administration with another therapeutic agent. The invention also provides for the use of another therapeutic agent, wherein the medicament is administered as a combination of a compound of the present invention with the other therapeutic agent.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

The following abbreviations used herein below have the corresponding meanings:
BINAP: 2,2'-bis(diphenylphosphino)-1,1'-binaphthyl
ByBOP: benzotriazol-1-yl-oxytripyrrolidinophosphonium hexafluorophosphate
DCM: dichloromethane
DMF: N,N-dimethylformamide
EDCI: 1-ethyl-3-(3'-dimethylaminopropyl)carbodiimide
HOBT: N-hydroxybenzotriazole
KHMDS: potassium bis(trimethylsilyl)amide
LDA: lithium diisopropylamide
LiHMDS: lithium bis(trimethylsilyl)amide
NaHMDS: sodium bis(trimethylsilyl)amide
NBS: N-bromosuccinamide
NCS: N-chlorosuccinimide
NIS: N-iodosuccinimide
TBTU: O-(benzotriazol-1-yl)-N,N,N',N'-tetramethyluronium tetrafluoroborate
TEA: triethyl amine
THF: tetrahydrofuran
TMS: trimethylsilyl
Xantphos: 4,5-Bis(diphenylphosphino)-9,9-dimethylxanthene
HPLC: high pressure liquid chromatography or high performance liquid chromatography
LC-MS: liquid chromatography-mass spectrometry
NMR: nuclear magnetic resonance
TLC: thin layer chromatography Example 1

Synthesis of Cyclopropanesulfonic acid [1-benzyl-7-(4-bromo-2-fluoro-phenylamino)-6-methyl-5-oxo-1,2,3,5-tetrahydro-imidazo[1,2-a]pyridin-8-yl]-amide (1A)

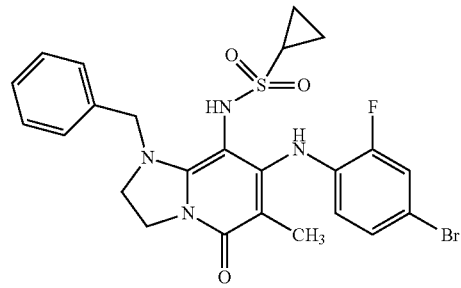

(1A)

Synthesis of Intermediate Potassium salt of 2-Nitro-ethene-1,1-dithiol (I-1a)

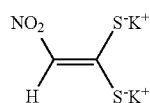

Ethanolic KOH (148 g, 2.64 mol) was added to a solution of carbon disulphide (200 g, 2.63 mol) and nitromethane (161 g, 2.63 mol) at 0° C. The resulting mixture was stirred at 0° C. for 1 hour and at room temperature for 1 hour. The reaction mixture was filtered, washed with ethanol (500 mL) and dried under reduced pressure to afford 400 g of the product (71.5% yield).

Synthesis of Intermediate 1,1-Bis-methylsulfanyl-2-nitro-ethene (I-1b)

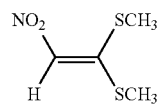

Methyl iodide (227 g, 1.598 mol) was added to a solution of potassium salt of 2-nitro-ethene-1,1-dithiol (150 g, 0.704 mol) in DMF (800 mL) at 0° C. under nitrogen atmosphere. The resulting mixture was stirred at room temperature overnight. The reaction was monitored by TLC (30% ethylacetate in hexane). The reaction mixture was quenched with ice water; the precipitate formed was collected and dried to afford 90 g of the product (77.5% yield).

Synthesis of Intermediate 1-Benzyl-2-nitromethylene-imidazolidine (I-1c)

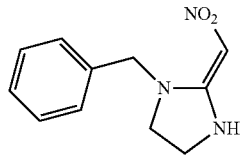 [SMILES: O=[N+]([O-])/C=C1/NCCN1Cc1ccccc1]

Ethanol (200 mL) was added to a solution of 1,1-bis-methylsulfanyl-2-nitro-ethene (14.5 g, 0.0878 mol) and N1-benzyl-ethane-1,2-diamine (12 g, 0.080 mol). The resulting mixture was heated to reflux for 2 hours. The reaction mixture was monitored by TLC (10% MeOH in $CHCl_3$). The reaction mixture was concentrated and the concentrate was dissolved in ethylacetate. The precipitate formed was collected and washed with ethylacetate to afford 13 g of the product (74.7% yield).

$^1H$ NMR (DMSO-$D_6$, 300 MHz) δ: 8.9 (br s, 1H), 7.5-7.2 (m, 5H), 6.6 (s, 1H), 4.5 (s, 2H), 3.7-3.5 (m, 4H).

Synthesis of Intermediate 1-Benzyl-7-hydroxy-6-methyl-8-nitro-2,3-dihydro-1H-imidazo[1,2-a]pyridin-5-one (I-1d)

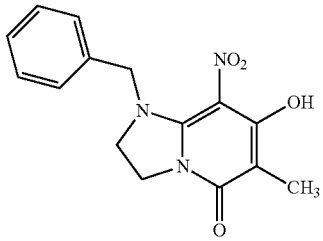 [SMILES: Cc1c(O)c([N+](=O)[O-])c2n(c1=O)CCN2Cc1ccccc1]

Xylene (15 mL) was added to a solution of 1-benzyl-2-nitromethylene-dazolidine (1 g, 0.005 mol) and 2-methyl-malonic acid bis-(2,4,6-trichloro-phenyl)ester (2.39 g, 0.005 mol). The resulting mixture was heated to reflux for 2 hours. The reaction mixture was monitored by TLC (5% MeOH in $CHCl_3$). The reaction mixture was concentrated and the concentrate was dissolved in ethanol. The precipitate formed was collected and washed with ethanol to afford 900 mg of the product (65.69% yield).

$^1H$ NMR ($CDCl_3$, 300 MHz) δ: 11.5 (br s, 1H), 7.4-7.2 (m, 5H), 4.6 (s, 2H), 4.2-4.0 (m, 2H), 4.0-3.8 (m, 2H), 1.9 (s, 3H).

Synthesis of Intermediate Trifluoro-methanesulfonic acid 1-benzyl-6-methyl-8-nitro-5-oxo-1,2,3,5-tetrahydro-imidazo[1,2-a]pyridin-7-yl ester (I-1e)

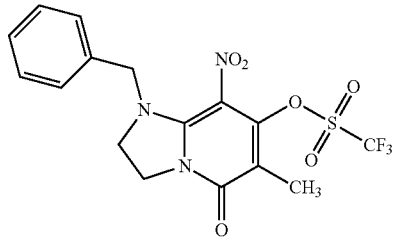 [SMILES: Cc1c(OS(=O)(=O)C(F)(F)F)c([N+](=O)[O-])c2n(c1=O)CCN2Cc1ccccc1]

Triflic anhydride (2.8 g, 0.010 mol) was added to a stirred solution of 1-benzyl-7-hydroxy-6-methyl-8-nitro-2,3-dihydro-1H-imidazo[1,2-a]pyridin-5-one (2 g, 0.007 mol) and TEA (1.34 g, 0.013 mol) in DCM (40 mL) at −78° C. The resulting mixture was stirred at room temperature for 4 hours. The reaction mixture was monitored by TLC (100% ethyl acetate). The reaction mixture was partitioned between DCM and water. The organic layer was washed with $NaHCO_3$ solution, brine solution, dried over $Na_2SO_4$ and concentrated. Purification by column chromatography on silica gel (30% ethylacetate in hexane) afforded 2.5 g of the product (89% yield).

$^1H$ NMR ($CDCl_3$, 300 MHz) δ: 7.4-7.32 (m, 3H), 7.27-7.2 (m, 2H), 4.6 (s, 2H), 4.23-4.13 (t, 2H), 3.91-3.8 (t, 2H), 2.1 (s, 3H)

Synthesis of Intermediate 1-Benzyl-7-(4-bromo-2-fluoro-phenylamino)-6-methyl-8-nitro-2,3-dihydro-1H-imidazo[1,2-a]pyridin-5-one (I-1f)

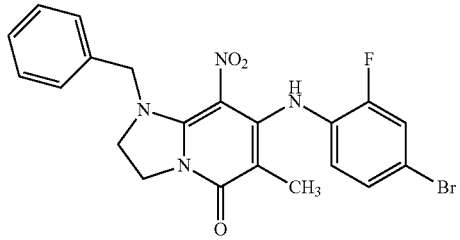

Palladium acetate (129 mg, 0.001 mol), BINAP (538 mg, 0.001 mol), cesium carbonate (2.8 g, 0.009 mol) were dissolved in toluene (20 mL) and the resulting mixture was sparged for 30 mins with nitrogen. This was followed by addition of trifluoro-methanesulfonic acid 1-benzyl-6-methyl-8-nitro-5-oxo-1,2,3,5-tetrahydro-imidazo[1,2-a]pyridin-7-yl ester (2.5 g, 0.006 mol) and 4-bromo-2-fluoro-phenylamine (1.15 g, 0.006 mol) in toluene (20 mL) and the reaction flask was again sparged for another 15 minutes. The reaction mixture was heated at 90° C. for 1 hour. The reaction was monitored by TLC (80% ethylacetate in hexane). The reaction mixture was filtered through celite bed and concentrated. Purification by column chromatography on silica gel (40% ethylacetate in hexane) afforded 1.3 g of the product (48% yield).

$^1H$ NMR (DMSO-$D_6$, 300 MHz) δ: 8.05 (br s, 1H), 7.5 (dd, 1H), 7.4-7.25 (m, 5H), 7.21-7.15 (d, 1H), 6.6 (t, 1H), 4.5 (s, 2H), 4.15 (t, 2H), 3.9 (t, 2H), 1.6 (s, 3H).

Synthesis of Intermediate 8-Amino-1-benzyl-7-(4-bromo-2-fluoro-phenylamino)-6-methyl-2,3-dihydro-1H-imidazo[1,2-a]pyridin-5-one (I-1g)

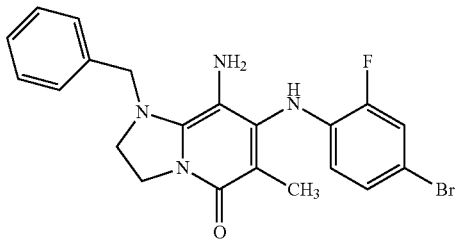 [SMILES: Cc1c(Nc2ccc(Br)cc2F)c([N+](=O)[O-])c2n(c1=O)CCN2Cc1ccccc1]

Zinc (414 mg, 0.006 mol) was added to a stirred solution of 1-benzyl-7-(4-bromo-2-fluoro-phenylamino)-6-methyl-8-nitro-2,3-dihydro-1H-imidazo[1,2-a]pyridin-5-one (500 mg, 0.001 mol) in THF (50 mL) and concentrated HCl (1 mL). The resulting mixture was stirred at room temperature for 30 minutes. The reaction mixture was monitored by TLC (100% ethylacetate). The reaction mixture was concentrated and partitioned between ethylacetate and water. The organic layer was washed with saturated NaHCO$_3$ solution and concentrated to afford 400 mg of the crude product which was used in the next step without further purification.

Synthesis of the Title Compound; Cyclopropanesulfonic acid [1-benzyl-7-(4-bromo-2-fluoro-phenylamino)-6-methyl-5-oxo-1,2,3,5-tetrahydro-imidazo[1,2-a]pyridin-8-yl]-amide (1A)

Cyclopropanesulfonyl chloride (254 mg, 0.0002 mol) was added to a stirred solution of 8-amino-1-benzyl-7-(4-bromo-2-fluoro-phenylamino)-6-methyl-2,3-dihydro-1H-imidazo[1,2-a]pyridin-5-one (400 mg, 0.001 mol) in pyridine (4 mL). The resulting mixture was stirred at room temperature for 3 hours. The reaction mixture was monitored by TLC (100% ethylacetate). The reaction mixture was concentrated and partitioned between ethylacetate and water. The organic layer was concentrated to afford the crude product. Purification by column chromatography on silica gel (80% ethylacetate in hexane), followed by preparative HPLC afforded 30 mg of the product (6% yield).

$^1$H NMR (DMSO-D$_6$, 300 MHz) δ: 8.4-8.35 (br s, 1H), 7.5 (dd, 1H), 7.4-7.25 (m, 5H), 7.2 (d, 1H), 6.5 (t, 1H), 5.0 (d, 1H), 4.8 (d, 1H), 4.1-4.0 (m, 1H), 3.9 (d, 1H), 3.6-3.5 (m, 1H), 2.3 (d, 1H), 1.6 (s, 3H), 1.3 (s, 1H), 0.9-0.7 (m, 4H), 0.5-0.4 (m, 1H). LCMS: 98.98%, m/z=547(M+1) HPLC: 97.95%

Example 2

Synthesis of Cyclopropanesulfonic acid [7-(4-bromo-2-fluoro-phenylamino)-6-methyl-5-oxo-1,2,3,5-tetrahydro-imidazo[1,2-a]pyridin-8-yl]-amide (2A)

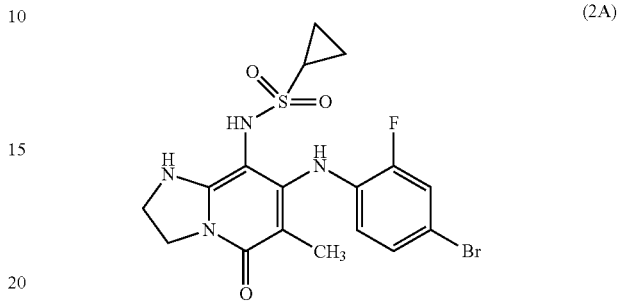

(2A)

Borontribromide (20 mg, 0.0001 mol) was added to a stirred solution of cyclopropanesulfonic acid [1-benzyl-7-(4-bromo-2-fluoro-phenylamino)-6-methyl-5-oxo-1,2,3,5-tetrahydro-imidazo[1,2-a]pyridin-8-yl]-amide (1A: 30 mg, 0.0001 mol) in DCM (3 mL) at 0° C. The resulting mixture was stirred at room temperature for 2 hours. The reaction mixture was monitored by TLC (100% ethylacetate). The reaction mixture was quenched with methanol and concentrated. The concentrate was partitioned between ethyl acetate and water. The organic layer was concentrated to afford the crude product. Purification by column chromatography on silica gel (4% methanol in DCM) afforded 7 mg of the product (28% yield).

$^1$H NMR (DMSO-D$_6$, 300 MHz) δ: 7.2 (d, 1H), 7.1 (d, 1H), 6.5-6.4 (m, 2H), 5.9-5.8 (m, 1H), 5.7-5.6 (br s, 1H), 4.95 (d, 1H), 4.3 (t, 2H), 3.8 (t, 2H), 2.45-2.35 (m, 1H), 2.05-2.0 (d, 2H), 1.8 (s, 3H), 1.12 (d, 3H). LCMS: 74.36%, m/z=457(M+1) HPLC: 97.7%

Example 3

Synthesis of Cyclopropanesulfonic acid [7-(2-fluoro-4-iodo-phenylamino)-6-methyl-5-oxo-1,2,3,5-tetrahydro-imidazo[1,2-a]pyridin-8-yl]-amide (3A)

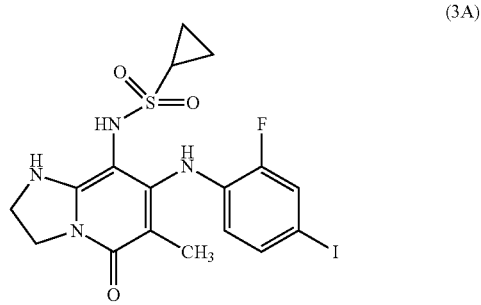 [SMILES: Cc1c(Nc2ccc(I)cc2F)c(NS(=O)(=O)C2CC2)c2n(c1=O)CCN2]

(3A)

Synthesis of Intermediate 1-Benzyl-7-(2-fluoro-4-trimethylsilanyl-phenylamino)-6-methyl-8-nitro-2,3-dihydro-1H-imidazo[1,2-a]pyridin-5-one (I-3a)

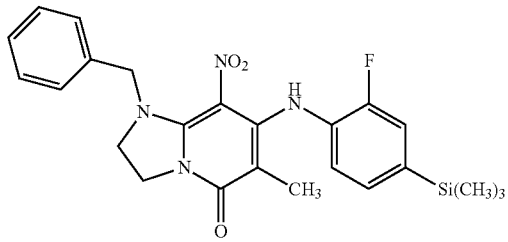

Trifluoro-methanesulfonic acid 1-benzyl-6-methyl-8-nitro-5-oxo-1,2,3,5-tetrahydro-imidazo[1,2-a]pyridin-7-yl ester (I-1e: 500 mg, 0.001 mol) in toluene (15 mL) was reacted with 2-fluoro-4-trimethylsilanyl-phenylamine (221 mg, 0.001 mol) in the presence of $Pd_2(dba)_3$ (63.3 mg, 0.0001 mol), xantphos (40 mg, 0.0001 mol) and $K_3PO_4$ (367 mg, 0.002 mol) and the reaction mixture was heated to reflux for 1 hour. Reaction workup yields the crude product which was purified by column chromatography on silica gel (40% ethylacetate in hexane) to afford 400 mg of the product (74.48% yield).

$^1$H NMR (DMSO-$D_6$, 300 MHz) δ: 8.0 (br s, 1H), 7.4 (d, 1H), 7.45-7.2 (m, 5H), 7.1 (d, 1H), 6.65 (t, 1H), 4.5 (s, 2H), 4.15 (t, 2H), 3.9 (t, 2H), 1.6 (s, 3H), 0.3 (s, 9H)

Synthesis of Intermediate 1-Benzyl-7-(2-fluoro-4-iodo-phenylamino)-6-methyl-8-nitro-2,3-dihydro-1H-imidazo[1,2-a]pyridin-5-one (I-3b)

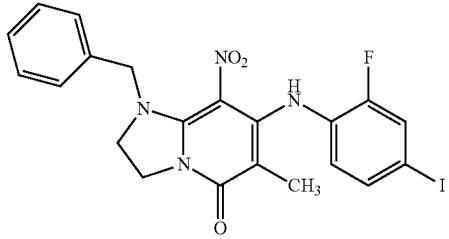 [SMILES: Cc1c(Nc2ccc(I)cc2F)c([N+](=O)[O-])c2n(c1=O)CCN2Cc1ccccc1]

1-Benzyl-7-(2-fluoro-4-trimethylsilanyl-phenylamino)-6-methyl-8-nitro-2,3-dihydro-1H-imidazo[1,2-a]pyridin-5-one (400 mg, 0.001 mol) in DCM (10 mL) was added to $AgBF_4$ (500 mg) in DCM (10 mL) previously sparged with nitrogen for 10 minutes at –50° C. The resulting mixture was stirred at –50° C. for 30 minutes under nitrogen atmosphere. This was followed by the addition of ICl (0.85 mL) and the stirring was continued for a further 1 hour at –50° C. under nitrogen atmosphere. The reaction mixture was monitored by TLC (65% ethylacetate in hexane). The reaction mixture was quenched with sodium thiosuphate and extracted with DCM. The organic layer was washed with ammonia solution and concentrated to get the crude product which was washed with diethyl ether to afford 250 mg of the product (56.1% yield).

$^1$H NMR (DMSO-$D_6$, 300 MHz) δ: 8.0 (br s, 1H), 7.5 (d, 1H), 7.4-7.2 (m, 6H), 6.5 (t, 1H), 4.5 (s, 2H), 4.2 (t, 2H), 4.0 (t, 2H), 1.6 (s, 3H). LCMS: 83.8%, m/z=521(M+1)

Synthesis of Intermediate 8-Amino-1-benzyl-7-(2-fluoro-4-iodo-phenylamino)-6-methyl-2,3-dihydro-1H-imidazo[1,2-a]pyridin-5-one (I-3c)

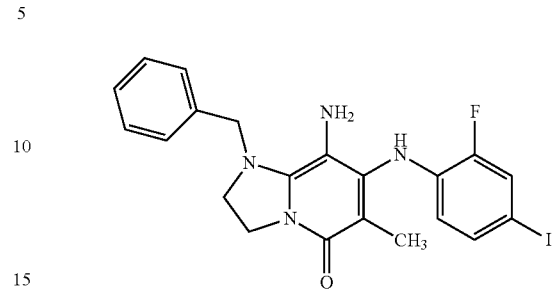

Following the procedure set forth in Example 1 for the preparation of I-1g, 1-benzyl-7-(2-fluoro-4-iodo-phenylamino)-6-methyl-8-nitro-2,3-dihydro-1H-imidazo[1,2-a]pyridin-5-one (280 mg, 0.001 mol) in THF (30 mL) was reacted with zinc (211 mg, 0.003 mol) and HCl (1 mL) to afford 250 mg of the crude product which was used in the next step without further purification.

Synthesis of Intermediate Cyclopropanesulfonic acid [1-benzyl-7-(2-fluoro-4-iodo-phenylamino)-6-methyl-5-oxo-1,2,3,5-tetrahydro-imidazo[1,2-a]pyridin-8-yl]-amide (I-3d)

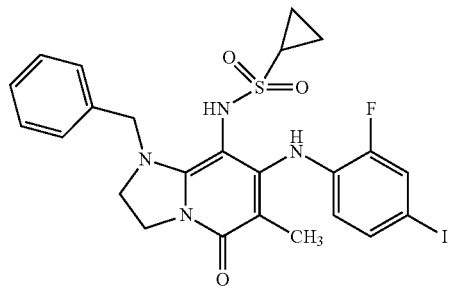 [SMILES: Cc1c(Nc2ccc(I)cc2F)c(NS(=O)(=O)C2CC2)c2n(c1=O)CCN2Cc1ccccc1]

Following the procedure set forth for the preparation of Example 1A, 8-amino-1-benzyl-7-(2-fluoro-4-iodo-phenylamino)-6-methyl-2,3-dihydro-1H-imidazo[1,2-a]pyridin-5-one (250 mg, 0.001 mol) in pyridine (4 mL) was reacted with cyclopropanesulfonyl chloride (144 mg, 0.001 mol) to afford the crude product. Purification by column chromatography on silica gel (80% ethylacetate in hexane) afforded 40 mg of the product (13.2% yield).

LCMS: 83.8%, m/z=595.1(M+1)

Synthesis of the Title Compound; Cyclopropanesulfonic acid [7-(2-fluoro-4-iodo-phenylamino)-6-methyl-5-oxo-1,2,3,5-tetrahydro-imidazo[1,2-a]pyridin-8-yl]-amide (3A)

Following the procedure set forth for the preparation of Example 2A, cyclopropanesulfonic acid [1-benzyl-7-(2-fluoro-4-iodo-phenylamino)-6-methyl-5-oxo-1,2,3,5-tetrahydro-imidazo[1,2-a]pyridin-8-yl]-amide (40 mg, 0.0001 mol) in DCM (3 mL) was reacted with borontribromide (0.025 g, 0.0001 mol) to afford the crude product. Purification by column chromatography on silica gel (4% methanol in $CHCl_3$) afforded 3 mg of the product (9.09% yield).

¹H NMR (DMSO-D₆, 300 MHz) δ: 8.4 (br s, 1H), 7.6 (d, 1H), 7.4 (d, 1H), 7.2 (br s, 1H), 7.0 (br s, 1H), 6.4 (t, 1H), 4.0 (t, 2H), 3.8 (t, 4H), 2.1 (s, 1H), 1.6 (s, 3H), 0.8 (s, 4H). LCMS: 94.3%, m/z=504.8(M+1). HPLC: 87.6%

Example 4

Synthesis of 1-(2,3-Dihydroxy-propyl)-cyclopropanesulfonic acid [7-(4-bromo-2-fluoro-phenylamino)-6-methyl-5-oxo-1,2,3,5-tetrahydro-imidazo[1,2-a]pyridin-8-yl]-amide (4A)

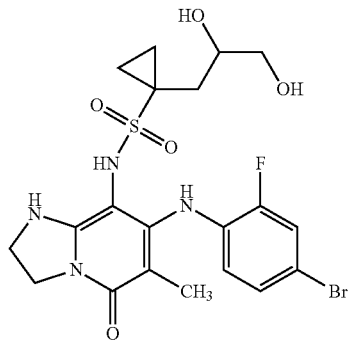

(4A)

Synthesis of Intermediate 7-(4-Bromo-2-fluoro-phenylamino)-6-methyl-8-nitro-2,3-dihydro-1H-imidazo[1,2-a]pyridin-5-one (I-4a)

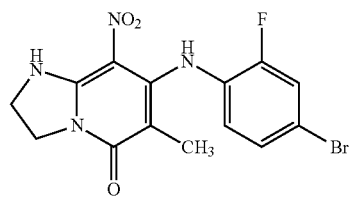 [SMILES: Cc1c(Nc2ccc(Br)cc2F)c([N+](=O)[O-])c2n(c1=O)CCN2]

HBr in acetic acid (20 mL) was added to 1-benzyl-7-(4-bromo-2-fluoro-phenylamino)-6-methyl-8-nitro-2,3-dihydro-1H-imidazo[1,2-a]pyridin-5-one (I-1f: 1.4 g) and the resulting mixture was stirred at room temperature for 2 hours. The reaction was monitored by TLC (100% ethylacetate). The reaction mixture was partitioned between ice water and ethyl acetate. The organic layer was concentrated to afford the crude product. Purification by column chromatography on silica gel (65% ethylacetate in hexane) afforded 600 mg of the product (54.5% yield).

¹H NMR (DMSO-D₆, 300 MHz) δ: 9.6 (br s, 1H), 9.0 (s, 1H), 7.6 (d, 1H), 7.4 (s, 1H), 6.8 (t, 1H), 4.1 (t, 2H), 3.9 (t, 2H), 1.6 (s, 3H)

Synthesis of Intermediate 7-(4-Bromo-2-fluoro-phenylamino)-6-methyl-8-nitro-5-oxo-2,3-dihydro-5H-imidazo[1,2-a]pyridine-1-carboxylic acid tert-butyl ester (I-4b)

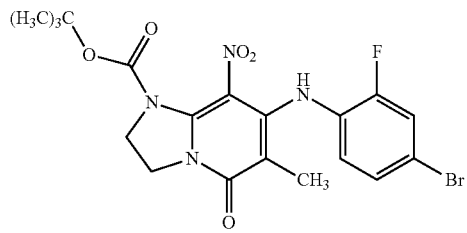 [SMILES: Cc1c(Nc2ccc(Br)cc2F)c([N+](=O)[O-])c2n(c1=O)CCN2C(=O)OC(C)(C)C]

BOC anhydride (21 mg, 0.0001 mol) was added to a stirred solution of 7-(4-bromo-2-fluoro-phenylamino)-6-methyl-8-nitro-2,3-dihydro-1H-imidazo[1,2-a]pyridin-5-one (35 mg, 0.0001 mol) and DMAP (2.4 mg, 0.0001 mol) in acetonitrile (3 mL). The resulting mixture was stirred at room temperature for 2 hours. The reaction was monitored by TLC (100% ethylacetate). The reaction mixture was concentrated and partitioned between ethylacetate and water. The organic layer was concentrated to afford the crude product. Purification by column chromatography on basic alumina (60% ethylacetae in hexane) afforded 30 mg of the product (68.18% yield).

¹H NMR (CDCl₃, 300 MHz) δ: 7.8 (s, 1H), 7.3 (d, 1H), 7.1 (d, 1H), 6.5 (t, 1H), 4.3-4.2 (m, 4H), 1.8 (s, 3H), 1.5 (s, 9H)

Synthesis of Intermediate 8-Amino-7-(4-bromo-2-fluoro-phenylamino)-6-methyl-5-oxo-2,3-dihydro-5H-imidazo[1,2-a]pyridine-1-carboxylic acid tert-butyl ester (I-4c)

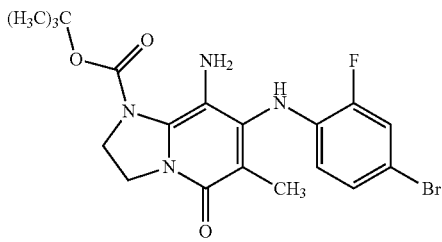 [SMILES: Cc1c(Nc2ccc(Br)cc2F)c(N)c2n(c1=O)CCN2C(=O)OC(C)(C)C]

Zinc (284 mg, 0.004 mol) was added to a stirred solution of 7-(4-bromo-2-fluoro-phenylamino)-6-methyl-8-nitro-5-oxo-2,3-dihydro-5H-imidazo[1,2-a]pyridine-1-carboxylic acid tert-butyl ester (350 mg, 0.0007 mol) and NH₄Cl (310 mg, 0.006 mol) in water and THF (10 mL). The resulting mixture was stirred at room temperature for 40 minutes. The reaction was monitored by TLC (100% ethylacetate). The reaction mixture was concentrated and partitioned between ethylacetate and water. The organic layer was washed with saturated NaHCO₃ solution and concentrated to afford 150 mg of the crude product which was used in the next step without further purification.

Synthesis of Intermediate 8-(1-Allyl-cyclopropane-sulfonylamino)-7-(4-bromo-2-fluoro-phenylamino)-6-methyl-5-oxo-2,3-dihydro-5H-imidazo[1,2-a]pyridine-1-carboxylic acid tert-butyl ester (I-4d)

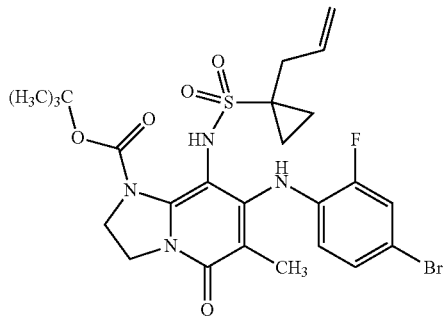 [SMILES: C=CCC1(S(=O)(=O)Nc2c(Nc3ccc(Br)cc3F)c(C)c(=O)n3c2N(C(=O)OC(C)(C)C)CC3)CC1]

1-Allyl-cyclopropanesulfonyl chloride (121 mg, 0.001 mol) was added to a stirred solution of 8-amino-7-(4-bromo-2-fluoro-phenylamino)-6-methyl-5-oxo-2,3-dihydro-5H-imidazo[1,2-a]pyridine-1-carboxylic acid tert-butyl ester (150 mg, 0.0003 mol) in pyridine (3 mL). The resulting mixture was stirred at room temperature for 12 hours. The reaction was monitored by TLC (100% ethylacetate). The reaction mixture was concentrated and partitioned between ethylacetate and water. The organic layer concentrated to afford the crude product. Purification by column chromatography on silica gel (60% ethylacetate in hexane) afforded 120 mg of the product (60.6% yield).

Synthesis of Intermediate 7-(4-Bromo-2-fluoro-phenylamino)-8-[1-(2,3-dihydroxy-propyl)-cyclopropanesulfonylamino]-6-methyl-5-oxo-2,3-dihydro-5H-imidazo[1,2-a]pyridine-1-carboxylic acid tert-butyl ester (I-4e)

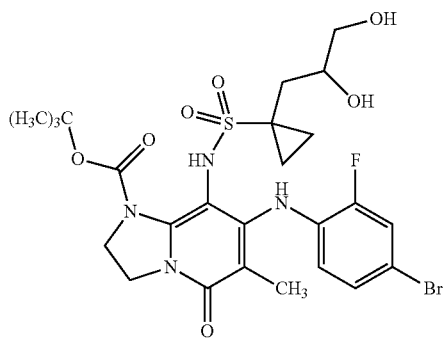 [SMILES: Cc1c(Nc2ccc(Br)cc2F)c(NS(=O)(=O)C2(CC(O)CO)CC2)c2n(c1=O)CCN2C(=O)OC(C)(C)C]

OsO$_4$ (0.1 mg, 0.00002 mol) was added to a stirred solution of 8-(1-allyl-cyclopropanesulfonylamino)-7-(4-bromo-2-fluoro-phenylamino)-6-methyl-5-oxo-2,3-dihydro-5H-imidazo[1,2-a]pyridine-1-carboxylic acid tert-butyl ester (120 mg, 0.0002 mol) and N-methylmorpholine-N-oxide (35 mg, 0.0003 mol) in water and THF (3 mL). The resulting mixture was stirred at room temperature for 12 hours. The reaction was monitored by TLC (10% MeOH in CHCl$_3$). The reaction mixture was partitioned between ethylacetate and water. The organic layer was concentrated to afford 75 mg of the crude product which was used in the next step without further purification.

Synthesis of the Title Compound: 1-(2,3-Dihydroxy-propyl)-cyclopropanesulfonic acid [7-(4-bromo-2-fluoro-phenylamino)-6-methyl-5-oxo-1,2,3,5-tetrahydro-imidazo[1,2-a]pyridin-8-yl]-amide (4A)

Concentrated HCl (3 mL) was added to a stirred solution of 7-(4-bromo-2-fluoro-phenylamino)-8-[1-(2,3-dihydroxy-propyl)-cyclopropanesulfonylamino]-6-methyl-5-oxo-2,3-dihydro-5H-imidazo[1,2-a]pyridine-1-carboxylic acid tert-butyl ester (75 mg) in THF (10 mL). The resulting mixture was stirred at 45° C. for 1 hour. The reaction was monitored by TLC (10% MeOH in CHCl$_3$). The reaction mixture was concentrated and partitioned between ethyl acetate and water. The organic layer was washed with saturated NaHCO$_3$ solution and concentrated to afford 25 mg of the product (39.58% yield).

$^1$H NMR (DMSO-D$_6$, 300 MHz) δ: 8.5-8.3 (br s, 1H), 7.5 (dd, 1H), 7.2 (d, 1H), 7.1 (s, 1H), 7.0-6.8 (t, 1H), 5.1-4.9 (s, 1H), 4.7 (t, 1H), 4.5 (t, 1H), 4.2-4.0 (q, 2H), 3.7-3.5 (m, 4H), 2.3 (d, 1H), 1.8-1.6 (q, 2H), 1.6 (s, 4H), 1.2-0.9 (m, 4H)

LCMS: 98.58%, m/z=533.0(M+2) HPLC: 97.31%

Example 5

Synthesis of 1-(2,3-Dihydroxy-propyl)-cyclopropanesulfonic acid [7-(2-fluoro-4-iodo-phenylamino)-6-methyl-5-oxo-1,2,3,5-tetrahydro-imidazo[1,2-a]pyridin-8-yl]-amide (5A)

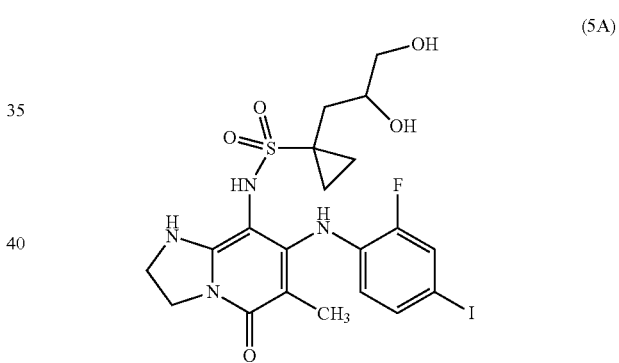

(5A)

Synthesis of Intermediate 7-(2-Fluoro-4-iodo-phenylamino)-6-methyl-8-nitro-2,3-dihydro-1H-imidazo[1,2-a]pyridin-5-one (I-5a)

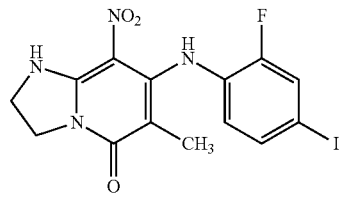 [SMILES: Cc1c(Nc2ccc(I)cc2F)c([N+](=O)[O-])c2n(c1=O)CCN2]

HBr in acetic acid (30 mL) was added to 1-benzyl-7-(2-fluoro-4-iodo-phenylamino)-6-methyl-8-nitro-2,3-dihydro-1H-imidazo[1,2-a]pyridin-5-one (I-3b: 2.5 g) and the resulting mixture was stirred at room temperature for 2 hours. The reaction was monitored by TLC (100% ethylacetate). The reaction mixture was basified with NaHCO$_3$ solution and partitioned between ice water and ethyl acetate. The organic layer was concentrated to afford the crude product. Purification by column chromatography on silica gel (60% ethylacetate in hexane) afforded 1.5 g of the product (75% yield).

Synthesis of Intermediate 7-(2-Fluoro-4-iodo-phenylamino)-6-methyl-8-nitro-5-oxo-2,3-dihydro-5H-imidazo[1,2-a]pyridine-1-carboxylic acid tert-butyl ester (I-5b)

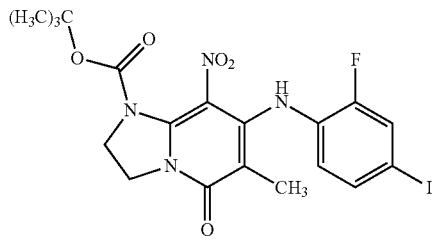 [SMILES: Cc1c(Nc2ccc(I)cc2F)c([N+](=O)[O-])c2n(c1=O)CCN2C(=O)OC(C)(C)C]

BOC anhydride (761 mg, 0.003 mol) was added to a stirred solution of 7-(2-fluoro-4-iodo-phenylamino)-6-methyl-8-nitro-2,3-dihydro-1H-imidazo[1,2-a]pyridin-5-one (1 g, 0.002 mol) and DMAP (530 mg, 0.003 mol) in acetonitrile (20 mL). The resulting mixture was stirred at room temperature for 2 hours. The reaction was monitored by TLC (100% ethylacetate). The reaction mixture was concentrated and partitioned between ethylacetate and water. The organic layer was concentrated to afford 900 mg of the crude product which was used in the next step without further purification.

Synthesis of Intermediate 8-Amino-7-(2-fluoro-4-iodo-phenylamino)-6-methyl-5-oxo-2,3-dihydro-5H-imidazo[1,2-a]pyridine-1-carboxylic acid tert-butyl ester (I-5c)

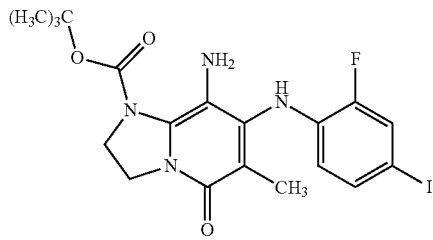 [SMILES: Cc1c(Nc2ccc(I)cc2F)c(N)c2n(c1=O)CCN2C(=O)OC(C)(C)C]

Zinc (296 mg, 0.005 mol) was added to a stirred solution of 7-(2-fluoro-4-iodo-phenylamino)-6-methyl-8-nitro-5-oxo-2,3-dihydro-5H-imidazo[1,2-a]pyridine-1-carboxylic acid tert-butyl ester (400 mg, 0.0008 mol) and NH$_4$Cl (322 mg, 0.006 mol) in water and THF (15 mL). The resulting mixture was stirred at room temperature for 30 minutes. The reaction was monitored by TLC (100% ethylacetate). The reaction mixture was concentrated and partitioned between ethylacetate and water. The organic layer was washed with saturated NaHCO$_3$ solution and concentrated to afford 350 mg of the crude product which was used in the next step without further purification.

Synthesis of Intermediate 8-(1-Allyl-cyclopropane-sulfonylamino)-7-(2-fluoro-4-iodo-phenylamino)-6-methyl-5-oxo-2,3-dihydro-5H-imidazo[1,2-a]pyridine-1-carboxylic acid tert-butyl ester (I-5d)

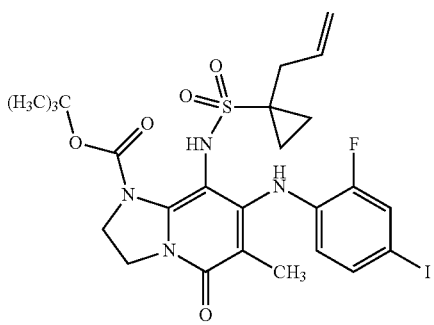 [SMILES: C=CCC1(S(=O)(=O)Nc2c(Nc3ccc(I)cc3F)c(C)c(=O)n3c2N(C(=O)OC(C)(C)C)CC3)CC1]

1-Allyl-cyclopropanesulfonyl chloride (259 mg, 0.001 mol) was added to a stirred solution of 8-amino-7-(2-fluoro-4-iodo-phenylamino)-6-methyl-5-oxo-2,3-dihydro-5H-imidazo[1,2-a]pyridine-1-carboxylic acid tert-butyl ester (350 mg, 0.001 mol) in pyridine (3 mL). The resulting mixture was stirred at room temperature for 12 hours. The reaction was monitored by TLC (100% ethylacetate). The reaction mixture was concentrated and partitioned between ethylacetate and water. The organic layer concentrated to afford the crude product. Purification by column chromatography on silica gel (75% ethylacetate in hexane) afforded 125 mg of the product (27.7% yield).

Synthesis of Intermediate 8-[1-(2,3-Dihydroxy-propyl)-cyclopropanesulfonylamino]-7-(2-fluoro-4-iodo-phenylamino)-6-methyl-5-oxo-2,3-dihydro-5H-imidazo[1,2-a]pyridine-1-carboxylic acid tert-butyl ester (I-5e)

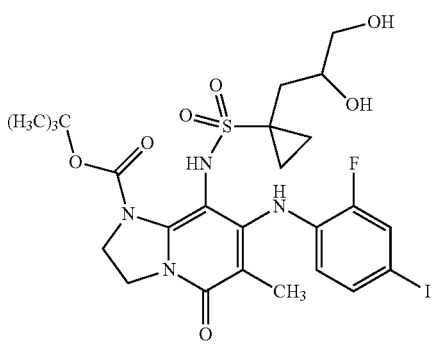 [SMILES: Cc1c(Nc2ccc(I)cc2F)c(NS(=O)(=O)C2(CC(O)CO)CC2)c2n(c1=O)CCN2C(=O)OC(C)(C)C]

OsO$_4$ (0.004 g, 0.00002 mol) was added to a stirred solution of 8-(1-allyl-cyclopropanesulfonylamino)-7-(2-fluoro-4-iodo-phenylamino)-6-methyl-5-oxo-2,3-dihydro-5H-imidazo[1,2-a]pyridine-1-carboxylic acid tert-butyl ester (125 mg, 0.0002 mol) and N-methylmorpholine-N-oxide (34 mg, 0.0003 mol) in water and THF (3 mL). The resulting mixture was stirred at room temperature for 3 hours. The reaction was monitored by TLC (10% MeOH in CHCl₃). The reaction mixture was partitioned between ethylacetate and water. The organic layer concentrated to afford 80 mg of the crude product which was used in the next step without further purification.

Synthesis of the Title Compound: 1-(2,3-Dihydroxy-propyl)-cyclopropanesulfonic acid [7-(2-fluoro-4-iodo-phenylamino)-6-methyl-5-oxo-1,2,3,5-tetrahydro-imidazo[1,2-a]pyridin-8-yl]-amide (5A)

Concentrated HCl (3 mL) was added to a stirred solution of 8-[1-(2,3-dihydroxy-propyl)-cyclopropanesulfonylamino]-7-(2-fluoro-4-iodo-phenylamino)-6-methyl-5-oxo-2,3-dihydro-5H-imidazo[1,2-a]pyridine-1-carboxylic acid tert-butyl ester (80 mg) in THF (5 mL). The resulting mixture was stirred at 40° C. for 2 hours. The reaction was monitored by TLC (15% MeOH in CHCl₃). The reaction mixture was concentrated and partitioned between ethylacetate and water. The organic layer was washed with saturated NaHCO₃ solution and concentrated to afford the crude product. Purification by column chromatography on silica gel (5% methanol in CHCl₃), followed by preparative HPLC afforded 10 mg of the product (14.7% yield)

$^1$H NMR (DMSO-D₆, 300 MHz) δ: 8.4-8.3 (br s, 1H), 7.5 (d, 1H), 7.3 (d, 1H), 7.1 (s, 1H), 7.0-6.9 (br s, 1H), 6.3 (t, 1H), 5.1-4.9 (br s, 1H), 4.8-4.6 (br s, 1H), 3.7-3.5 (m, 3H), 1.6 (s, 3H), 1.3-1.2 (br s, 2H), 1.1-1.0 (m, 4H)

LCMS: 98.58%, m/z=578.9(M+1) HPLC: 97.67%

Example 6

Synthesis of 3-Hydroxy-cyclobutanesulfonic acid [7-(2-fluoro-4-iodo-phenylamino)-6-methyl-5-oxo-1,2,3,5-tetrahydro-imidazo[1,2-a]pyridin-8-yl]-amide (6A)

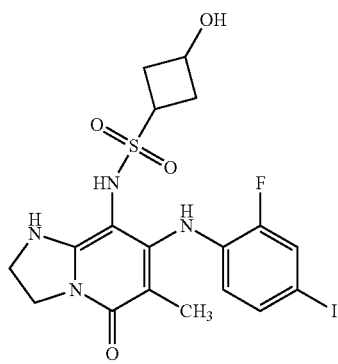

(6A)

Synthesis of Intermediate 8-(3-Benzyloxy-cyclobutanesulfonylamino)-7-(2-fluoro-4-iodo-phenylamino)-6-methyl-5-oxo-2,3-dihydro-5H-imidazo[1,2-a]pyridine-1-carboxylic acid tert-butyl ester (I-6a)

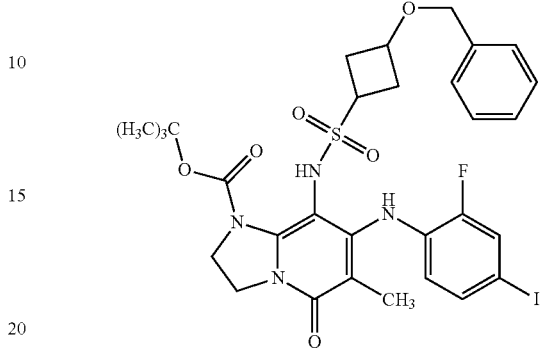

Using the same reaction conditions and workup as described for the preparation of Intermediate (I-5d), 8-Amino-7-(2-fluoro-4-iodo-phenylamino)-6-methyl-5-oxo-2,3-dihydro-5H-imidazo[1,2-a]pyridine-1-carboxylic acid tert-butyl ester (I-5c: 350 mg, 0.7 mmol) in pyridine (3 mL) was reacted with 3-benzyloxy-cyclobutanesulfonyl chloride (273 mg, 1.05 mmol) to afford the crude product. Purification by column chromatography on silica gel (80% ethylacetate in hexane) afforded 250 mg of the product (45.3% yield).

$^1$HNMR (400 MHz, DMSO-D₆): δ 7.68-7.64 (br s, 1H), 7.58 (d, 1H), 7.50 (s, 1H), 7.40-7.24 (m, 6H), 6.35 (t, 1H), 4.32 (s, 2H), 4.30-4.00 (m, 4H), 3.80 (t, 1H), 3.51-3.40 (m, 1H), 2.30-2.20 (br s, 2H), 2.10-1.90 (m, 2H), 1.70 (s, 3H), 1.50 (s, 9H)

Synthesis of Intermediate 3-Benzyloxy-cyclobutanesulfonic acid [7-(2-fluoro-4-iodo-phenylamino)-6-methyl-5-oxo-1,2,3,5-tetrahydro-imidazo[1,2-a]pyridin-8-yl]-amide (I-6b)

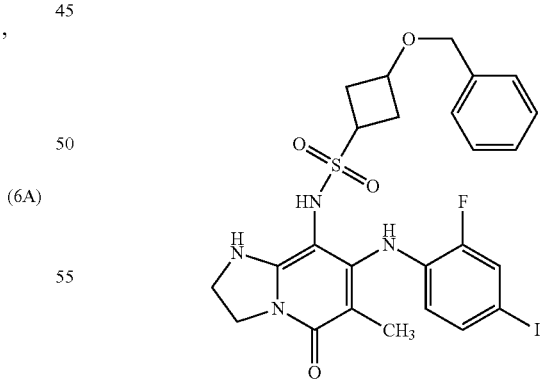

Dioxane hydrochloride (3 mL) was added to 8-(3-benzyloxy-cyclobutanesulfonylamino)-7-(2-fluoro-4-iodo-phenylamino)-6-methyl-5-oxo-2,3-dihydro-5H-imidazo[1,2-a]pyridine-1-carboxylic acid tert-butyl ester (250 mg) and the resulting mixture was stirred at room temperature for 12 hours. The reaction was monitored by TLC (5% MeOH in CHCl₃). The reaction mixture was concentrated; the concentrate was neutralized with NaHCO₃ solution and extracted with ethylacetate. The organic layer was washed with brine, dried over Na₂SO₄ and concentrated to afford 120 mg of the product (55.8% yield).

LCMS: m/z=624.8 (M+1)

Synthesis of the Title Compound; 3-Hydroxy-cyclobutanesulfonic acid [7-(2-fluoro-4-iodo-phenylamino)-6-methyl-5-oxo-1,2,3,5-tetrahydro-imidazo[1,2-a]pyridin-8-yl]-amide (6A)

3-Benzyloxy-cyclobutanesulfonic acid [7-(2-fluoro-4-iodo-phenylamino)-6-methyl-5-oxo-1,2,3,5-tetrahydro-imidazo[1,2-a]pyridin-8-yl]-amide (120 mg, 0.19 mmol) in DCM (3 mL) was reacted with 1M BCl₃ (67 mg, 0.57 mmol) at 0° C. The resulting mixture was stirred at room temperature for 6 hours. Purification by column chromatography on silica gel (5% MeOH in CHCl₃), followed by preparative HPLC afforded 30 mg of the product (29.4% yield).

¹HNMR (400 MHz, DMSO-D₆): δ 8.26-8.22 (br s, 1H), 7.6 (d, 1H), 7.33 (d, 1H), 7.32-7.28 (br s, 1H), 6.83-6.80 (br s, 1H), 6.3 (t, 1H), 4.1 (t, 2H), 3.75 (t, 1H), 3.6 (t, 2H), 3.4-3.3 (m, 2H), 2.4-2.3 (br s, 2H), 2.1-2.0 (m, 2H), 1.6 (s, 3H).

LCMS: 95.3%, m/z=534.7 (M+1). HPLC: 97.2%

Example 7

Synthesis of Cyclopropanesulfonic acid [7-(2-fluoro-4-iodo-phenylamino)-6-methyl-5-oxo-2,3-dihydro-5H-oxazolo[3,2-a]pyridin-8-yl]-amide (7A)

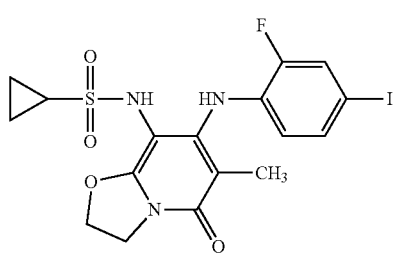

(7A)

Synthesis of Intermediate
2-Nitromethylene-oxazolidine (I-7a)

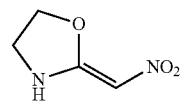

p-Toluene sulfonic acid (0.5 g) was added to a boiling solution of 1,1-bis-methylsulfanyl-2-nitro-ethene (I-1b: 20 g, 12.13 mol) in ethanol (200 mL). This was followed by the addition of ethanolamine (7.4 g, 12.13 mmol) and the resulting mixture was heated to reflux for 12 hours. The reaction mixture was monitored by TLC (100% ethylacetate). The reaction mixture was concentrated, 300 mL of water added and resultant filtered. The filtrate was further concentrated and was followed by the addition of acetone. The reaction mixture was refluxed for 1 hour, cooled to room temperature, and filtered. The acetone layer was concentrated to afford 4.1 g of the crude product which was used in the next step without further purification.

¹HNMR (300 MHz, DMSO-D₆): δ 9.9 (s, 1H), 6.6 (s, 1H), 4.6 (t, 2H), 3.7 (t, 2H)

Synthesis of Intermediate 7-Hydroxy-6-methyl-8-nitro-2,3-dihydro-oxazolo[3,2-a]pyridin-5-one (I-7b)

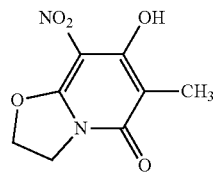

2-Nitromethylene-oxazolidine (3 g, 23.0 mmol) was added portion wise to a stirred solution of 2-methyl-malonic acid bis-(2,4,6-trichloro-phenyl) ester (12 g, 25.15 mmol) in Xylene (50 mL) under nitrogen atmosphere over a period of 1 hour at 125° C. The resulting mixture was heated to 125° C. for 5 hours. The reaction mixture was monitored by TLC (50% ethylacetate in hexane). The reaction mixture was concentrated and the concentrate was purified by column chromatography on silica gel (60% ethylacetate in hexane) to afford 1.5 g of the product (30% yield).

¹HNMR (300 MHz, DMSO-D₆): δ 11.1 (s, 1H), 5.0 (t, 2H), 4.2 (t, 2H), 1.85 (s, 3H)

Synthesis of Intermediate Trifluoro-methanesulfonic acid 6-methyl-8-nitro-5-oxo-2,3-dihydro-5H-oxazolo[3,2-a]pyridin-7-yl ester (I-7c)

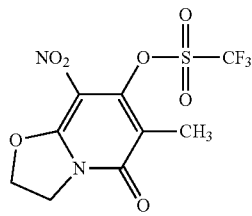

Triflic anhydride (2.78 g, 9.9 mmol) was added dropwise to a stirred solution of 7-hydroxy-6-methyl-8-nitro-2,3-dihydro-oxazolo[3,2-a]pyridin-5-one (1.5 g, 7.0 mmol) and TEA (1.42 g, 14.060 mmol) in DCM (30 mL) at −78° C. over a period of 1 hour. The resulting mixture was stirred at room temperature for 5 hours. The reaction mixture was monitored by TLC (50% ethylacetate in hexane). The reaction mixture was partitioned between DCM and water. The organic layer was washed with water, brine solution, dried over Na₂SO₄ and concentrated. Purification by column chromatography on silica gel (50% ethylacetate in hexane) afforded 0.5 g of the product (20.6% yield).

¹HNMR (300 MHz, DMSO-D₆): δ 5.0 (t, 2H), 4.25 (t, 2H), 2.0 (s, 3H)

Synthesis of Intermediate 7-(2-Fluoro-4-trimethylsilanyl-phenylamino)-6-methyl-8-nitro-2,3-dihydro-oxazolo[3,2-a]phyridin-5-one (I-7d)

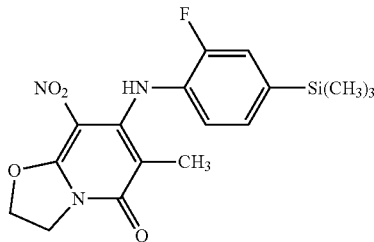

Pd(dba)$_3$ (0.1 g, 0.109 mmol), potassium phosphate tribasic (0.5 g, 2.35 mmol), xantphos (0.07 g, 0.120 mmol) were dissolved in dry toluene (30 mL) and the resulting mixture was sparged for 30 minutes with argon. This was followed by addition of trifluoro-methanesulfonic acid 6-methyl-8-nitro-5-oxo-2,3-dihydro-5H-oxazolo[3,2-a]pyridin-7-yl ester (0.5 g, 1.45 mmol) and 2-fluoro-4-trimethylsilanyl-phenylamine (0.3 g, 1.64 mmol) and the reaction flask was again sparged for another 15 minutes. The reaction mixture was heated at 100° C. for 5 hours. The reaction was monitored by TLC (60% ethylacetate in hexane). The reaction mixture was filtered through celite bed and the filtrate was concentrated. Purification by column chromatography on silica gel (60% ethylacetate in hexane) afforded 0.25 g of the product (45.8% yield).

$^1$HNMR (400 MHz, DMSO-D$_6$): δ 8.25 (s, 1H), 7.1-7.3 (m, 2H), 6.7 (t, 1H), 4.95 (t, 2H), 4.25 (t, 2H), 1.7 (s, 3H), 0.25 (s, 9H)

Synthesis of Intermediate 7-(2-Fluoro-4-iodo-phenylamino)-6-methyl-8-nitro-2,3-dihydro-oxazolo[3,2-a]pyridin-5-one (I-7e)

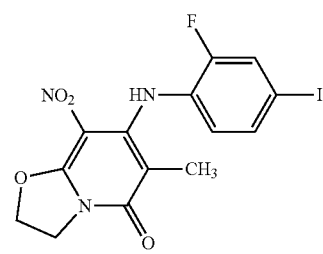 [SMILES: Cc1c(Nc2ccc(I)cc2F)c([N+](=O)[O-])c2n(c1=O)CCO2]

A stirred solution of 7-(2-fluoro-4-trimethylsilanyl-phenylamino)-6-methyl-8-nitro-2,3-dihydro-oxazolo[3,2-a]pyridin-5-one (0.25 g, 0.66 mmol) in dry DCM (10 mL) and iodine monochloride (0.8 mL) were added to silver tetrafluoroborate (0.4 g, 2.05 mmol) in DCM (10 mL) previously degassed with nitrogen for 30 minutes at –50° C. The resulting mixture was stirred at –50° C. for 1 hour. The reaction was monitored by TLC (50% ethylacetate in hexane). This was followed by the addition of 20 mL of sodium thiosulphate and filtered through celite. The filtrate was concentrated to afford 0.2 g of the product (70% yield).

$^1$HNMR (300 MHz, CDCl$_3$): δ 8.6 (s, 1H), 7.2-7.6 (m, 2H), 6.45 (t, 1H), 5.0 (t, 2H), 4.45 (t, 2H), 1.65 (s, 3H)

Synthesis of Intermediate 8-Amino-7-(2-fluoro-4-iodo-phenylamino)-6-methyl-2,3-dihydro-oxazolo[3,2-a]pyridin-5-one (I-7f)

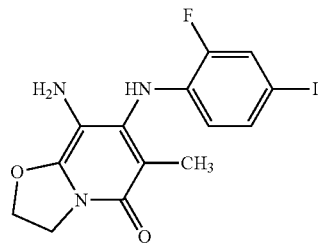 [SMILES: Cc1c(Nc2ccc(I)cc2F)c(N)c2n(c1=O)CCO2]

Concentrated HCl (0.2 mL) and SnCl$_2$.H$_2$O (0.24 g, 1.06 mmol) were added to 7-(2-fluoro-4-iodo-phenylamino)-6-methyl-8-nitro-2,3-dihydro-oxazolo[3,2-a]pyridin-5-one (0.15 g, 0.347 mmol) in ethanol (5 mL). The resulting mixture was heated to reflux for 2 hours. The reaction was monitored by TLC (100% ethylacetate). The reaction mixture was cooled to room temperature, diluted with ethylacetate, basified with saturated bicarbonate solution and filtered through celite. The organic layer was washed with brine solution, dried over Na$_2$SO$_4$ and concentrated to afford 0.08 g of the crude product which was used in the next step without further purification.

Synthesis of the Title Compound: Cyclopropanesulfonic acid [7-(2-fluoro-4-iodo-phenylamino)-6-methyl-5-oxo-2,3-dihydro-5H-oxazolo[3,2-a]pyridin-8-yl]-amide (7A)

Cyclopropane sulfonyl chloride (50 mg, 0.35 mmol) was added to a solution of 8-amino-7-(2-fluoro-4-iodo-phenylamino)-6-methyl-2,3-dihydro-oxazolo[3,2-a]pyridin-5-one (I-7f: 80 mg, 0.199 mmol) in dry pyridine (1 mL) at 0° C. The resulting mixture was stirred at room temperature for 1 hour. The reaction was monitored by TLC (100% ethylacetate). The reaction mixture was partitioned between ethylacetate and water. The organic layer was washed with water, brine solution, dried over Na$_2$SO$_4$ and concentrated. Purification by column chromatography on silica gel (1.5% MeOH in DCM) afforded 3 mg of the product (3% yield).

$^1$HNMR (300 MHz, CDCl$_3$): δ 7.3-7.4 (m, 1H), 6.85 (s, 1H), 6.35 (t, 1H), 5.7 (s, 1H), 4.8 (t, 2H), 4.35 (t, 2H), 1.75 (s, 3H), 0.9-1.1 (m, 4H)

Example 8

Synthesis of 2-Hydroxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide (8A)

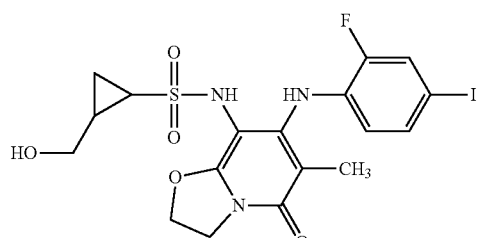

(8A)

Synthesis of Intermediate 2-Benzyloxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide (I-8a)

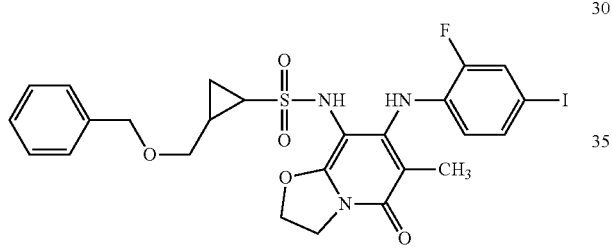

Using the same reaction conditions and workup as described for the preparation of Example 7A, 8-amino-7-(2-fluoro-4-iodo-phenylamino)-6-methyl-2,3-dihydro-oxazolo[3,2-a]pyridin-5-one (I-7f: 0.08 g, 0.0002 mol) in dry pyridine (2 ml) was reacted with 2-benzyloxymethyl-cyclopropanesulfonyl chloride (57 mg, 0.0002 mol) to afford the crude product. Purification by column chromatography on silica gel (2% MeOH in DCM) afforded 51 mg of the product (21% yield).

LCMS: 95.06%, m/z=625.9 (M+1)

Synthesis of the Title Compound; 2-Hydroxymethyl-cyclopropanesulfonic acid [7-(2-fluoro-4-iodo-phenylamino)-6-methyl-5-oxo-2,3-dihydro-5H-oxazolo[3, 2-a]pyridin-8-yl]-amide (8A)

2-Benzyloxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide (0.05 g, 0.0001 mol) was added to a stirred solution of $BF_3 \cdot EtO_2$ (0.34 g, 0.002 mol) in ethane thiol (0.05 g, 0.001 mol) at 0° C. under nitrogen atmosphere. The resulting mixture was stirred at room temperature overnight. The reaction was monitored by TLC (100% ethylacetate). The reaction mixture was quenched with saturated $NaHCO_3$ solution and extracted with ethylacetate. The organic layer was washed with water, dried over $Na_2SO_4$ and concentrated. Purification by column chromatography on silica gel (2-3% MeOH in DCM) afforded 11 mg of the product (27% yield).

$^1$HNMR (300 MHz, DMSO-$D_6$): δ 8.8 (s, 1H), 7.6-7.1 (m, 3H), 6.35 (t, 1H), 4.8-4.6 (m, 3H), 4.2 (t, 2H), 2.1 (s, 1H), 1.65 (s, 3H), 1.5-1.4 (m, 1H), 0.9-0.8 (m, 2H). LCMS: 94.35%, m/z=536 (M+1) HPLC: 89%

Example 9

Synthesis of 1-(2-Hydroxy-ethyl)-cyclopropane-sulfonic acid [7-(2-fluoro-4-iodo-phenylamino)-6-methyl-5-oxo-2,3-dihydro-5H-oxazolo[3,2-a]-pyridin-8-yl]-amide (9A)

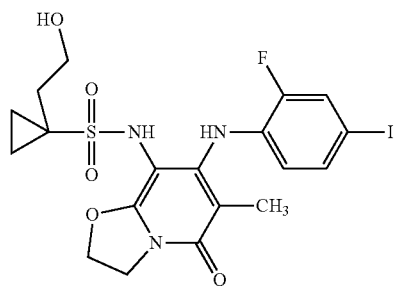

(9A)

Synthesis of Intermediate 1-Allyl-cyclopropane-sulfonic acid [7-(2-fluoro-4-iodo-phenylamino)-6-methyl-5-oxo-2,3-dihydro-5H-oxazolo[3,2-a]pyridin-8-yl]-amide (I-9a)

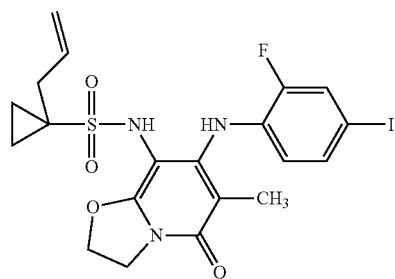

Using the same reaction conditions and workup as described for the preparation of Example 7A, 8-amino-7-(2-fluoro-4-iodo-phenylamino)-6-methyl-2,3-dihydro-oxazolo[3,2-a]pyridin-5-one (I-7f: 0.46 g, 0.001 mol) in dry pyridine (3 mL) was reacted with 1-allyl-cyclopropane sulfonyl chloride (0.25 g, 0.0014 mol) to afford the crude product. Purification by column chromatography on silica gel (2% MeOH in DCM) afforded 0.19 g of the product (30% yield).

$^1$HNMR (300 MHz, $CDCl_3$): δ 7.3-7.4 (m, 1H), 6.85 (s, 1H), 6.35 (t, 1H), 5.6-5.8 (m, 2H), 5.2-5.3 (m, 2H), 4.85 (t, 2H), 3.85 (t, 2H), 2.8 (d, 2H), 1.75 (s, 3H), 1.25 (t, 2H), 0.8 (t, 2H).

51

Synthesis of Intermediate 1-(2-Oxo-ethyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide (I-9b)

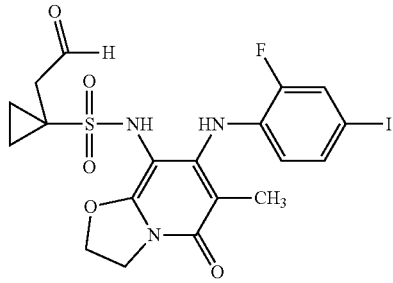 [SMILES: Cc1c(Nc2ccc(I)cc2F)c(NS(=O)(=O)C2(CC=O)CC2)c2n(c1=O)CCO2]

Osmium tetra oxide (8 mg, 0.035 mmol), 2,6-lutidine (0.08 g, 0.74 mmol) and sodium periodate (0.3 g, 0.001 mol) were added to a solution of 1-allyl-cyclopropanesulfonic acid [7-(2-fluoro-4-iodo-phenylamino)-6-methyl-5-oxo-2,3-dihydro-5H-oxazolo[3,2-a]pyridin-8-yl]-amide (0.19 g, 0.35 mmol) in dioxane (7 mL) and water (2 mL). The resulting mixture was stirred at room temperature for 5 hours. The reaction was monitored by TLC (5% MeOH in DCM). The reaction mixture was partitioned between ethylacetate and water. The organic layer was washed with water, brine solution, dried over $Na_2SO_4$, filtered and the filtrate was concentrated. Purification by column chromatography on silica gel (2% MeOH in DCM) afforded 0.12 g of the product (63% yield). LCMS: m/z=549 (M+1)

Synthesis of the Title Compound; 1-(2-Hydroxy-ethyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide (9A)

Sodium borohydride (0.1 g, 2.6 mmol) was added to a stirred solution of 1-(2-Oxo-ethyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide (0.12 g, 0.21 mmol) in THF (5 mL) and MeOH (2 mL) at room temperature. The resulting mixture was stirred at room temperature for 1 hour. The reaction was monitored by TLC (10% MeOH in DCM). The reaction mixture was concentrated under reduced pressure and partitioned between ethylacetate and water. The organic layer was washed with water, brine solution, dried over $Na_2SO_4$, filtered and the filtrate was concentrated. Purification by column chromatography on silica gel (2-4% MeOH in DCM) afforded 70 mg of the product (58% yield).

$^1$HNMR (300 MHz, DMSO-$D_6$): δ 8.75 (s, 1H), 7.2-7.4 (m, 3H), 6.25 (t, 1H), 4.75 (t, 2H), 4.45-4.6 (m, 1H), 4.25 (t, 2H), 3.5-3.6 (m, 2H), 2.1 (t, 2H), 1.6 (s, 3H), 0.7-0.9 (m, 4H). HPLC: 90%

52

Example 10

Synthesis of 1-(2,3-Dihydroxy-propyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide (10A)

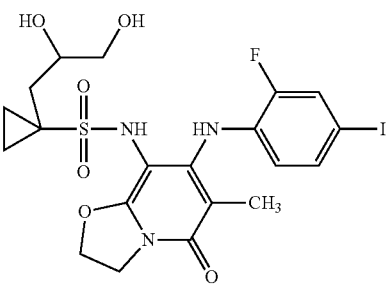

Osmium tetra oxide (8 mg, 0.003 mmol), N-methyl morpholine (8 mg, 0.068 mmol) and water (0.5 mL) were added to a stirred solution of 1-allyl-cyclopropanesulfonic acid [7-(2-fluoro-4-iodo-phenylamino)-6-methyl-5-oxo-2,3-dihydro-5H-oxazolo[3,2-a]pyridin-8-yl]-amide (I-9a: 0.04 g, 0.073 mmol) in THF (5 mL). The resulting mixture was stirred at room temperature overnight. The reaction was monitored by TLC (5% MeOH in DCM). The reaction mixture was partitioned between ethylacetate and water. The organic layer was washed with water, brine solution, dried over $Na_2SO_4$ and concentrated. Purification by thin layer chromatography on silica gel (5% MeOH in DCM) afforded 0.005 g of the product (11% yield).

$^1$HNMR (300 MHz, $CDCl_3$): δ 7.4-7.25 (m, 3H), 6.9 (s, 1H), 6.32 (t, 1H), 5.3 (s, 1H), 4.8 (t, 2H), 4.35 (t, 2H), 4.1-3.9 (m, 1H), 3.6-3.4 (m, 3H), 2.25-2.30 (m, 1H), 1.75 (s, 3H), 0.8-0.7 (m, 5H). LCMS: 97.5%, m/z=580.1 (M+1) HPLC: 97.67%

Example 11

Synthesis of 1-Hydroxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide (11A)

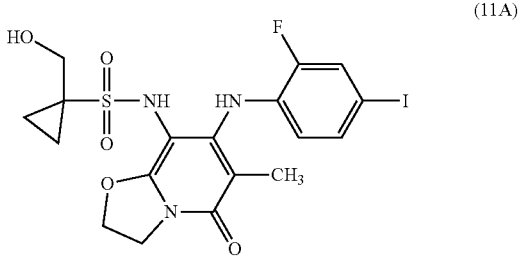 [SMILES: Cc1c(Nc2ccc(I)cc2F)c(NS(=O)(=O)C2(CO)CC2)c2n(c1=O)CCO2]

Synthesis of Intermediate 1-Benzyloxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide (I-11a)

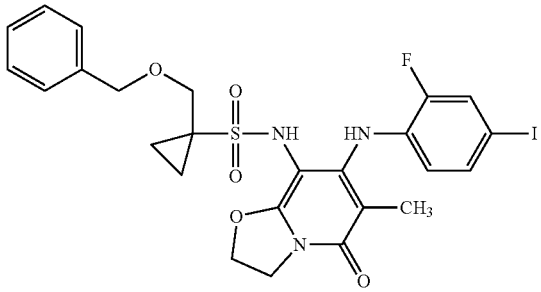 [SMILES: Cc1c(Nc2ccc(I)cc2F)c(NS(=O)(=O)C2(COCc3ccccc3)CC2)c2n(c1=O)CCO2]

Using the same reaction conditions and workup as described for the preparation of Example 7A, 8-amino-7-(2-fluoro-4-iodo-phenylamino)-6-methyl-2,3-dihydro-oxazolo [3,2-a]pyridin-5-one (I-7f: 0.35 g, 0.873 mmol) in pyridine (3 mL) was reacted with 1-benzyloxymethyl-cyclopropanesulfonyl chloride (0.34 mg, 1.30 mmol) to afford the crude product. Purification by column chromatography on silica gel (2% MeOH in $CHCl_3$) afforded 0.27 g of the product (50% yield).
LCMS: 88.4%, m/z=625.8 (M+1). HPLC: 80.3%

Synthesis of the Title Compound; 1-Hydroxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide (11A)

Using the same reaction conditions and workup as described for the prepaqration of Example 7A, 1-benzyloxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide (0.27 g, 0.515 mmol) was reacted with $BF_3 \cdot OEt_2$ (1.94 mL, 15.45 mmol) and ethane thiol (0.3 g, 5.15 mmol). The resulting mixture was stirred at room temperature for 3 days. Purification by preparative HPLC afforded 60 mg of the product (26% yield).
$^1$HNMR (400 MHz, $CD_3OD$): δ 7.5-7.4 (d, 1H), 7.4-7.3 (d, 1H), 6.6-6.5 (t, 1H), 4.9-4.8 (t, 2H), 4.4-4.3 (t, 2H), 4.0-3.9 (s, 2H), 1.7 (s, 3H), 1.2 (t, 2H), 1.0-0.9 (t, 2H). LCMS: 98.7%, m/z=535.7 (M+1). HPLC: 99.32%

Example 12

Synthesis of 1-(3-Hydroxy-propyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide (12A)

(12A)

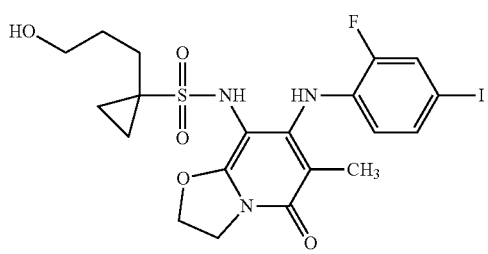

Synthesis of Intermediate 1-(3-Benzyloxy-propyl)-cyclopropanesulfonic acid [7-(2-fluoro-4-iodo-phenylamino)-6-methyl-5-oxo-2,3-dihydro-5H-oxazolo [3,2-a]pyridin-8-yl]-amide (I-12a)

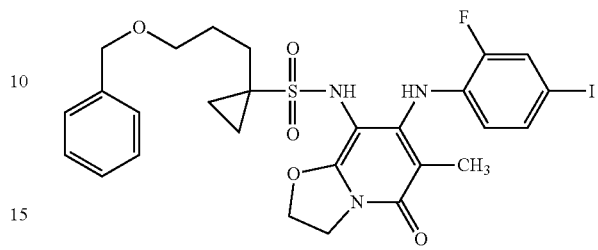

Using the same reaction conditions and workup as described for the preparation of Example 7A, 8-amino-7-(2-fluoro-4-iodo-phenylamino)-6-methyl-2,3-dihydro-oxazolo [3,2-a]pyridin-5-one (I-7f: 0.5 g, 1.246 mmol) in pyridine (5 ml) was reacted with 1-(3-benzyloxy-propyl)-cyclopropanesulfonyl chloride (0.39 mg, 1.371 mmol) to afford the crude product. Purification by column chromatography on silica gel (2% MeOH in $CHCl_3$) afforded 0.23 g of the product (28% yield). LCMS: 93.01%, m/z=654.0 (M+1). HPLC: 74.6%

Synthesis of the Title Compound; 1-(3-Hydroxy-propyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide (12A)

1-(3-Benzyloxy-propyl)cyclopropanesulfonic acid [7-(2-fluoro-4-iodo-phenylamino)-6-methyl-5-oxo-2,3-dihydro-5H-oxazolo[3,2-a]pyridin-8-yl]-amide (0.23 g, 0.352 mmol) in DCM (10 mL) was reacted with 1M $BCl_3$ (0.12 g, 1.056 mmol) at 0° C. The resulting mixture was stirred at 0° C. for 3 hours. Purification by column chromatography on silica gel (4% MeOH in $CHCl_3$) afforded 70 mg of the product (36% yield).
$^1$HNMR (400 MHz, $CD_3OD$): δ 7.5-7.4 (d, 1H), 7.4-7.3 (d, 1H), 6.5-6.4 (t, 1H), 4.9-4.8 (t, 2H), 4.4-4.3 (t, 2H), 3.6-3.5 (t, 2H), 2.1-2.0 (m, 2H), 1.75 (s, 3H), 1.7-1.6 (m, 2H), 1.2-1.1 (m, 2H), 0.9-0.8 (t, 2H). LCMS: 96.73%, m/z=563.9 (M+1). HPLC: 95.14%

Example 13

Synthesis of 3-Hydroxy-cyclobutanesulfonic acid [7-(2-fluoro-4-iodo-phenylamino)-6-methyl-5-oxo-2,3-dihydro-5H-oxazolo[3,2-a]pyridin-8-yl]-amide (13A)

(13A)

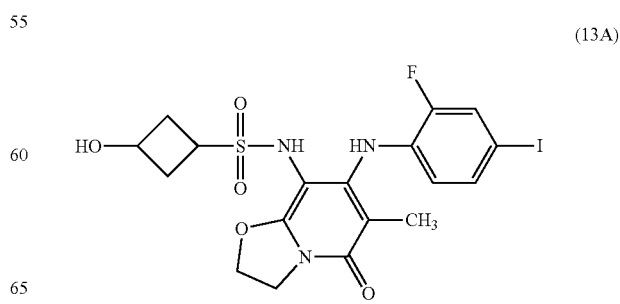

Synthesis of Intermediate 3-Benzyloxy-cyclobutane-sulfonic acid [7-(2-fluoro-4-iodo-phenylamino)-6-methyl-5-oxo-2,3-dihydro-5H-oxazolo[3,2-a]pyridin-8-yl]-amide (I-13a)

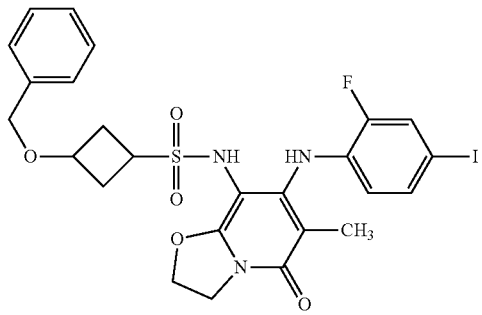 [SMILES: Cc1c(Nc2ccc(I)cc2F)c(NS(=O)(=O)C2CC(OCc3ccccc3)C2)c2n(c1=O)CCO2]

Using the same reaction conditions and workup as described for the preparation of Example 7A, 8-amino-7-(2-fluoro-4-iodo-phenylamino)-6-methyl-2,3-dihydro-oxazolo[3,2-a]pyridin-5-one (I-7f: 0.53 g, 1.0 mmol) in pyridine (4 mL) was reacted with 3-benzyloxy-cyclobutanesulfonyl chloride (0.179 mg, 1.2 mmol) to afford the crude product. Purification by column chromatography on silica gel (2% MeOH in DCM) afforded 195 mg of the product (23.8% yield).

Synthesis of the Title Compound; 3-Hydroxy-cyclobutanesulfonic acid [7-(2-fluoro-4-iodo-phenylamino)-6-methyl-5-oxo-2,3-dihydro-5H-oxazolo[3,2-a]pyridin-8-yl]-amide (13A)

3-Benzyloxy-cyclobutanesulfonic acid [7-(2-fluoro-4-iodo-phenylamino)-6-methyl-5-oxo-2,3-dihydro-5H-oxazolo[3,2-a]pyridin-8-yl]-amide (180 mg, 0.288 mmol) in DCM (10 mL) was reacted with 1M $BCl_3$ (0.86 mL, 0.864 mmol) at −78° C. The resulting mixture was stirred at room temperature for 1 hour. Purification by column chromatography on silica gel (4% MeOH in DCM), followed by preparative HPLC afforded 45 mg of the product (30% yield).

$^1$HNMR (300 MHz, $CD_3OD$): δ 7.36 (t, 1H), 6.46-6.40 (m, 1H), 4.87 (t, 2H), 4.48 (dd, 1H), 4.38 (t, 2H), 4.17-4.08 (m, 1H), 3.57-3.48 (m, 1H), 2.63-2.55 (m, 2H), 2.35-2.24 (m, 2H), 1.73 (s, 3H). LCMS: 91.1%, m/z=535.9 (M+1). HPLC: 96.2%

Example 14

Synthesis of Cyclobutanesulfonic acid [7-(2-fluoro-4-iodo-phenylamino)-6-methyl-5-oxo-2,3-dihydro-5H-oxazolo[3,2-a]pyridin-8-yl]-amide (14A)

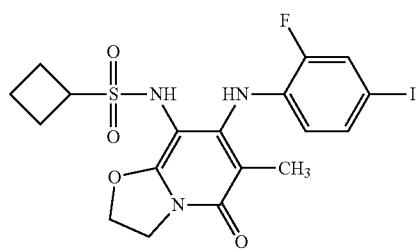

Using the same reaction conditions and workup as described for the preparation of Example 7A, 8-amino-7-(2-fluoro-4-iodo-phenylamino)-6-methyl-2,3-dihydro-oxazolo[3,2-a]pyridin-5-one (I-7f: 400 mg, 0.99 mmol) in pyridine (4 mL) was reacted with cyclobutanesulfonyl chloride (274 mg, 1.7 mmol) to afford the crude product. Purification by preparative HPLC afforded 26 mg of the product (5% yield).

$^1$HNMR (300 MHz, $CD_3OD$): δ 7.50-7.40 (d, 1H), 7.40-7.30 (d, 1H), 6.50-6.40 (t, 1H), 4.90-4.80 (t, 2H), 4.40-4.30 (t, 2H), 4.10-3.90 (m, 1H), 2.50-2.40 (m, 2H), 2.40-2.30 (m, 2H), 2.10-1.90 (m, 2H), 1.80-1.70 (s, 3H). LCMS: 96%, m/z=519.9 (M+1). HPLC: 96.5%.

Example 15

Synthesis of 3-(1,3-dihydroxypropan-2-yl)-N-(7-(2-fluoro-4-iodophenylamino)-6-methyl-5-oxo-3,5-dihydro-2H-oxazolo[3,2-a]pyridin-8-yl)cyclobutane-1-sulfonamide (15A)

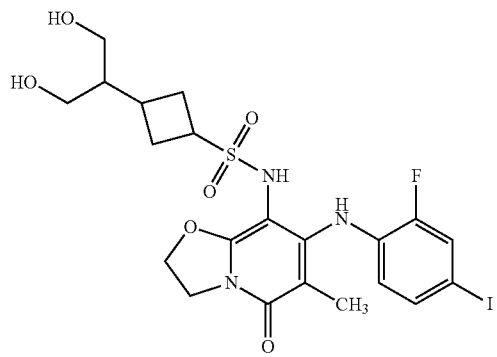

(15A)

Synthesis of Intermediate butyl 3-oxocyclobutane-1-sulfonate (I-15a)

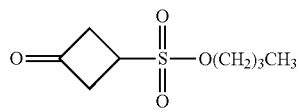

Pyridinium chloro chromate (10.3 g, 48.07 mmol) was added to a cooled solution of butyl 3-hydroxycyclobutane-1-sulfonate (5 g, 24.03 mmol) in dry DCM (50 mL) at 0° C. The resulting reaction mixture was stirred at room temperature overnight. The reaction was monitored by TLC (40% ethyl acetate in hexane). The reaction mixture was diluted with DCM, filtered and the filtrate was concentrated to afford the crude product. Purification by column chromatography on silica gel (15% ethyl acetate in hexane) afforded 2.8 g of the product (58% yield).

$^1$HNMR ($CDCl_3$, 300 MHz): δ 4.4-4.3 (t, 3H), 4.0-3.9 (m, 1H), 3.7-3.6 (m, 2H), 3.5-3.4 (m, 2H), 1.8-1.7 (q, 2H), 1.5-1.4 (q, 2H), 1.0-0.9 (t, 3H).

Synthesis of Intermediate diethyl 2-(3-(butoxysulfonyl)cyclobutylidene)malonate (I-15b)

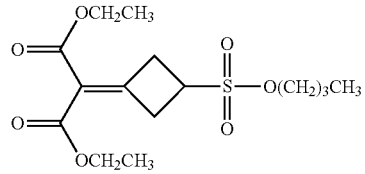

TiCl₄ (0.5 mL, 4.854 mmol) was added to a solution of THF (25 mL) and CCl₄ (5 mL) at 0° C. This was followed by the addition of butyl 3-oxocyclobutane-1-sulfonate (0.5 g, 2.42 mmol) at 0° C. and diethyl malonate (0.38 mL, 2.42 mmol). The resulting mixture was stirred at 0° C. for 5 minutes. Then pyridine (0.78 mL, 9.68 mmol) in THF (10 mL) was added and stirred at room temperature for 96 hours. The reaction was monitored by TLC (30% ethyl acetate in hexane). The reaction mixture was partitioned between water and ethyl acetate. The organic layer was washed with sodium bicarbonate solution, brine solution, dried over anhydrous Na₂SO₄ and concentrated. Purification by column chromatography on silica gel (13% ethyl acetate in hexane) afforded 200 mg of the product (25% yield).

¹HNMR (CDCl₃, 300 MHz): δ 4.3-4.2 (m, 6H), 4.0-3.9 (m, 1H), 3.7-3.5 (m, 4H), 1.8-1.7 (q, 2H), 1.5-1.4 (q, 2H), 1.3 (t, 6H), 1.0-0.9 (t, 3H).

Synthesis of Intermediate butyl 3-(1,3-dihydroxypropan-2-yl)cyclobutane-1-sulfonate (I-15c)

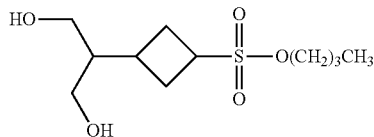

Borane-DMS (0.2 mL, 2.3 mmol) was added to a solution of diethyl 2-(3-(butoxysulfonyl)cyclobutylidene)malonate (0.2 g, 0.575 mmol) in THF (5 mL) and the resulting reaction mass was stirred at room temperature overnight. The reaction was monitored by TLC (100% ethyl acetate). The reaction mixture was quenched with 1N HCl and extracted using ethyl acetate. The organic layer was washed with brine solution, dried over anhydrous Na₂SO₄ and concentrated. Purification by column chromatography on silica gel (70% ethyl acetate in hexane) afforded 0.13 g of the product (74% yield).

¹H-NMR (CDCl₃, 300 MHz): δ 4.2 (t, 2H), 3.9-3.6 (m, 4H), 2.5-2.4 (m, 2H), 2.4-2.3 (m, 2H), 2.1-1.9 (m, 3H), 1.7-1.6 (m, 2H), 1.5-1.4 (q, 2H), 1.0-0.9 (t, 3H).

LCMS: 99%, m/z=266 (M+1)

Synthesis of butyl 3-(1,3-bis(benzyloxy)propan-2-yl) cyclobutane-1-sulfonate (I-15d)

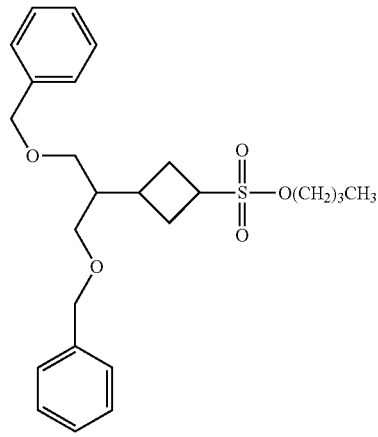

Using the same reaction conditions, procedure and work up as described Intermediate I-25a (below), butyl 3-(1,3-dihydroxypropan-2-yl)cyclobutane-1-sulfonate (0.13 g, 0.489 mmol) was reacted with benzyl bromide (0.13 mL, 1.075 mmol), 60% NaH (60 mg, 1.467 mmol) and THF (5 mL) to afford the crude product. Purification by column chromatography on silica gel (8% ethyl acetate in hexane) afforded 0.07 g of the product (78% yield).

¹HNMR (CDCl₃, 300 MHz): δ 7.4-7.2 (m, 10H), 4.5-4.4 (d, 4H), 4.2-4.1 (t, 2H), 3.5-3.4 (d, 4H), 3.6-3.8 (m, 1H), 2.5-2.3 (m, 5H), 2.0-1.9 (m, 1H), 1.7-1.6 (m, 2H), 1.4-1.3 (m, 2H), 1.0-0.9 (t, 3H). LCMS: 87%, m/z=446 (M+1)

Synthesis of Intermediate potassium 3-(1,3-bis(benzyloxy)propan-2-yl)cyclobutane-1-sulfonate (I-15d)

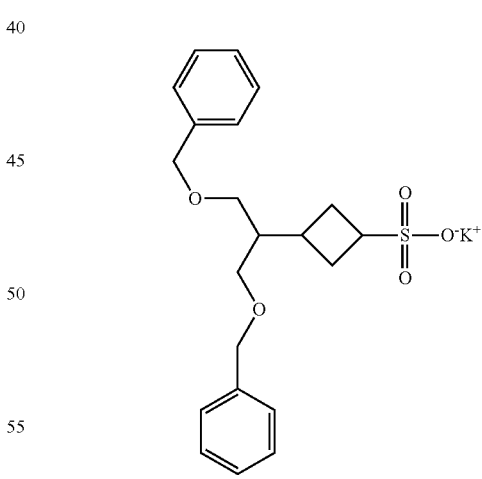

Using the same reaction conditions, procedure and work up as described Intermediate I-25b (below), butyl 3-(1,3-bis(benzyloxy)propan-2-yl)cyclobutane-1-sulfonate (0.1 g, 0.22 mmol) was reacted with KSCN (24 mg, 0.24 mmol) and DME-water mixture (2 mL) to afford 0.07 g of the product (83% yield).

¹HNMR (DMSO-d₆, 300 MHz): δ 7.4-7.2 (m, 10H), 4.4-4.3 (m, 4H), 3.4-3.3 (m, 4H), 3.0 (m, 1H), 2.1-1.9 (m, 2H), 1.9-1.6 (m, 4H)

Synthesis of Intermediate 3-(1,3-bis(benzyloxy)propan-2-yl)cyclobutane-1-sulfonyl chloride (I-15f)

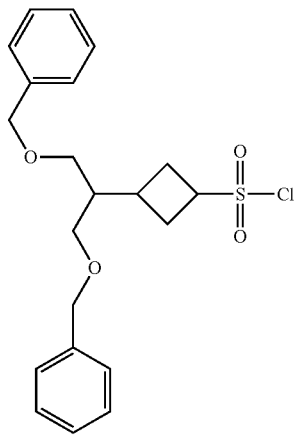 [SMILES: O=S(=O)(Cl)C1CC(C(COCc2ccccc2)COCc2ccccc2)C1]

Using the same reaction conditions, procedure and work up as described for the preparation of Intermediate I-25c (below), potassium 3-(1,3-bis(benzyloxy)propan-2-yl)cyclobutane-1-sulfonate (0.5 g, 1.168 mmol) was reacted with POCl₃ (0.22 mL, 2.336 mmol), diisopropyl ethyl amine (0.4 mL, 2.336 mmol) and DCM (20 mL) to afford the crude product. Purification by column chromatography on silica gel (8% ethyl acetate in hexane) afforded 0.32 g of the product (68% yield).

¹HNMR (CDCl₃, 300 MHz): δ 7.4-7.2 (m, 10H), 4.5-4.4 (m, 4H), 4.2 (m, 1H), 3.5-3.4 (m, 4H), 2.6-2.4 (m, 4H), 2.1-1.9 (m, 1H)

Synthesis of Intermediate 3-(1,3-bis(benzyloxy)propan-2-yl)-N-(7-(2-fluoro-4-iodophenylamino)-6-methyl-5-oxo-3,5-dihydro-2H-oxazolo[3,2-a]pyridin-8-yl)cyclobutane-1-sulfonamide (I-15q)

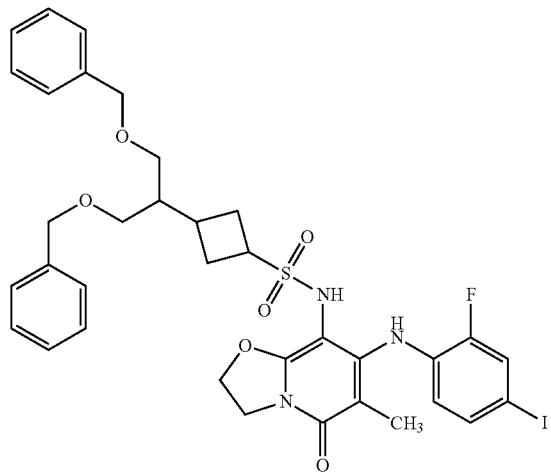 [SMILES: Cc1c(Nc2ccc(I)cc2F)c(NS(=O)(=O)C2CC(C(COCc3ccccc3)COCc3ccccc3)C2)c2n(c1=O)CCO2]

Using the same reaction conditions and procedure as described for the preparation of Example 7A, 8-Amino-7-(2-fluoro-4-iodo-phenylamino)-6-methyl-2,3-dihydro-oxazolo[3,2-a]pyridin-5-one (I-7f: 0.22 g, 0.539 mmol) was reacted with 3-(1,3-bis(benzyloxy)propan-2-yl)cyclobutane-1-sulfonyl chloride (0.21 g, 0.539 mmol) in dry pyridine (2 mL) to afford the crude product. Purification by column chromatography on silica gel (80% ethyl acetate in hexane) afforded 0.3 g of the product (71% yield). LCMS: 80%, m/z=773 (M+1)

Synthesis of the Title Compound; 3-(1,3-dihydroxypropan-2-yl)-N-(7-(2-fluoro-4-iodophenylamino)-6-methyl-5-oxo-3,5-dihydro-2H-oxazolo[3,2-a]pyridin-8-yl)cyclobutane-1-sulfonamide (15A)

3-(1,3-Bis(benzyloxy)propan-2-yl)-N-(7-(2-fluoro-4-iodophenylamino)-6-methyl-5-oxo-3,5-dihydro-2H-oxazolo[3,2-a]pyridin-8-yl)cyclobutane-1-sulfonamide (0.3 g, 0.388 mmol) was reacted with 1M BCl₃ (1.1 mL, 1.164 mmol) and DCM (10 mL) at 0° C. for 30 minutes to afford the crude product. Purification by column chromatography on silica gel (8% methanol in chloroform) afforded 60 mg of the product (26% yield).

¹HNMR (300 MHz, CD₃OD): δ 7.5 (d, 1H), 7.4 (d, 1H), 6.5 (t, 1H), 4.4-4.3 (t, 2H), 3.9 (m, 1H), 3.6-3.5 (m, 5H), 2.5-2.3 (m, 2H), 2.3-2.2 (m, 3H), 1.7 (s, 3H), 1.7-1.6 (m, 2H). LCMS: 90.98%, m/z=593.9 (M+1). HPLC: 95.12%

Example 16

Synthesis of N-(7-(2-fluoro-4-iodophenylamino)-6-methyl-5-oxo-3,5-dihydro-2H-oxazolo[3,2-a]pyridin-8-yl)-1-(3-methyloxetan-3-yl)methanesulfonamide (16A)

(16A)

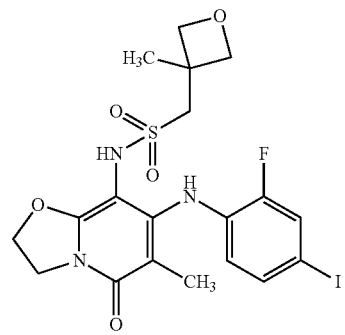

Synthesis of Intermediate (3-methyloxetan-3-yl)methyl 4-methylbenzenesulfonate (I-16a)

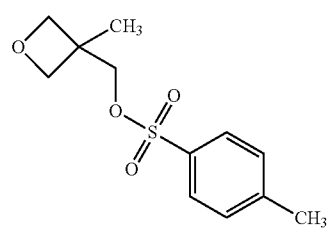 [SMILES: Cc1ccc(S(=O)(=O)OCC2(C)COC2)cc1]

p-Toluene sulfonyl chloride (5.6 g, 29.41 mmol) was added to a cooled solution of (3-methyloxetan-3-yl)methanol (2 g, 19.60 mmol) in pyridine (25 mL) at 0° C. and the resulting reaction mass was stirred at 0° C. for 2 hours. The reaction was monitored by TLC (20% ethyl acetate in hexane). The reaction mass was poured into ice-water, stirred for 30 minutes, the solid formed was collected by filtration, washed with water and dried under reduced pressure to afford 2.5 g of the product (50% yield).

$^1$HNMR (CDCl$_3$, 300 MHz): δ 7.8 (d, 2H), 7.4 (d, 2H), 4.4 (m, 4H), 4.1 (s, 2H), 2.5 (s, 3H), 1.3 (s, 3H). LCMS: 99.13%, m/z=256 (M+1)

Synthesis of Intermediate
3-methyl-3-(thiocyanatomethyl)oxetane (I-16b)

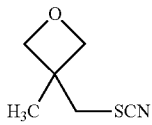

KSCN (0.75 g, 7.81 mmol) was added to a solution of (3-methyloxetan-3-yl)methyl 4-methylbenzenesulfonate (1 g, 3.90 mmol) in ethanol (25 mL) and the resulting reaction mass was heated at 85° C. overnight. The reaction was monitored by TLC (30% ethyl acetate in hexane). The reaction mass was concentrated under reduced pressure to afford 1.7 g of the crude product which was used for the next step without further purification.

Synthesis of Intermediate
(3-methyloxetan-3-yl)methanesulfonyl chloride
(I-16c)

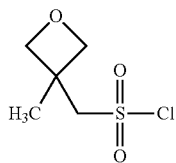

Chlorine gas was purged through a cooled solution of 3-methyl-3-(thiocyanatomethyl)oxetane (1.7 g) in water (10 mL) at 0° C. for 30 minutes. The reaction was monitored by TLC (30% ethyl acetate in hexane). The reaction mass was extracted using ether. The ether layer was washed with sodium bisulphate solution, sodium bicarbonate solution, dried over anhydrous sodium sulfate and concentrated under reduced pressure to afford 0.3 g of the crude product which was used for the next step without further purification.

$^1$HNMR (CDCl$_3$, 300 MHz): δ 4.7 (d, 2H), 4.5-4.4 (d, 2H), 4.2 (s, 2H), 1.7 (s, 3H).

Synthesis of the Title Compound; N-(7-(2-fluoro-4-iodophenylamino)-6-methyl-5-oxo-3,5-dihydro-2H-oxazolo[3,2-a]pyridin-8-yl)-1-(3-methyloxetan-3-yl)methanesulfonamide (16A)

Using the same reaction conditions and procedure as described for the preparation of Example 7A, 8-Amino-7-(2-fluoro-4-iodo-phenylamino)-6-methyl-2,3-dihydro-oxazolo[3,2-a]pyridin-5-one (I-7f: 0.2 g, 0.499 mmol) was reacted with (3-methyloxetan-3-yl)methanesulfonyl chloride (0.13 g, 0.748 mmol) in dry pyridine (3 mL) to afford the crude product. Purification by preparative HPLC afforded 25 mg of the product (9% yield).

$^1$HNMR (300 MHz, CD$_3$OD): δ 7.5 (d, 1H), 7.4 (d, 1H), 6.5 (t, 1H), 4.9-4.8 (t, 2H), 4.7 (d, 2H), 4.40-4.35 (t, 2H), 4.3 (d, 2H), 3.6 (s, 2H), 1.8 (s, 3H), 1.6 (s, 3H). LCMS: 92.56%, m/z=549.5 (M+1). HPLC: 92.40%

Examples 17 and 18

Synthesis of N-(7-(2-fluoro-4-iodophenylamino)-6-methyl-5-oxo-3,5-dihydro-2H-oxazolo[3,2-a]pyridin-8-yl)-2-(oxetan-3-yl)ethanesulfonamide (17A)

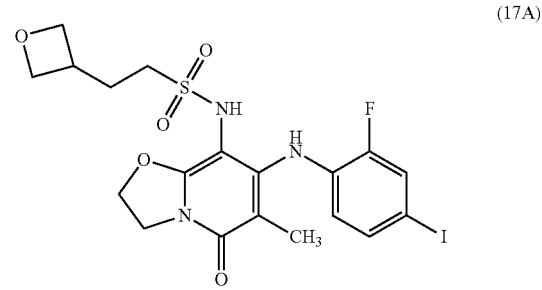

(17A)

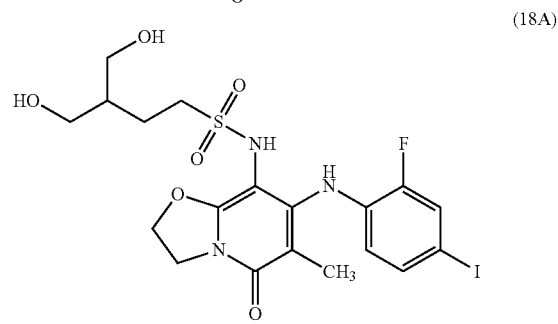

(18A)

Synthesis of Intermediate 2-(oxetan-3-yl)ethyl 4-methylbenzenesulfonate (I-17a)

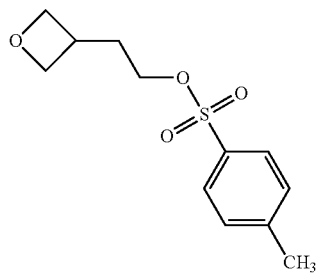 [SMILES: Cc1ccc(S(=O)(=O)OCCC2COC2)cc1]

Using the same reaction conditions and procedure as described for the preparation of Intermediate (I-16a), 2-(oxetan-3-yl)ethanol (1 g, 6.944 mmol) was reacted with p-Toluene sulfonyl chloride (1.9 g, 10.416 mmol) in dry pyridine (10 mL) to afford the crude product. The reaction mass was poured into ice-water and extracted using ethyl acetate. The organic layer was washed with 1N HCl, brine solution, dried over anhydrous sodium sulfate and concentrated under reduced pressure to afford the crude product. Purification by column chromatography on silica gel (20% ethyl acetate in hexane) afforded 1 g of the product (40% yield).

¹HNMR (CDCl₃, 300 MHz): δ 7.8 (d, 2H), 7.4 (d, 2H), 4.7 (t, 2H), 4.4 (t, 2H), 4.0 (t, 2H), 3.1-3.0 (m, 1H), 2.5 (s, 3H), 2.1-2.0 (m, 2H)

Synthesis of Intermediate
3-(2-thiocyanatoethyl)oxetane (I-17b)

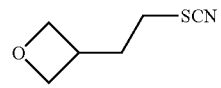

Using the same reaction conditions, procedure and work up as described for the preparation of Intermediate (I-16b), 2-(oxetan-3-yl)ethyl 4-methyl-benzenesulfonate (1 g, 3.90 mmol) was reacted with KSCN (0.75 g, 7.81 mmol) in ethanol (20 mL) to afford 1.7 g of the crude product which was used for the next step without further purification.

Synthesis of Intermediate
2-(oxetan-3-yl)ethanesulfonyl chloride (I-17c)

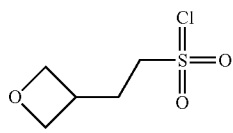

Using the same reaction conditions, procedure and work up as described for the preparation of Intermediate (I-16c), 3-(2-thiocyanatoethyl)oxetane (1 g) in water (10 mL) was purged with chlorine gas for 30 minutes to afford 0.4 g of the product (56% yield) which was for next reaction with purification and characterization.

Synthesis of the Title Compound; N-(7-(2-fluoro-4-iodophenylamino)-6-methyl-5-oxo-3,5-dihydro-2H-oxazolo[3,2-a]pyridin-8-yl)-2-(oxetan-3-yl)ethane-sulfonamide (17A)

Using the same reaction conditions and procedure as described for the preparation of Example 7A, 8-Amino-7-(2-fluoro-4-iodo-phenylamino)-6-methyl-2,3-dihydro-oxazolo[3,2-a]pyridin-5-one (I-7f: 0.2 g, 0.673 mmol) was reacted with 2-(oxetan-3-yl)ethanesulfonyl chloride (0.18 g, 1.009 mmol) in dry pyridine (3 mL) to afford the crude product. Purification by preparative HPLC, followed by flash column chromatography (3% methanol in chloroform) afforded 20 mg of the compound (17A) (9% yield) and 3 mg of the hydrolyzed by-product (compound (17B).

¹H-NMR (300 MHz, CD₃OD): δ 7.5 (d, 1H), 7.4 (d, 1H), 6.4 (t, 1H), 4.9-4.8 (m, 4H), 4.4 (m, 4H), 3.1 (m, 3H), 2.2 (m, 2H), 1.8 (s, 3H). LCMS: 100%, m/z=549.8 (M+1). HPLC: 95.97%

By-Product of Example 17A: N-(7-(2-fluoro-4-iodophenylamino)-6-methyl-5-oxo-3,5-dihydro-2H-oxazolo[3,2-a]pyridin-8-yl)-4-hydroxy-3-(hydroxymethyl)butane-1-sulfonamide (18A)

¹HNMR (300 MHz, CD₃OD): δ 7.5 (d, 1H), 7.4 (d, 1H), 6.5 (t, 1H), 4.8 (t, 2H), 4.4 (t, 2H), 3.6-3.4 (m, 4H), 3.2 (m, 2H), 1.9 (m, 2H), 1.8 (s, 3H), 1.75 (m, 1H). LCMS: 89%, m/z=568 (M+1). HPLC: 90.96%

Example 19

Synthesis of Cyclopropanesulfonic acid [7-(2-fluoro-4-iodo-phenylamino)-6-methyl-5-oxo-2,3-dihydro-5H-thiazolo[3,2-a]pyridin-8-yl]-amide (19A)

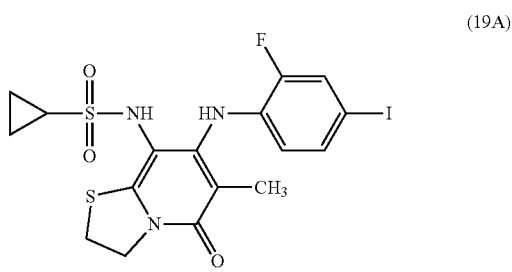 [SMILES: Cc1c(Nc2ccc(I)cc2F)c(NS(=O)(=O)C2CC2)c2n(c1=O)CCS2]

Synthesis of Intermediate
2-Nitromethylene-thiazolidine (I-19a)

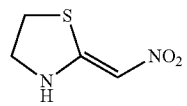

TEA (1.8 mL, 13.20 mmol) was added to a solution of 1,1-bis-methylsulfanyl-2-nitro-ethene (I-1b: 1.45 g, 8.802 mmol) and 2-amino-ethanethiol (1 g, 8.802 mmol) in ethanol (20 mL). The resulting mixture was heated to reflux for 3 hours. The reaction mixture was monitored by TLC (70% ethylacetate in hexane). The reaction mixture was concentrated to afford the crude product. Purification by column chromatography on silica gel (70% ethylacetate in hexane) afforded 0.6 g of the product (31% yield).

¹HNMR (300 MHz, DMSO-D₆): δ 9.2-9.1 (br s, 1H), 7.2-7.1 (br s, 1H), 4.0-3.6 (d, 2H), 3.5-3.1 (d, 2H). LCMS purity: 99.93%, m/z=147 (M+1)

Synthesis of Intermediate 7-Hydroxy-6-methyl-8-nitro-2,3-dihydro-thiazolo[3,2-a]pyridin-5-one (I-19b)

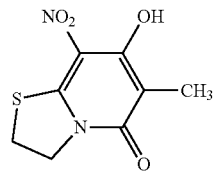

2-Nitromethylene-thiazolidine (7.3 g, 50 mmol) and 2-methyl-malonic acid bis-(2,4,6-trichloro-phenyl) ester (23.8 g, 50 mmol) in xylene (80 mL) was taken in a reaction flask and the flask was heated to reflux for 3 hours. The reaction mixture was monitored by TLC (100% ethylacetate). The reaction mixture was cooled, concentrated and partitioned between DCM and water. The organic layer was washed with water, brine solution, dried over Na$_2$SO$_4$ and concentrated. The crude product was kept at 0° C. for overnight. The solid formed was collected and washed with hexane and ether to afford 5.3 g of the product (46% yield).

$^1$HNMR (300 MHz, CDCl$_3$): δ 11.2 (s, 1H), 4.7-4.6 (t, 2H), 3.5-3.4 (t, 2H), 2.1-2.0 (s, 3H). LCMS: 100%, m/z=229(M+1)

Synthesis of Intermediate Trifluoro-methanesulfonic acid 6-methyl-8-nitro-5-oxo-2,3-dihydro-5H-thiazolo[3,2-a]pyridin-7-yl ester (I-19c)

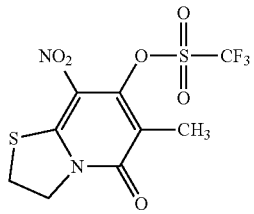 [SMILES: Cc1c(OS(=O)(=O)C(F)(F)F)c([N+](=O)[O-])c2n(c1=O)CCS2]

Triflic anhydride (3.4 g, 12.06 mmol) was added to a stirred solution of 7-hydroxy-6-methyl-8-nitro-2,3-dihydro-thiazolo[3,2-a]pyridin-5-one (2.5 g, 10.96 mmol) and TEA (2.3 mL, 16.44 mmol) in DCM (20 mL) at −70° C. The resulting mixture was stirred at −70° C. to −50° C. for 2 hours. The reaction mixture was monitored by TLC (50% ethylacetate in hexane). The reaction mixture was diluted DCM and quenched with bicarbonate solution. The organic layer was washed with brine solution, dried over Na$_2$SO$_4$ and concentrated. Purification by column chromatography on silica gel (30% ethylacetate in hexane) afforded 0.9 g of the product (38% yield).

$^1$HNMR (300 MHz, CDCl$_3$): δ 4.7-4.6 (t, 2H), 3.5-3.4 (t, 2H), 2.1-2.0 (s, 3H)

LCMS: 100%, m/z=361(M+1)

Synthesis of Intermediate 7-(2-Fluoro-4-trimethylsilanyl-phenylamino)-6-methyl-8-nitro-2,3-dihydro-thiazolo[3,2-a]pyridin-5-one (I-19d)

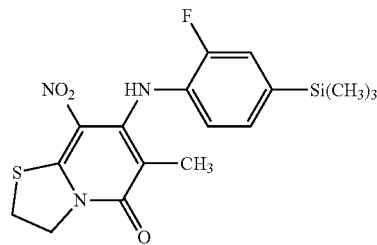

Trifluoro-methanesulfonic acid 6-methyl-8-nitro-5-oxo-2,3-dihydro-5H-thiazolo[3,2-a]pyridin-7-yl ester (0.9 g, 2.5 mmol) was reacted with 2-fluoro-4-trimethylsilanyl-phenylamine (0.5 g, 2.75 mmol), Pd(dba)$_3$ (138 mg, 0.15 mmol), potassium phosphate (0.7 g, 3.75 mmol) and xantphos (87 mg, 0.15 mmol) in toluene (30 mL) at 110° C. for 3 hours to afford the crude product. Purification by column chromatography on silica gel (30% ethylacetate in hexane) afforded 0.75 g of the product (76% yield).

$^1$HNMR (300 MHz, CDCl$_3$): δ 9.0-8.9 (br s, 1H), 7.3-7.1 (m, 2H), 6.8-6.6 (t, 1H), 4.7-4.5 (t, 2H), 3.4-3.3 (t, 2H), 1.8-1.7 (s, 3H), 0.3-0.2 (s, 9H)

LCMS: 97.55%, m/z=393.9 (M+1)

Synthesis of Intermediate 7-(2-Fluoro-4-iodo-phenylamino)-6-methyl-8-nitro-2,3-dihydro-thiazolo[3,2-a]pyridin-5-one (I-19e)

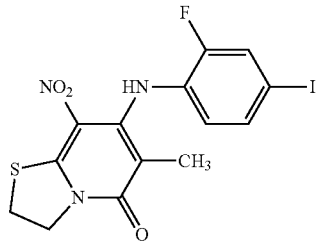 [SMILES: Cc1c(Nc2ccc(I)cc2F)c([N+](=O)[O-])c2n(c1=O)CCS2]

7-(2-Fluoro-4-trimethylsilanyl-phenylamino)-6-methyl-8-nitro-2,3-dihydro-thiazolo[3,2-a]pyridin-5-one (0.5 g, 1.27 mmol) in DCM (10 mL) was added to silver tetrafluoroborate (0.74 g, 3.81 mmol) in DCM (10 mL) previously degassed with nitrogen at −60° C. and the resulting mixture was stirred at −60° C. for 30 minutes. This was followed by the addition of iodine monochloride (1.3 mL, 1.399 mmol) and continued stirring for a further 30 minutes at −60° C. to −50° C. The reaction was monitored by TLC (50% ethylacetate in hexane). The reaction mixture was diluted with DCM, quenched with sodium thiosulphate solution, filtered through celite and the filtrate was extracted with DCM. The organic layer was washed with NH$_3$ solution, brine solution, dried over Na$_2$SO$_4$ and concentrated. Purification by column chromatography on silica gel (40% ethylacetate in hexane) afforded 0.45 g of the product (80% yield).

$^1$HNMR (300 MHz, CDCl$_3$): δ 8.9 (s, 1H), 7.5-7.4 (d, 1H), 7.4-7.3 (d, 1H), 6.5 (t, 1H), 4.8-4.6 (t, 2H), 3.5-3.3 (t, 2H), 1.8-1.7 (s, 3H)

LCMS: 98.6%, m/z=445.9 (M−1)

Synthesis of Intermediate 8-Amino-7-(2-fluoro-4-iodo-phenylamino)-6-methyl-2,3-dihydro-thiazolo[3,2-a]pyridin-5-one (I-19f)

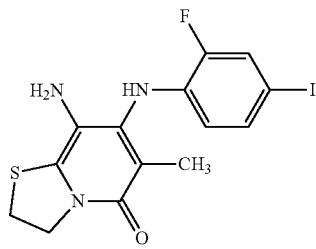

Concentrated HCl (0.3 mL) and SnCl$_2$.H$_2$O (0.15 g, 0.671 mmol) were added to 7-(2-fluoro-4-iodo-phenylamino)-6-methyl-8-nitro-2,3-dihydro-thiazolo[3,2-a]pyridin-5-one (0.1 g, 0.22 mmol) in ethanol (3 mL). The resulting mixture was heated to reflux for 2 hours. The reaction was monitored by TLC (100% ethylacetate). The reaction mixture was cooled to room temperature, diluted with DCM, basified with saturated bicarbonate solution and filtered through celite. The filtrate was extracted with DCM. The organic layer was washed with brine solution, dried over Na$_2$SO$_4$ and concentrated to afford 0.09 g of the product (90% yield).

$^1$HNMR (300 MHz, CDCl$_3$): δ 7.4-7.3 (d, 1H), 7.2-7.1 (d, 1H), 6.3-6.2 (t, 1H), 5.8 (s, 1H), 4.5 (t, 2H), 3.4-3.3 (t, 2H), 2.8-2.6 (br s, 2H), 1.8-1.7 (s, 3H).

LCMS: 89.9%, m/z=417.9 (M+1)

Synthesis of the Title Compound; Cyclopropanesulfonic acid [7-(2-fluoro-4-iodo-phenylamino)-6-methyl-5-oxo-2,3-dihydro-5H-thiazolo[3,2-a]pyridin-8-yl]-amide (19A)

Cyclopropane sulfonyl chloride (34 mg, 0.23 mmol) was added to a solution of 8-amino-7-(2-fluoro-4-iodo-phenylamino)-6-methyl-2,3-dihydro-thiazolo[3,2-a]pyridin-5-one (0.09 g, 0.21 mmol) in pyridine (1 mL) at 0° C. The resulting mixture was stirred at room temperature overnight. The reaction was monitored by TLC (5% MeOH in CHCl$_3$). The reaction mixture was partitioned between ethylacetate and water. The organic layer was washed with 2N HCl, brine solution, dried over Na$_2$SO$_4$ and concentrated. Purification by column chromatography on silica gel (1% MeOH in CHCl$_3$), followed by preparative HPLC afforded 25 mg of the product (22% yield).

$^1$HNMR (300 MHz, CD$_3$OD): δ 7.5-7.4 (d, 1H), 7.4-7.3 (d, 1H), 6.4-6.2 (t, 1H), 4.6-4.5 (t, 2H), 3.6-3.5 (t, 2H), 2.7-2.6 (m, 1H), 1.8-1.7 (s, 3H), 1.1-1.0 (m, 4H). LCMS: 100%, m/z=522 (M+1) HPLC: 98.8%

Example 20

Synthesis of 1-(2,3-Dihydroxy-propyl)-cyclopropanesulfonic acid [7-(2-fluoro-4-iodo-phenylamino)-6-methyl-5-oxo-2,3-dihydro-5H-thiazolo[3,2-a]pyridin-8-yl]-amide (20A)

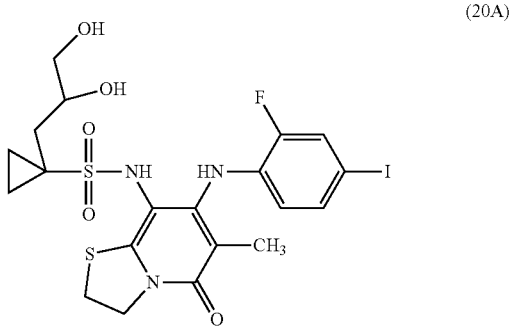 [SMILES: Cc1c(Nc2ccc(I)cc2F)c(NS(=O)(=O)C2(CC(O)CO)CC2)c2n(c1=O)CCS2]

(20A)

Synthesis of Intermediate 1-Allyl-cyclopropanesulfonic acid [7-(2-fluoro-4-iodo-phenylamino)-6-methyl-5-oxo-2,3-dihydro-5H-thiazolo[3,2-a]pyridin-8-yl]-amide (I-20a)

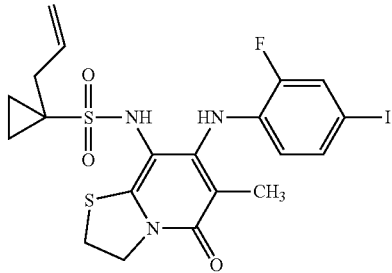 [SMILES: C=CCC1(S(=O)(=O)Nc2c(Nc3ccc(I)cc3F)c(C)c(=O)n3c2SCC3)CC1]

8-Amino-7-(2-fluoro-4-iodo-phenylamino)-6-methyl-2,3-dihydro-thiazolo[3,2-a]pyridin-5-one (I-19f: 0.3 g, 0.719 mmol) in pyridine (3 mL) was reacted with 1-allyl-cyclopropane sulfonyl chloride (0.15 g, 0.863 mmol) to afford the crude product. Purification by column chromatography on silica gel (40% ethylacetate in hexane) afforded 0.21 g of the product (52% yield).

$^1$H-NMR (300 MHz, CDCl$_3$): δ 7.4-7.3 (d, 1H), 7.3-7.2 (d, 1H), 6.8 (br s, 1H), 6.3-6.2 (t, 1H), 5.85-5.7 (m, 1H), 5.65 (s, 1H), 5.2-5.15 (d, 1H), 5.15 (s, 1H), 4.6-4.5 (t, 2H), 3.5-3.4 (t, 2H), 2.8-2.7 (d, 2H), 1.8-1.7 (t, 3H), 0.9-0.8 (m, 4H).

LCMS: 100%, m/z=562 (M+1)

Synthesis of the Title Compound; 1-(2,3-Dihydroxy-propyl)-cyclopropanesulfonic acid [7-(2-fluoro-4-iodo-phenylamino)-6-methyl-5-oxo-2,3-dihydro-5H-thiazolo[3,2-a]pyridin-8-yl]-amide (20A)

Using the same reaction conditions and workup as described for the preparation of Intermediate (I-4d) in Example 4, 1-allyl-cyclopropanesulfonic acid [7-(2-fluoro-4-iodo-phenylamino)-6-methyl-5-oxo-2,3-dihydro-5H-thiazolo[3,2-a]pyridin-8-yl]-amide (0.05 g, 0.089 mmol) in THF (2 mL) was reacted with N-methoxy morpholin-N-oxide (10.5 mg, 0.089 mmol) and osmium tetra oxide (2.2 mg, 0.0089 mmol) to afford the crude product. Purification by column chromatography on silica gel (2% MeOH in CHCl$_3$), followed by preparative HPLC afforded 12 mg of the product (22% yield).

$^1$HNMR (300 MHz, DMSO-D$_6$): δ 8.9-8.8 (s, 1H), 7.6-7.5 (d, 1H), 7.4-7.3 (d, 1H), 7.3-7.2 (s, 1H), 6.4-6.3 (t, 1H), 4.5-4.3 (t, 2H), 3.7-3.6 (m, 1H), 3.5-3.2 (m, 6H), 2.3-2.2 (d, 1H), 1.8-1.6 (m, 1H), 1.6 (s, 3H), 1.2-1.0 (m, 4H).

LCMS: 91.7%, m/z=595.9 (M+1). HPLC: 90.8%

Example 21

Synthesis of 2-Hydroxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide (21A)

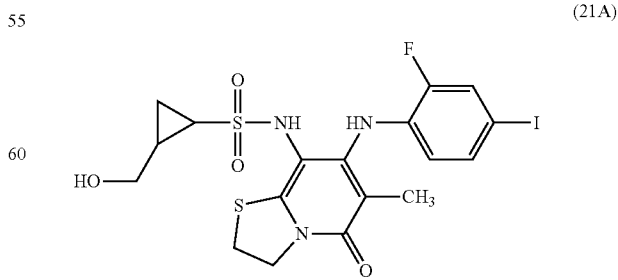

(21A)

Synthesis of Intermediate 2-Benzyloxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide (I-21a)

Example 22

Synthesis of 1-Hydroxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide (22A)

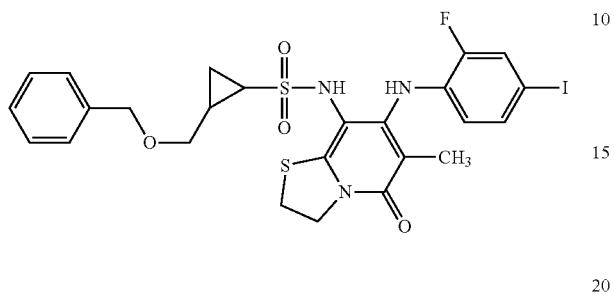

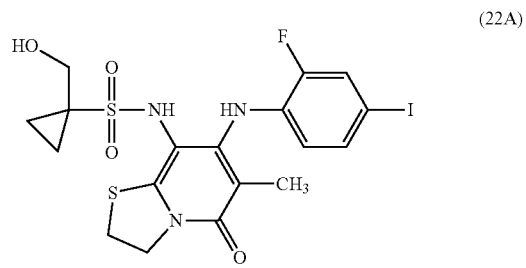 [SMILES: Cc1c(Nc2ccc(I)cc2F)c(NS(=O)(=O)C2(CO)CC2)c2n(c1=O)CCS2]

Using the same reaction conditions and workup as described for the preparation of Example 19A, 8-amino-7-(2-fluoro-4-iodo-phenylamino)-6-methyl-2,3-dihydro-thiazolo[3,2-a]pyridin-5-one (I-19f: 0.2 g, 0.048 mmol) in pyridine (2 mL) was reacted with 2-benzyloxymethyl-cyclopropanesulfonyl chloride (0.13 g, 0.52 mmol) to afford the crude product. Purification by column chromatography on silica gel (60% ethylacetate in hexane) afforded 0.26 g of the product (86% yield).

$^1$HNMR (300 MHz, CDCl$_3$): δ 7.4-7.2 (m, 7H), 7.0-6.9 (s, 1H), 6.3-6.2 (t, 1H), 5.9 (s, 1H), 4.6-4.4 (m, 4H), 3.6-3.3 (m, 2H), 2.6-2.5 (m, 1H), 1.9-1.8 (m, 1H), 1.7 (s, 3H), 1.4-1.2 (m, 1H), 1.2-1.1 (m, 2H), 0.9-0.8 (m, 1H).

LCMS: 100%, m/z=642 (M+1); HPLC: 92.8%

Synthesis of Intermediate 1-Benzyloxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide (I-22a)

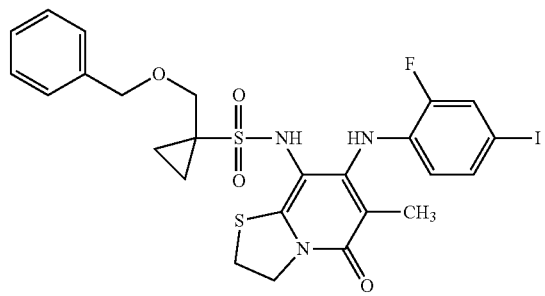

Using the same reaction conditions and workup as described for the preparation of Example 19A, 8-amino-7-(2-fluoro-4-iodo-phenylamino)-6-methyl-2,3-dihydro-thiazolo[3,2-a]pyridin-5-one (I-19f: 0.2 g, 0.048 mmol) in pyridine (2 mL) was reacted with 1-benzyloxymethyl-cyclopropanesulfonyl chloride (137 mg, 0.52 mmol) to afford the crude product. Purification by column chromatography on silica gel (50% ethylacetate in hexane) afforded 0.21 g of the product (70% yield).

$^1$HNMR (300 MHz, CDCl$_3$): δ 7.4-7.3 (d, 1H), 7.25-7.1 (d, 7H), 6.3-6.2 (t, 1H), 6.1 (s, 1H), 4.6-4.5 (t, 4H), 3.9-3.8 (s, 2H), 3.4-3.3 (t, 2H), 1.7 (s, 3H), 1.5-1.4 (t, 1H), 1.3-1.2 (t, 2H), 1.0-0.9 (t, 1H). LCMS: 100%, m/z=642 (M+1). HPLC: 90.5%

Synthesis of the Title Compound; 2-Hydroxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide (21A)

2-fluoro-4-iodo-phenylamino)-6-methyl-5-oxo-2,3-dihydro-5H-thiazolo[3,2-a]pyridin-8-yl]-amide (0.1 g, 0.156 mmol) was added to a stirred solution of BF$_3$.OEt$_2$(0.39 mL, 3.12 mmol) in ethane thiol (0.1 mL, 1.56 mmol) under nitrogen atmosphere. The resulting mixture was stirred at room temperature for 2 hours, followed by heating for 4 hours at 40° C. The reaction was monitored by TLC (10% MeOH in DCM). The reaction mixture was quenched in saturated NaHCO$_3$ solution and extracted with DCM. The organic layer was washed with brine, dried over Na$_2$SO$_4$ and concentrated. Purification by column chromatography on silica gel (4% MeOH in DCM) afforded 25 mg of the product (31% yield).

$^1$HNMR (300 MHz, CD$_3$OD): δ 7.5-7.45 (d, 1H), 7.4-6.3 (d, 1H), 6.4-6.3 (t, 1H), 4.6-4.5 (m, 2H), 3.6-3.5 (m, 4H), 2.6-2.5 (m, 1H), 1.8-1.7 (s, 3H), 1.7-1.6 (m, 1H), 1.3-1.2 (m, 1H), 1.1-1.0 (m, 1H). LCMS: 96.2%, m/z=551.9 (M+1). HPLC: 97.19%

Synthesis of the Title Compound; 1-Hydroxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide (22A)

Using the same reaction conditions and workup as described for the preparation of Example 21A, 1-benzyloxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide (0.2 g, 0.321 mmol) was reacted with BF$_3$OEt$_2$(0.79 mL, 6.24 mmol) and ethane thiol (0.2 mL, 3.21 mmol). The resulting mixture was stirred at 40° C. for 6 hours. Purification by column chromatography on silica gel (2% MeOH in CHCl$_3$) afforded 100 mg of the product (55% yield).

$^1$HNMR (300 MHz, CD$_3$OD): δ 7.6-7.3 (dd, 2H), 6.6-6.5 (t, 1H), 4.6-4.5 (t, 2H), 4.0-3.8 (s, 2H), 3.5-3.4 (t, 2H), 1.65 (s, 3H), 1.4-1.2 (m, 2H), 0.9-0.8 (t, 2H).

LCMS: 100%, m/z=551.7 (M+1). HPLC: 94.13%

Example 23

Synthesis of N-[7-(2-Fluoro-4-iodo-phenylamino)-6-methyl-5-oxo-2,3-dihydro-5H-thiazolo[3,2-a]pyridin-8-yl]-dimethylaminosulfonamide (23A)

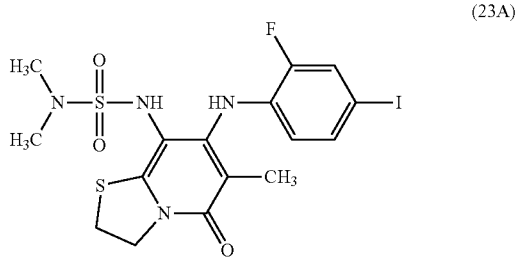 [SMILES: Cc1c(Nc2ccc(I)cc2F)c(NS(=O)(=O)N(C)C)c2n(c1=O)CCS2]

(23A)

Using the same reaction conditions and workup as described for the preparation of Example 19A, 8-amino-7-(2-fluoro-4-iodo-phenylamino)-6-methyl-2,3-dihydro-thiazolo[3,2-a]pyridin-5-one (I-19f: 0.2 g, 0.048 mmol) in pyridine (2 mL) was reacted with dimethyl aminosulfonyl chloride (76 mg, 0.528 mmol) to afford the crude product. Purification by column chromatography on silica gel (2% MeOH in CHCl$_3$) afforded 0.08 g of the product (32% yield).

$^1$HNMR (300 MHz, DMSO-D$_6$): δ 8.8 (s, 1H), 7.6-7.5 (d, 1H), 7.4-7.3 (d, 1H), 7.3-7.2 (s, 1H), 6.4-6.2 (t, 1H), 4.5-4.3 (t, 2H), 3.5-3.4 (t, 2H), 2.9-2.6 (s, 6H), 1.65-1.55 (s, 3H). LCMS: 98.4%, m/z=524.9 (M+1). HPLC: 92.8%

Example 24

Synthesis of Cyclopentanesulfonic acid [7-(2-fluoro-4-iodo-phenylamino)-6-methyl-5-oxo-2,3-dihydro-5H-thiazolo[3,2-a]pyridin-8-yl]-amide (24A)

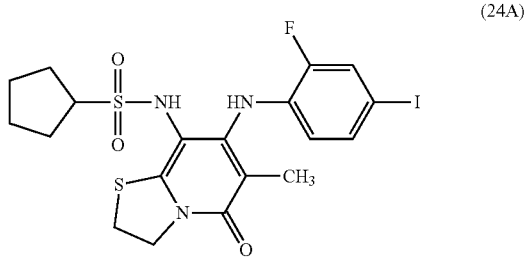 [SMILES: Cc1c(Nc2ccc(I)cc2F)c(NS(=O)(=O)C2CCCC2)c2n(c1=O)CCS2]

(24A)

Using the same reaction conditions and workup as described for the preparation of Example 19A, 8-amino-7-(2-fluoro-4-iodo-phenylamino)-6-methyl-2,3-dihydro-thiazolo[3,2-a]pyridin-5-one (I-19f: 0.2 g, 0.048 mmol) in pyridine (2 mL) was reacted with cyclopentanesulfonyl chloride (106 mg, 0.528 mmol) to afford the crude product. Purification by preparative HPLC afforded 0.03 g of the product (11% yield).

$^1$HNMR (300 MHz, CD$_3$OD): δ 7.5-7.4 (d, 1H), 7.4-7.3 (d, 1H), 6.4-6.3 (t, 1H), 4.6-4.5 (t, 2H), 3.7-3.6 (t, 1H), 3.6-3.5 (t, 2H), 2.2-2 (s, 4H), 1.8-1.55 (m, 7H). LCMS: 100%, m/z=549.8 (M+1). HPLC: 92.41%

Example 25

Synthesis of 3-Hydroxy-cyclobutanesulfonic acid [7-(2-fluoro-4-iodo-phenylamino)-6-methyl-5-oxo-2,3-dihydro-5H-thiazolo[3,2-a]pyridin-8-yl]-amide (25A)

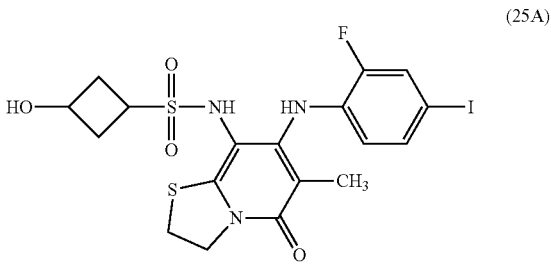 [SMILES: Cc1c(Nc2ccc(I)cc2F)c(NS(=O)(=O)C2CC(O)C2)c2n(c1=O)CCS2]

(25A)

Synthesis of Intermediate butyl 3-(benzyloxy)cyclobutane-1-sulfonate (I-25a)

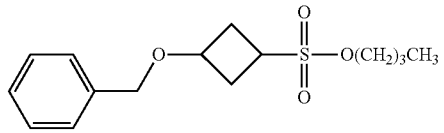

60% NaH (0.95 g, 2.52 (CH$_2$)$_2$CH$_3$ mmol) was added to a cooled solution of butyl 3-hydroxycyclobutane-1-sulfonate (0.35 g, 1.68 mmol) in dry THF (20 mL) at 0° C. and the resulting reaction mass was stirred at room temperature for 30 minutes. This was followed by the addition of benzyl bromide (0.43 g, 2.52 mmol) and stirred the resulting mixture at room temperature for 2 hours. The reaction was monitored by TLC (20% ethyl acetate in hexane). The reaction mixture was quenched with ice-water and extracted using ethyl acetate. The organic layer was washed with brine solution, dried over Na$_2$SO$_4$ and concentrated. Purification by column chromatography on silica gel (4% ethyl acetate in hexane) afforded 0.2 g of the product (50% yield).

$^1$HNMR (CDCl$_3$, 300 MHz): δ 7.6-7.4 (m, 5H), 4.5 (s, 2H), 4.3 (t, 3H), 4.2-4.1 (m, 1H), 3.6-3.4 (m, 1H), 2.8-2.5 (m, 4H), 1.8-1.7 (q, 2H), 1.5-1.4 (q, 2H), 1.1-1.0 (t, 3H). LCMS: 91.3%, m/z=298 (M+1).

Synthesis of Intermediate potassium 3-(benzyloxy)cyclobutane-1-sulfonate (I-25b)

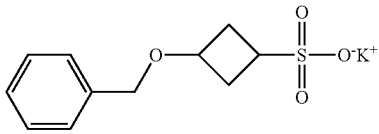

KSCN (68 mg, 0.66 mmol) and butyl 3-(benzyloxy)cyclobutane-1-sulfonate (0.18 g, 0.604 mmol) in DME-water mixture (1:1 ratio, 4 mL) were heated at 85° C. overnight. The reaction was monitored by TLC (50% ethyl acetate in hexane). The reaction mass was concentrated under reduced pressure and the crude residue obtained was washed with ether to afford 0.11 g of the product (70% yield).

$^1$HNMR (DMSO-$d_6$, 300 MHz): δ 7.4-7.2 (bs, 5H), 4.4-4.3 (s, 2H), 3.9-3.7 (m, 1H), 2.9-2.7 (m, 1H), 2.4-2.2 (m, 2H), 2.1-1.9 (m, 2H). LCMS: 99.03%, m/z=280 (M+1)

Synthesis of Intermediate 3-(benzyloxy)cyclobutane-1-sulfonyl chloride (I-25c)

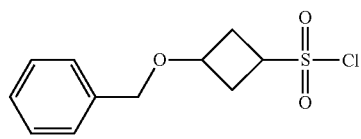 [SMILES: O=S(=O)(Cl)C1CC(OCc2ccccc2)C1]

POCl$_3$ (0.34 mL, 3.558 mmol) was added to a cooled solution of potassium 3-(benzyloxy)cyclobutane-1-sulfonate (0.5 g, 1.779 mmol) in dry DCM (10 mL) at 0° C. This was followed by the slow addition of diisopropyl ethyl amine (0.65 mL, 3.558 mmol) and stirred the resulting reaction mixture at 0° C. for 2 hours. The reaction was monitored by TLC (20% ethyl acetate in hexane). The reaction mixture was extracted with DCM. The organic layer was washed with water, brine solution, dried over Na$_2$SO$_4$ and concentrated. Purification by column chromatography on silica gel (8% ethyl acetate in hexane) afforded 0.15 g of the product (38% yield).

$^1$HNMR (CDCl$_3$, 300 MHz): δ 7.4-7.1 (m, 5H), 4.5 (s, 2H), 4.1-3.9 (m, 2H), 2.9-2.6 (m, 4H)

Synthesis of Intermediate 3-Benzyloxy-cyclobutanesulfonic acid [7-(2-fluoro-4-iodo-phenylamino)-6-methyl-5-oxo-2,3-dihydro-5H-thiazolo[3,2-a]pyridin-8-yl]-amide (I-25d)

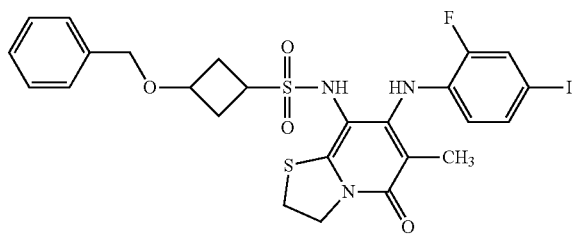 [SMILES: Cc1c(Nc2ccc(I)cc2F)c(NS(=O)(=O)C2CC(OCc3ccccc3)C2)c2n(c1=O)CCS2]

Using the same reaction conditions and workup as described for the preparation of Example 19A, 8-amino-7-(2-fluoro-4-iodo-phenylamino)-6-methyl-2,3-dihydro-thiazolo[3,2-a]pyridin-5-one (I-19f: 0.15 g, 0.35 mmol) in pyridine (2 mL) was reacted with 3-benzyloxy-cyclobutanesulfonyl chloride (0.1 g, 0.39 mmol) to afford the crude product. Purification by column chromatography on silica gel (50% ethylacetate in hexane) afforded 0.1 g of the product (43% yield).

$^1$HNMR (300 MHz, CDCl$_3$): δ 7.4-7.2 (m, 7H), 6.9-6.8 (s, 1H), 6.3-6.2 (t, 1H), 4.6-4.5 (t, 2H), 4.45 (s, 2H), 4.0-3.5 (t, 1H), 3.5-3.4 (m, 4H), 2.7-2.5 (m, 4H), 1.8 (s, 3H). LCMS: 85%, m/z=641.9 (M+1)

Synthesis of the Title Compound; 3-Hydroxy-cyclobutanesulfonic acid [7-(2-fluoro-4-iodo-phenylamino)-6-methyl-5-oxo-2,3-dihydro-5H-thiazolo[3,2-a]pyridin-8-yl]-amide (25A)

1M BCl$_3$ (0.46 mL, 0.468 mmol) was added to a solution of 3-benzyloxy-cyclobutanesulfonic acid [7-(2-fluoro-4-iodo-phenylamino)-6-methyl-5-oxo-2,3-dihydro-5H-thiazolo[3,2-a]pyridin-8-yl]-amide (0.1 g, 0.156 mmol) in dry DCM (3 mL) at −78° C. The resulting mixture was stirred at −78° C. for 3 hours. The reaction was monitored by TLC (10% MeOH in CHCl$_3$). The reaction mixture was quenched with methanol, basified with saturated NaHCO$_3$ solution and extracted with DCM. The organic layer was washed with brine, dried over Na$_2$SO$_4$ and concentrated. Purification by column chromatography on silica gel (4% MeOH in CHCl$_3$), followed by preparative HPLC afforded 0.015 g of the product (18% yield).

$^1$HNMR (300 MHz, CD$_3$OD): δ 7.5-7.4 (d, 1H), 7.4-7.3 (d, 1H), 6.4-6.3 (t, 1H), 4.6-4.5 (t, 2H), 4.2-4.0 (m, 1H), 3.6-3.5 (m, 3H), 2.7-2.6 (m, 2H), 2.4-2.2 (m, 2H), 1.8 (s, 3H). LCMS: 91.4%, m/z=551.9 (M+1). HPLC: 94.6%

Example 26

Synthesis of Cyclobutanesulfonic acid [7-(2-fluoro-4-iodo-phenylamino)-6-methyl-5-oxo-2,3-dihydro-5H-thiazolo[3,2-a]pyridin-8-yl]-amide (26A)

(26A)

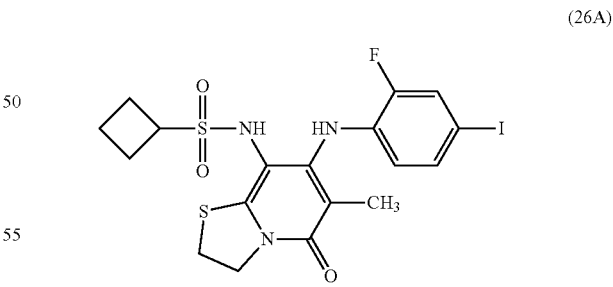

Using the same reaction conditions and workup as described for the preparation of Example 19A, 8-amino-7-(2-fluoro-4-iodo-phenylamino)-6-methyl-2,3-dihydro-thiazolo[3,2-a]pyridin-5-one (I-19f: 0.1 g, 0.23 mmol) in pyridine (2 mL) was reacted with cyclobutanesulfonyl chloride (0.04 g, 0.20 mmol) to afford the crude product. Purification by preparative HPLC afforded 15 mg of the product (12% yield).

$^1$HNMR (300 MHz, CD$_3$OD): δ 7.5-7.4 (d, 1H), 7.4-7.3 (d, 1H), 6.4-6.3 (t, 1H), 4.6-4.5 (t, 2H), 4.0-3.9 (m, 1H), 3.6-3.5

(m, 2H), 2.5-2.3 (m, 4H), 2.1-1.9 (m, 2H), 1.8 (s, 3H). LCMS: 95.5%, m/z=535.9 (M+1). HPLC: 90.9%

Example 27

Synthesis of Cyclobrobanesulfonic acid [7-(2-fluoro-4-iodo-phenylamino)-5-oxo-2,3-dihydro-5H-thiazolo[3,2-a]pyridin-8-yl]-amide (27A)

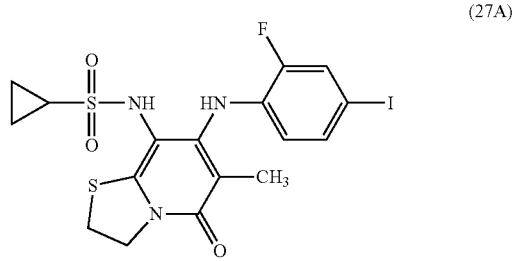 [SMILES: Cc1c(Nc2ccc(I)cc2F)c(NS(=O)(=O)C2CC2)c2n(c1=O)CCS2]
(27A)

Synthesis of Intermediate 7-Hydroxy-8-nitro-2,3-dihydro-thiazolo[3,2-a]pyridin-5-one (I-27a)

Using the same reaction conditions and workup as described for the preparation of Intermediate (I-19b), 2-nitromethylene-thiazolidine (0.65 g, 4.45 mmol) was reacted with malonic acid bis-(2,4,6-trichloro-phenyl) ester (1.5 g, 4.45 mmol) in Xylene (10 mL) to afford the crude product. Purification by column chromatography on silica gel (100% ethylacetate) afforded 0.3 g of the product (33% yield).

$^1$HNMR (300 MHz, DMSO-$D_6$): δ 11.6 (br s, 1H), 5.6-5.5 (s, 1H), 4.5-4.5 (t, 2H), 3.5-3.3 (t, 2H). LCMS: 100%, m/z=214.9 (M+1)

Synthesis of Intermediate Trifluoro-methanesulfonic acid 8-nitro-5-oxo-2,3-dihydro-5H-thiazolo[3,2-a]pyridin-7-yl ester (I-27b)

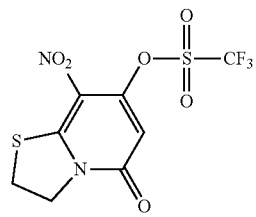 [SMILES: O=c1cc(OS(=O)(=O)C(F)(F)F)c([N+](=O)[O-])c2n1CCS2]

7-Hydroxy-8-nitro-2,3-dihydro-thiazolo[3,2-a]pyridin-5-one (0.3 g, 1.40 mmol) in DCM (10 mL) was reacted with triflic anhydride (0.26 mL, 1.54 mmol) and TEA (0.29 mL, 2.10 mmol) at −78° C. The resulting mixture was stirred at −78° C. for 2 hours. Purification by column chromatography on silica gel (30% ethylacetate in hexane) afforded 0.27 g of the product (56% yield).

$^1$HNMR (300 MHz, DMSO-$D_6$): δ 6.5 (s, 1H), 4.6-4.4 (t, 2H), 3.6-3.5 (t, 2H).
LCMS: 100%, m/z=346.8 (M+1)

Synthesis of Intermediate 7-(2-Fluoro-4-iodo-phenylamino)-8-nitro-2,3-dihydro-thiazolo[3,2-a]pyridin-5-one (I-27c)

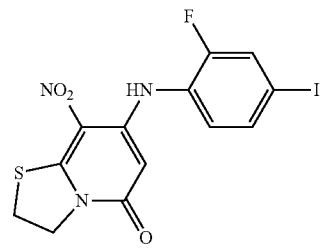 [SMILES: O=c1cc(Nc2ccc(I)cc2F)c([N+](=O)[O-])c2n1CCS2]

Trifluoro-methanesulfonic acid 8-nitro-5-oxo-2,3-dihydro-5H-thiazolo[3,2-a]pyridin-7-yl ester (0.6 g, 1.7 mmol) was reacted with 2-fluoro-4-iodo-phenylamine (0.45 g, 1.9 mmol), Pd(OAc)$_2$ (38 mg, 0.17 mmol), BINAP (0.1 g, 0.17 mmol) and cesium carbonate (0.84 g, 2.6 mmol) in toluene (20 mL) at reflux for 3 hours to afford the crude product. Purification by column chromatography on silica gel (30% ethylacetate in hexane) afforded 90 mg of the product (12% yield).

$^1$H-NMR (300 MHz, CDCl$_3$): δ 9.4 (s, 1H), 7.6-7.5 (t, 2H), 7.2-7.1 (t, 1H), 5.5-5.4 (s, 1H), 4.7-4.5 (t, 2H), 3.5-3.3 (t, 2H). LCMS: 94.84%, m/z=433.7 (M+1)

Synthesis of Intermediate 8-Amino-7-(2-fluoro-4-iodo-phenylamino)-2,3-dihydro-thiazolo[3,2-a]pyridin-5-one (I-27d)

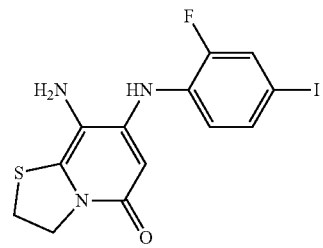 [SMILES: Nc1c(Nc2ccc(I)cc2F)cc(=O)n2c1SCC2]

Using the same reaction conditions and workup as described for the preparation of Intermediate (I-19f), 7-(2-fluoro-4-iodo-phenylamino)-8-nitro-2,3-dihydro-thiazolo[3,2-a]pyridin-5-one (0.08 g, 0.181 mmol) in ethanol (2 mL) was reacted with SnCl$_2$.H$_2$O (0.12 g, 0.541 mmol) and concentrated HCl (0.5 mL) to afford 0.08 g of crude product which was used in the next step without further purification. LCMS: 59%, m/z=403.9 (M+1).

Synthesis of the Title Compound; Cyclopropanesulfonic acid [7-(2-fluoro-4-iodo-phenylamino)-5-oxo-2,3-dihydro-5H-thiazolo[3,2-a]pyridin-8-yl]-amide (27A)

Using the same reaction conditions and workup as described for the preparation of Example 19A, 8-amino-7-(2- fluoro-4-iodo-phenylamino)-2,3-dihydro-thiazolo[3,2-a]pyridin-5-one (0.08 g, 0.199 mmol) in pyridine (1 mL) was reacted with cyclopropylsulfonyl chloride (33 mg, 0.238 mmol) to afford the crude product. Purification by preparative HPLC afforded 20 mg of the product (20% yield).

$^1$HNMR (300 MHz, DMSO-D$_6$): δ 9.0 (s, 1H), 7.8-7.7 (d, 1H), 7.6-7.5 (d, 2H), 7.2-7.1 (t, 1H), 5.1 (s, 1H), 4.4-4.2 (t, 2H), 3.5-3.3 (t, 2H), 2.9-2.7 (m, 1H), 1.0-0.8 (m, 4H). LCMS: 97.87%, m/z=507.9 (M+1). HPLC: 99.35%

Pharmacological Data

The utility of the compounds of the present invention may be demonstrated using any one of the following test procedures:

A BRAF-MEK-ERK cascade assay is used to evaluate the effects of the compounds as inhibitors of the MAP kinase pathway. An enzymatic cascade assay is set up using recombinant human activated BRAF (V599E) kinase (Cat No. 14-557), human full length unactive MEK1 kinase (Cat No. 14-706) and human full length unactive MAP Kinase 2/ERK2 (Cat No. 14-536) enzymes procured from Upstate. TR-FRET (Time resolved fluorescence resonance energy transfer) detection technology is used for the read out. The assay buffer solution contains 50 mM Tris pH 7.5, 10 mM MgCl2, 1 mM DTT, 0.01% Tween 20, 0.1 nM activated BRAF, 2 nM unactive MEK1, 10 nM unactive ERK2, 100 µM ATP and 500 nM long chain biotin-peptide substrate (LCB-FFKNIVTPRT-PPP) in a 384 well format. The kinase reaction is stopped after 90 minutes with 10 mM EDTA and Lance detection mix (2 nM Eu-labeled phospho-serine/threonine antibody (Cat. No. AD0176-Perkin Elmer), 20 nM SA-APC (Cat No. CR130-100-Perkin Elmer) is added. The TR-FRET signal (Excitation at 340 nm, Emission at 615 nm and 665 nm) is read with 50 µs delay time on a Victor3 V fluorimeter. The data is calculated using the ratio of readings at 665 nm to 615 nm. The final concentration of DMSO is 2.5% in the assay. Compounds are screened at 10 µM concentration with pre-incubation of the enzymes in the presence of test compound for 45 minutes.

Each individual IC50 is determined using a 10 point dose response curve generated by GraphPad Prism software Version 4 (San Diego, Calif., USA) using non linear regression curve fit for sigmoidal dose response (variable slope).

An in-vitro MAP kinase assay is set up using activated MAP kinase 2/ERK2 (Cat. No. 14-550) obtained from Upstate. TR-FRET detection technology is used for the read out.

The assay buffer solution contains 50 mM Tris pH 7.5, 10 mM MgCl$_2$, 1 mM DTT, 0.01% Tween 20, 1 nM activated ERK2, 100 µM ATP and 500 nM long chain biotin-peptide substrate (LCB-FFKNIVTPRTPPP) in a 384 well format. The kinase reaction is stopped after 90 minutes with 10 mM EDTA and Lance detection mix (2 nM Eu-labeled phospho-serine/threonine antibody (Cat. No. AD0176-Perkin Elmer), 20 nM SA-APC (Cat. No. CR130-100-Perkin Elmer) is added. The TR-FRET signal (excitation at 340 nm, emission at 615 nm and 665 nm) is read with 50 µs delay time on Victor3 V fluorimeter. The data is calculated using the ratio of readings at 665 nm to 615 nm. The final concentration of DMSO is 2.5% in the assay. Compounds are screened at 10 µM concentration with pre-incubation of the enzymes in the presence of test compound for 45 minutes.

The radioactive filter binding assay is standardized using recombinant human activated BRAF (V599E) kinase (Cat No. 14-557) and kinase dead MEK1 (K97R) (Cat No. 14-737) procured from Upstate. The incorporation of 32P into MEK1 (K97R) by BRAF (V599E) is measured with final assay buffer conditions of 50 mM Tris pH 7.5, 10 mM MgCl2, 1 mM DTT, 100 mM sucrose, 100 µM sodium orthovanadate, 5 µM ATP and 2 µCi [γ 32P] ATP and 500 mg MEK1 Kinase dead substrate. The enzymatic reaction is stopped after 120 minutes with 8N HCl (hydrochloric acid) and 1 mM ATP. The solution is spotted on P81 filter paper and washed 4 times with 0.75% orthophosphoric acid and lastly with acetone. The dried P81 filter papers are read in a Micro-beta Trilux scintillation counter. The final concentration of DMSO is 1% in the assay. Compounds are screened at 10 µM concentration with pre-incubation of the enzymes in the presence of test compound for 45 minutes.

These assays described above are fully detailed in Han, Shulin, et. al., *Bioorganic & Medicinal Chemistry Letters* (2005) 15, 5467-5473, and in Yeh, et. al., *Clin Cancer Res* (2007) 13 (5), 1576-1583.

The cell viability assay in A375 cells is set up in a 96-well plate format using XTT.

XTT is a yellow tetrazolium salt that is cleaved to an orange formazan dye by the mitochondria of metabolically active cells. The procedure allows for rapid determination in a microtitre plate, to give reproducible and sensitive results.

A375 cells are grown in DMEM media containing 10% FBS and 1 mM sodium pyruvate. Cells are trypsinized and seeded at 1000 cells/well. After allowing the cells to adhere overnight, compound is added to the wells at the following final concentrations: 10, 3, 1, 0.3, 0.1, 0.03, 0.01, 0.001, and 0.0001 µM. The assay is set up in triplicates for each concentration. DMSO concentrations are kept at 0.5%/well. Three days after compound addition, the XTT assay is performed. Wells are washed once with PBS. 100 µL of DMEM media without phenol red or FBS is added to each well. A working solution of XTT containing 1 mg/ml XTT and 100 µL of PMS (stock concentration 0.383 mg/ml) per 5 ml is prepared. 50 µL of the working solution of XTT is added to each well. Absorbance of the plate is read at 465 nm using a Spectramax 190 (Molecular Devices). The absorbance from wells with media and XTT alone, but without cells is considered the blank and subtracted from readings from all wells.

Percentage viability is calculated considering the blank subtracted value from wells treated with DMSO alone as 100% viable. GI50 values are calculated using Graphpad Prism, using non-linear regression curve fit for sigmoidal dose response (variable slope).

The cell viability assay is further described in Scudiero, et. al., Cancer Research (1988) 48, 4827-4833; Weislow, et. al., *J. Natl. Cancer Institute*, (1989) 81, 577-586; and Roehm, et. al., *J. Immunol. Methods* [1991]142:257-265.

The compounds of the above Examples were evaluated as inhibitors of the MAP kinase pathway in a BRAF-MEK-ERK enzymatic cascade assay and in the cell viability assay described above. The results are collated in Table 1 below.

TABLE 1

| Example No. | IUPAC Name | % inhibition | GI$_{50}$ µM |
|---|---|---|---|
| 1A | Cyclopropanesulfonic acid [1-benzyl-7-(4-bromo-2-fluoro-phenylamino)-6-methyl-5-oxo-1,2,3,5-tetrahydro-imidazo[1,2-a]pyridin-8-yl]-amide | 70% | — |
| 2A | Cyclopropanesulfonic acid [7-(4-bromo-2-fluoro-phenylamino)-6-methyl-5-oxo-1,2,3,5-tetrahydro-imidazo[1,2-a]pyridin-8-yl]-amide | 100% | 0.8 |

TABLE 1-continued

| Example No. | IUPAC Name | % inhibition | GI$_{50}$ μM |
|---|---|---|---|
| 3A | Cyclopropanesulfonic acid [7-(2-fluoro-4-iodo-phenylamino)-6-methyl-5-oxo-1,2,3,5-tetrahydro-imidazo[1,2-a]pyridin-8-yl]-amide | 100% | 0.019 |
| 4A | 1-(2,3-Dihydroxy-propyl)-cyclopropanesulfonic acid [7-(4-bromo-2-fluoro-phenylamino)-6-methyl-5-oxo-1,2,3,5-tetrahydro-imidazo[1,2-a]pyridin-8-yl]-amide | 100% | 2.88 |
| 5A | 1-(2,3-Dihydroxy-propyl)-cyclopropanesulfonic acid [7-(2-fluoro-4-iodo-phenylamino)-6-methyl-5-oxo-1,2,3,5-tetrahydro-imidazo[1,2-a]pyridin-8-yl]-amide | 100% | 0.293 |
| 6A | 3-Hydroxy-cyclobutanesulfonic acid [7-(2-fluoro-4-iodo-phenylamino)-6-methyl-5-oxo-1,2,3,5-tetrahydro-imidazo[1,2-a]pyridin-8-yl]-amide | 100% | 1.38 |
| 7A | Cyclopropanesulfonic acid [7-(2-fluoro-4-iodo-phenylamino)-6-methyl-5-oxo-2,3-dihydro-5H-oxazolo[3,2-a]pyridin-8-yl]-amide | 99% | 0.026 |
| 8A | 2-Hydroxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide | 100% | 0.122 |
| 9A | 1-(2-Hydroxy-ethyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide | 100% | 0.019 |
| 10A | 1-(2,3-Dihydroxy-propyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide | 100% | 0.033 |
| 11A | 1-Hydroxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide | 100% | 0.02 |
| 12A | 1-(3-Hydroxy-propyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide | 100% | 0.011 |
| 13A | 3-Hydroxy-cyclobutanesulfonic acid [7-(2-fluoro-4-iodo-phenylamino)-6-methyl-5-oxo-2,3-dihydro-5H-oxazolo[3,2-a]pyridin-8-yl]-amide | 100% | 0.122 |
| 14A | Cyclobutanesulfonic acid [7-(2-fluoro-4-iodo-phenylamino)-6-methyl-5-oxo-2,3-dihydro-5H-oxazolo[3,2-a]pyridin-8-yl]-amide | 100% | 0.016 |
| 15A | 3-(1,3-dihydroxypropan-2-yl)-N-(7-(2-fluoro-4-iodophenylamino)-6-methyl-5-oxo-3,5-dihydro-2H-oxazolo[3,2-a]pyridin-8-yl)cyclobutane-1-sulfonamide | 100% | 1.53 |
| 16A | N-(7-(2-fluoro-4-iodophenylamino)-6-methyl-5-oxo-3,5-dihydro-2H-oxazolo[3,2-a]pyridin-8-yl)-1-(3-methyloxetan-3-yl)methanesulfonamide | 100% | 1.30 |
| 17A | N-(7-(2-fluoro-4-iodophenylamino)-6-methyl-5-oxo-3,5-dihydro-2H-oxazolo[3,2-a]pyridin-8-yl)-2-(oxetan-3-yl)ethanesulfonamide | 100% | 1.73 |
| 18A | N-(7-(2-fluoro-4-iodophenylamino)-6-methyl-5-oxo-3,5-dihydro-2H-oxazolo[3,2-a]pyridin-8-yl)-4-hydroxy-3-(hydroxymethyl)butane-1-sulfonamide | 100% | 4.26 |
| 19A | Cyclopropanesulfonic acid [7-(2-fluoro-4-iodo-phenylamino)-6-methyl-5-oxo-2,3-dihydro-5H-thiazolo[3,2-a]pyridin-8-yl]-amide | 100% | 0.0003 |
| 20A | 1-(2,3-Dihydroxy-propyl)-cyclopropanesulfonic acid [7-(2-fluoro-4-iodo-phenylamino)-6-methyl-5-oxo-2,3-dihydro-5H-thiazolo[3,2-a]pyridin-8-yl]-amide | 100% | 0.054 |
| 21A | 2-Hydroxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide | 100% | 0.158 |
| 22A | 1-Hydroxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide | 97% | 0.061 |
| 23A | N-[7-(2-Fluoro-4-iodo-phenylamino)-6-methyl-5-oxo-2,3-dihydro-5H-thiazolo[3,2-a]pyridin-8-yl]-dimethylaminosulfonamide | 100% | 0.107 |
| 24A | Cyclopentanesulfonic acid [7-(2-fluoro-4-iodo-phenylamino)-6-methyl-5-oxo-2,3-dihydro-5H-thiazolo[3,2-a]pyridin-8-yl]-amide | 100% | 0.192 |
| 25A | 3-Hydroxy-cyclobutanesulfonic acid [7-(2-fluoro-4-iodo-phenylamino)-6-methyl-5-oxo-2,3-dihydro-5H-thiazolo[3,2-a]pyridin-8-yl]-amide | 100% | 0.922 |
| 26A | Cyclobutanesulfonic acid [7-(2-fluoro-4-iodo-phenylamino)-6-methyl-5-oxo-2,3-dihydro-5H-thiazolo[3,2-a]pyridin-8-yl]-amide | 100% | 0.156 |
| 27A | Cyclopropanesulfonic acid [7-(2-fluoro-4-iodo-phenylamino)-5-oxo-2,3-dihydro-5H-thiazolo[3,2-a]pyridin-8-yl]-amide | 100% | 0.064 |

What is claimed is:

1. A compound of Formula (IA)

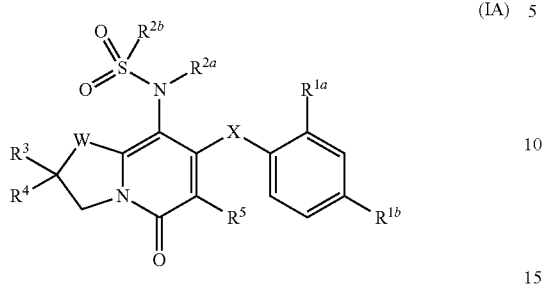

(IA)

wherein

X is —N($R^6$)—, where $R^6$ is H or ($C_1$-$C_6$)alkyl;

$R^{1a}$ and $R^{1b}$ are each independently selected from hydroxyl, cyano, nitro, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, halogen, ($C_1$-$C_6$)alkyl-C(O)—, —C(O)OH, —C(O)—O($C_1$-$C_6$)alkyl, amino, ($C_1$-$C_6$)alkylNH—, di(($C_1$-$C_6$)_alkyl)N—, ($C_1$-$C_6$)alkylNH—C(O)—, di(($C_1$-$C_6$)alkyl)N—C(O)—, ($C_1$-$C_6$)alkyl-C(O)—NH—, ($C_1$-$C_6$)alkyl-C(O)—N(($C_1$-$C_6$)alkyl)-, ($C_1$-$C_6$)alkyl-$SO_2$—NH—, ($C_1$-$C_6$)alkyl-$SO_2$—N(($C_1$-$C_6$)alkyl)-, ($C_1$-$C_6$)alkyl-S—, ($C_1$-$C_6$)alkyl-S(O)—, ($C_1$-$C_6$)alkyl-$SO_2$—, $NH_2$—$SO_2$—, ($C_1$-$C_6$)alkylNH—$SO_2$— and di(($C_1$-$C_6$)alkyl)N—$SO_2$—, where each of said ($C_1$-$C_6$)alkyl, ($C_2$-$C_6$)alkenyl, and ($C_2$-$C_6$)alkynyl moieties are optionally substituted by one or more substituents each independently selected from halogen, hydroxyl, ($C_1$-$C_6$)alkoxy, amino, ($C_1$-$C_6$)alkyl-NH—, di(($C_1$-$C_6$)alkyl)N— or cyano;

$R^{2a}$ is H or $C_{1-6}$-alkyl;

$R^{2b}$ is a chemical moiety selected from ($C_1$-$C_6$)alkyl, ($C_2$-$C_6$)alkenyl, ($C_2$-$C_6$)alkynyl, $NR^{10}R^{12}$, cycloalkyl, aryl, heterocycloalkyl, or heteroaryl, wherein said chemical moiety is optionally substituted by one to three substituents each independently selected from halogen, cyano, hydroxyl, ($C_1$-$C_6$)alkoxy, ($C_2$-$C_6$)alkenyloxy, ($C_2$-$C_6$)alkynyloxy, ($C_1$-$C_6$)alkyl-S—, halo-substituted ($C_1$-$C_6$)alkyl, amino, ($C_1$-$C_6$)alkylNH—, di(($C_1$-$C_6$)alkyl)N—, HC(O)—NH—, ($C_1$-$C_6$)alkyl-C(O)—NH—, HC(O)—N($C_1$-$C_6$)alkyl)-, ($C_1$-$C_6$)alkyl-C(O)—N(($C_1$-$C_6$)alkyl)-, monocyclic cycloalkyl or monocyclic heterocycloalkyl, where said cycloalkyl and said heterocycloalkyl are optionally substituted by one or two substituents each independently selected from halogen, cyano, hydroxyl, ($C_1$-$C_6$)alkoxy, ($C_2$-$C_6$)alkenyloxy, ($C_2$-$C_6$)alkynyloxy, ($C_1$-$C_6$)alkyl-S—, $C_{1-6}$-haloalkyl, amino, ($C_1$-$C_6$)alkylNH—, di(($C_1$-$C_6$)alkyl)N—, HC(O)—NH—, ($C_1$-$C_6$)alkyl-C(O)—NH—, HC(O)—N($C_1$-$C_6$)alkyl)-, or ($C_1$-$C_6$)alkyl-C(O)—N(($C_1$-$C_6$)alkyl)-;

W is $NR^{22}$, O, or S;

$R^3$ and $R^4$ are each independently H, ($C_1$-$C_6$)alkyl, halo-substituted ($C_1$-$C_6$)alkyl, hydroxy($C_1$-$C_6$)alkyl, or ($C_1$-$C_6$)alkoxy;

$R^5$ is H, halogen, ($C_1$-$C_3$)alkyl, or halo-substituted ($C_1$-$C_3$)alkyl;

$R^{10}$ and $R^{12}$ are each independently H, or a chemical moiety selected from ($C_1$-$C_6$)alkyl, ($C_2$-$C_6$)alkenyl, ($C_2$-$C_6$)alkynyl, ($C_1$-$C_6$)alkylC(O)—, ($C_1$-$C_6$)alkoxy, ($C_3$-$C_{14}$)cycloalkyl, ($C_6$-$C_{14}$)aryl, 4- to 14-membered cycloheteroalkyl, or 5- to 14-membered heteroaryl, wherein each of said chemical moieties are optionally substituted by one or more substituents each independently selected from halogen, hydroxyl, ($C_1$-$C_6$)alkoxy, amino, ($C_1$-$C_6$)alkylamino, di-(($C_1$-$C_6$)alkyl)amino or cyano; and $R^{22}$ is H, or a chemical moiety selected from ($C_1$-$C_6$)alkyl, ($C_2$-$C_6$)alkenyl, ($C_2$-$C_6$)alkynyl, cycloalkyl, aryl, heterocycloalkyl, aryl-($C_1$-$C_6$)alkyl-, ($C_1$-$C_6$)alkyl-aryl-, or diaryl-($C_1$-$C_6$)alkyl-, where each of said chemical moieties is optionally substituted by one or more substituents each independently selected from hydroxyl, cyano, nitro, ($C_1$-$C_6$)alkyl, ($C_2$-$C_6$)alkenyl, ($C_2$-$C_6$)alkynyl, ($C_1$-$C_6$)alkoxy, ($C_2$-$C_6$)alkenyloxy, ($C_2$-$C_6$)alkynyloxy, halogen, ($C_1$-$C_6$)alkyl-C(O)—, —C(O)OH, —C(O)—O($C_1$-$C_6$)alkyl, amino, ($C_1$-$C_6$)alkylNH—, di(($C_1$-$C_6$)_alkyl)N—, ($C_1$-$C_6$)alkylNH—C(O)—, di(($C_1$-$C_6$)alkyl)N—C(O)—, ($C_1$-$C_6$)alkyl-C(O)—NH—, ($C_1$-$C_6$)alkyl-C(O)—N(($C_1$-$C_6$)alkyl)-, ($C_1$-$C_6$)alkyl-$SO_2$—NH—, ($C_1$-$C_6$)alkyl-$SO_2$—N(($C_1$-$C_6$)alkyl)-, ($C_1$-$C_6$)alkyl-S—, ($C_1$-$C_6$)alkyl-S(O)—, ($C_1$-$C_6$)alkyl-$SO_2$—, $NH_2$—$SO_2$-, ($C_1$-$C_6$)alkylNH—$SO_2$— and di(($C_1$-$C_6$)alkyl)N—$SO_2$—, where each of said ($C_1$-$C_6$)alkyl, ($C_2$-$C_6$)alkenyl, and ($C_2$-$C_6$)alkynyl moieties are optionally substituted by one or more substituents each independently selected from halogen, hydroxyl, ($C_1$-$C_6$)alkoxy, amino, ($C_1$-$C_6$)alkyl-NH—, di(($C_1$-$C_6$)alkyl)N—, or cyano;

or a pharmaceutically acceptable salt thereof.

2. A compound of Formula (IB)

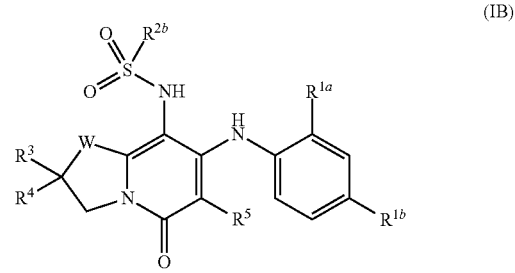

(IB)

wherein $R^{1a}$ and $R^{1b}$ are each independently hydroxyl, cyano, nitro, ($C_1$-$C_6$)alkyl, ($C_2$-$C_6$)alkenyl, ($C_2$-$C_6$)alkynyl, ($C_1$-$C_6$)alkoxy, halogen, amino, or ($C_1$-$C_6$)alkyl-NH—;

$R^{2b}$ is (i) 3- to 6-membered cycloalkyl, where said cycloalkyl is optionally substituted with hydroxyl, ($C_1$-$C_6$)alkyl, ($C_2$-$C_6$)alkenyl, or ($C_2$-$C_6$)alkynyl, wherein said ($C_1$-$C_6$)alkyl, said ($C_2$-$C_6$)alkenyl, and said ($C_2$-$C_6$)alkynyl are optionally substituted with 1 to 3 hydroxyl, (ii) ($C_1$-$C_6$)alkyl substituted by a monocyclic 3- to 6-membered cycloalkyl or a monocyclic 3- to 6-membered heterocycloalkyl containing 1 to 3 heteroatoms selected from O, S or N, where said substituted alkyl is optionally substituted with one to three substituents each independently selected from the group consisting of halogen, cyano, hydroxyl, ($C_1$-$C_6$)alkoxy, ($C_1$-$C_6$)alkyl-S—, halo-substituted ($C_1$-$C_6$)alkyl, amino, ($C_1$-$C_6$)alkyl-NH—, di-(($C_1$-$C_6$)alkyl)-N—, and ($C_1$-$C_6$)alkylC(O)—NH—, (iii) ($C_2$-$C_6$)alkenyl substituted by a monocyclic 3- to 6-membered cycloalkyl or a monocyclic 3- to 6-membered heterocycloalkyl containing 1 to 3 heteroatoms selected from O, S or N, where said substituted alkenyl is optionally substituted with one to three substituents each independently selected from the group consisting of halogen, cyano, hydroxyl, $(C_1-C_6)$alkoxy, $(C_1-C_6)$alkyl-S—, halo-substituted $(C_1-C_6)$alkyl, amino, $(C_1-C_6)$alkyl-NH—, di-$((C_1-C_6)$alkyl)-N—, and $(C_1-C_6)$alkylC(O)—NH—, (iv) $(C_2-C_6)$alkynyl substituted by a monocyclic 3- to 6-membered cycloalkyl or a monocyclic 3- to 6-membered heterocycloalkyl containing 1 to 3 heteroatoms selected from O, S or N, where said substituted alkynyl is optionally substituted with one to three substituents each independently selected from the group consisting of halogen, cyano, hydroxyl, $(C_1-C_6)$alkoxy, $(C_1-C_6)$alkyl-S—, halo-substituted $(C_1-C_6)$alkyl, amino, $(C_1-C_6)$alkyl-NH—, di-$((C_1-C_6)$alkyl)-N—, and $(C_1-C_6)$alkylC(O)—NH—, or (v) di$((C_1-C_6)$alkyl)amine;

$R^3$ is H;
$R^4$ is H or methyl;
W is $NR^{22}$, O, or S, where $R^{22}$ is H, methyl, ethyl, phenyl, benzyl, or phenethyl;
$R^5$ is H, halogen, $(C_1-C_3)$alkyl, or halo-substituted $(C_1-C_3)$ alkyl;

or a pharmaceutically acceptable salt thereof.

3. The compound of claim 2 wherein $R^{1a}$ and $R^{1b}$ are each independently halogen; or a pharmaceutically acceptable salt thereof.

4. A compound of Formula (IC)

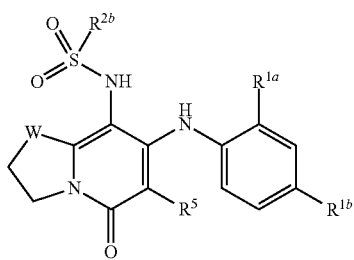

(IC)

wherein
$R^{1a}$ is F;
$R^{1b}$ is Br or I;
$R^{2b}$ is
(i) 3- to 6-membered cycloalkyl, where said cycloalkyl is optionally substituted with hydroxyl or $(C_1-C_6)$ alkyl, wherein said $(C_1-C_6)$alkyl is optionally substituted with 1 to 3 hydroxyl,
(ii) $(C_1-C_6)$alkyl, where said $(C_1-C_6)$alkyl is optionally substituted with oxetanyl or 1 to 3 hydroxyl, or
(iii) —N(CH$_3$)$_2$;
W is O, S or N($R^{22}$), where $R^{22}$ is H or benzyl; and
$R^5$ is H, F, Cl, CH$_3$ or CF$_3$;

or a pharmaceutically acceptable salt thereof.

5. The compound of claim 4 wherein W is O; or a pharmaceutically acceptable salt thereof.

6. The compound of claim 1 selected from the group consisting of:
Cyclopropanesulfonic acid [7-(2-fluoro-4-iodo-phenylamino)-6-methyl-5-oxo-2,3-dihydro-5H-oxazolo[3,2-a]pyridin-8-yl]-amide;
2-Hydroxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide;
1-(2-Hydroxy-ethyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide;
1-(2,3-Dihydroxy-propyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide;
1-Hydroxymethyl-cyclopropanesulfonic acid [7-(2-fluoro-4-iodo-phenylamino)-6-methyl-5-oxo-2,3-dihydro-5H-oxazolo[3,2-a]pyridin-8-yl]-amide;
1-(3-Hydroxy-propyl)-cyclopropanesulfonic acid [7-(2-fluoro-4-iodo-phenylamino)-6-methyl-5-oxo-2,3-dihydro-5H-oxazolo[3,2-a]pyridin-8-yl]-amide;
3-Hydroxy-cyclobutanesulfonic acid [7-(2-fluoro-4-iodo-phenylamino)-6-methyl-5-oxo-2,3-dihydro-5H-oxazolo[3,2-a]pyridin-8-yl]-amide;
Cyclobutanesulfonic acid [7-(2-fluoro-4-iodo-phenylamino)-6-methyl-5-oxo-2,3-dihydro-5H-oxazolo[3,2-a]pyridin-8-yl]-amide;
3-(1,3-dihydroxypropan-2-yl)-N-(7-(2-fluoro-4-iodophenylamino)-6-methyl-5-oxo-3,5-dihydro-2H-oxazolo[3,2-a]pyridin-8-yl)cyclobutane-1-sulfonamide;
N-(7-(2-fluoro-4-iodophenylamino)-6-methyl-5-oxo-3,5-dihydro-2H-oxazolo[3,2-a]pyridin-8-yl)-1-(3-methyloxetan-3-yl)methanesulfonamide;
N-(7-(2-fluoro-4-iodophenylamino)-6-methyl-5-oxo-3,5-dihydro-2H-oxazolo[3,2-a]pyridin-8-yl)-2-(oxetan-3-yl)ethanesulfonamide; and
N-(7-(2-fluoro-4-iodophenylamino)-6-methyl-5-oxo-3,5-dihydro-2H-oxazolo[3,2-a]pyridin-8-yl)-4-hydroxy-3-(hydroxymethyl)butane-1-sulfonamide;

or a pharmaceutically acceptable salt thereof.

7. The compound of claim 4 wherein W is S; or a pharmaceutically acceptable salt thereof.

8. The compound of claim 1 selected from the group consisting of:
Cyclopropanesulfonic acid [7-(2-fluoro-4-iodo-phenylamino)-6-methyl-5-oxo-2,3-dihydro-5H-thiazolo[3,2-a]pyridin-8-yl]-amide;
1-(2,3-Dihydroxy-propyl)-cyclopropanesulfonic acid [7-(2-fluoro-4-iodo-phenylamino)-6-methyl-5-oxo-2,3-dihydro-5H-thiazolo[3,2-a]pyridin-8-yl]-amide;
2-Hydroxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide;
1-Hydroxymethyl-cyclopropanesulfonic acid [7-(2-fluoro-4-iodo-phenylamino)-6-methyl-5-oxo-2,3-dihydro-5H-thiazolo[3,2-a]pyridin-8-yl]-amide;
N-[7-(2-Fluoro-4-iodo-phenylamino)-6-methyl-5-oxo-2,3-dihydro-5H-thiazolo[3,2-a]pyridin-8-yl]-dimethylaminosulfonamide;
Cyclopentanesulfonic acid [7-(2-fluoro-4-iodo-phenylamino)-6-methyl-5-oxo-2,3-dihydro-5H-thiazolo[3,2-a]pyridin-8-yl]-amide;
3-Hydroxy-cyclobutanesulfonic acid [7-(2-fluoro-4-iodo-phenylamino)-6-methyl-5-oxo-2,3-dihydro-5H-thiazolo[3,2-a]pyridin-8-yl]-amide;
Cyclobutanesulfonic acid [7-(2-fluoro-4-iodo-phenylamino)-6-methyl-5-oxo-2,3-dihydro-5H-thiazolo[3,2-a]pyridin-8-yl]-amide; and
Cyclopropanesulfonic acid [7-(2-fluoro-4-iodo-phenylamino)-5-oxo-2,3-dihydro-5H-thiazolo[3,2-a]pyridin-8-yl]-amide;

or a pharmaceutically acceptable salt thereof.

9. The compound of claim 4 wherein W is NH; or a pharmaceutically acceptable salt thereof.

10. The compound of claim 1 selected from the group consisting of:

Cyclopropanesulfonic acid [7-(4-bromo-2-fluoro-phenylamino)-6-methyl-5-oxo-1,2,3,5-tetrahydro-imidazo[1,2-a]pyridin-8-yl]-amide;

Cyclopropanesulfonic acid [7-(2-fluoro-4-iodo-phenylamino)-6-methyl-5-oxo-1,2,3,5-tetrahydro-imidazo[1,2-a]pyridin-8-yl]-amide;

1-(2,3-Dihydroxy-propyl)-cyclopropanesulfonic acid [7-(4-bromo-2-fluoro-phenylamino)-6-methyl-5-oxo-1,2,3,5-tetrahydro-imidazo[1,2-a]pyridin-8-yl]-amide;

1-(2,3-Dihydroxy-propyl)-cyclopropanesulfonic acid [7-(2-fluoro-4-iodo-phenylamino)-6-methyl-5-oxo-1,2,3,5-tetrahydro-imidazo[1,2-a]pyridin-8-yl]-amide; and 3-Hydroxy-cyclobutanesulfonic acid [7-(2-fluoro-4-iodo-phenylamino)-6-methyl-5-oxo-1,2,3,5-tetrahydro-imidazo[1,2-a]pyridin-8-yl]-amide;

or a pharmaceutically acceptable salt thereof.

11. A pharmaceutical composition comprising a pharmaceutical composition comprising a compound according to claim 1, or pharmaceutically acceptable salt thereof, and a pharmaceutically acceptable excipient.

* * * * *